(12) United States Patent
Han et al.

(10) Patent No.: US 10,266,598 B2
(45) Date of Patent: Apr. 23, 2019

(54) DUAL RECEPTOR ANTAGONISTIC ANTIGEN-BINDING PROTEINS AND USES THEREOF

(71) Applicant: AMGEN INC., Thousand Oaks, CA (US)

(72) Inventors: Huiquan Han, Thousand Oaks, CA (US); Xiaolan Zhou, Newbury Park, CA (US); Qing Chen, Oxnard, CA (US); Mei-Mei Tsai, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 15/247,792

(22) Filed: Aug. 25, 2016

(65) Prior Publication Data

US 2017/0107288 A1   Apr. 20, 2017

Related U.S. Application Data

(63) Continuation of application No. 14/407,421, filed as application No. PCT/US2013/045245 on Jun. 11, 2013, now Pat. No. 9,453,080.

(60) Provisional application No. 61/658,237, filed on Jun. 11, 2012.

(51) Int. Cl.
| | | |
|---|---|---|
| *C07K 16/28* | (2006.01) | |
| *C07K 16/46* | (2006.01) | |
| *A61K 39/00* | (2006.01) | |
| *C07K 16/42* | (2006.01) | |

(52) U.S. Cl.
CPC .......... *C07K 16/2863* (2013.01); *C07K 16/42* (2013.01); *C07K 16/468* (2013.01); *A61K 2039/505* (2013.01); *C07K 2317/21* (2013.01); *C07K 2317/31* (2013.01); *C07K 2317/565* (2013.01); *C07K 2317/75* (2013.01); *C07K 2317/76* (2013.01); *C07K 2317/92* (2013.01)

(58) Field of Classification Search
CPC .............. C07K 16/2863; C07K 16/468; A61K 2039/505
See application file for complete search history.

(56) References Cited

U.S. PATENT DOCUMENTS

| | | | |
|---|---|---|---|
| 9,453,080 B2 * | 9/2016 | Han .................. | C07K 16/2863 |
| 2006/0068468 A1 | 3/2006 | Knopf et al. | |
| 2010/0120627 A1 | 5/2010 | Belouchi et al. | |
| 2010/0272734 A1 | 10/2010 | Berger et al. | |
| 2011/0280873 A1 | 11/2011 | Presta et al. | |

FOREIGN PATENT DOCUMENTS

| | | |
|---|---|---|
| WO | WO 2008/109167 | 9/2008 |
| WO | WO 2010/062383 | 6/2010 |
| WO | WO 2010/125003 | 11/2010 |
| WO | WO 2013/106175 | 7/2013 |

OTHER PUBLICATIONS

Bogdanovich et al. Myostatin blockade improves function but not histopathology in a murine model of limb-girdle muscular dystrophy 2C. Muscle Nerve. Mar. 2008;37(3):308-16.*
Chen et al. Selection and analysis of an optimized anti-VEGF antibody: crystal structure of an affinity-matured Fab in complex with antigen. J Mol Biol. Nov. 5, 1999;293(4):865-81.*
De Pascalis et al. Grafting of "abbreviated" complementarity-determining regions containing specificity-determining residues essential for ligand contact to engineer a less immunogenic humanized monoclonal antibody. J Immunol. Sep. 15, 2002;169(6):3076-84.*
Holzbaur et al. Myostatin inhibition slows muscle atrophy in rodent models of amyotrophic lateral sclerosis. Neurobiol Dis. Sep. 2006;23(3):697-707. Epub Jul. 11, 2006.*
MacCallum et al. Antibody-antigen interactions: contact analysis and binding site topography. J Mol Biol. Oct. 11, 1996;262(5):732-45.*
Rudikoff et al. Single amino acid substitution altering antigen-binding specificity. Proc Natl Acad Sci U S A. Mar. 1982;79(6):1979-83.*
Vajdos et al. Comprehensive functional maps of the antigen-binding site of an anti-ErbB2 antibody obtained with shotgun scanning mutagenesis. J Mol Biol. Jul. 5, 2002;320(2):415-28.*
Wu et al. Humanization of a murine monoclonal antibody by simultaneous optimization of framework and CDR residues. J Mol Biol. Nov. 19, 1999;294(1):151-62.*
Zhou et al. Reversal of cancer cachexia and muscle wasting by ActRIIB antagonism leads to prolonged survival. Cell. Aug. 20, 2010;142(4):531-43.*
PCT International Search Report and Written Opinion for PCT/US2013/045245, dated Feb. 18, 2014, 17 Pages.
Funaba, M., et al., Immunolocalization of Type I or Type II Activin Receptors in the Rat Brain, Journal of Neuroendocrinology, 1997, pp. 105-111, vol. 9.
Lynch, G., et al., "Therapeutic approaches for muscle wasting disorders," Pharmacology & Therapeutics, 2007, pp. 461-487, No. 113, Science Direct.
International Nonproprietary Names for Pharmaceutical Substances (INN) Denominations communes internationales des Substances pharmaceutiques (DCI), WHO Drug Information, Jan. 1, 2012, pp. 401-471, vol. 26, No. 4. Can be retrieved from the internet <URL:http://www.who.int/medicines/publications/druginformation/issues/-PL 108. pdf>.
Extended European Search Report for European Patent Application No. EP 13804428.4, dated Jul. 1, 2016, 8 Pages.

(Continued)

*Primary Examiner* — Ruixiang Li
(74) *Attorney, Agent, or Firm* — Lisa E. Alexander

(57) ABSTRACT

This disclosure relates to antagonistic dual receptor antigen-binding proteins, e.g. antibodies and methods of using the dual receptor antibodies for treatment of pathological diseases. The dual receptor antibodies may comprise an antibody to ActRII receptors and may be used to treat pathological condition. The pathological conditions can comprise muscle wasting diseases or any disease that requires stimulation of muscle growth.

11 Claims, 15 Drawing Sheets

Specification includes a Sequence Listing.

(56) References Cited

OTHER PUBLICATIONS

Office Action for Chinese Patent Application No. CN 201380042597.X, dated Aug. 5, 2016, 18 Pages.
Office Actin for New Zealand Patent Application No. 703724, dated Aug. 9, 2016, 6 Pages.
Office Action for Chilean Patent Application No. 2014-03372, dated Jul. 15, 2016, 36 Pages.
Office Action for Eurasian Patent Application No. 201492282, dated Sep. 30, 2016, 4 Pages.

* cited by examiner

| | | |
|---|---|---|
| HC-CDR1 | NSAMS | (SEQ ID NO: 3) |
| HC-CDR2 | GISVTGGSTFYTDSVKGR | (SEQ ID NO: 4) |
| HC-CDR3 | VYYYSFFDY | (SEQ ID NO: 5) |
| LC-CDR1 | GFNSGSVSTSYWPS | (SEQ ID NO: 6) |
| LC-CDR2 | NTNTRSS | (SEQ ID NO: 7) |
| LC-CDR3 | VLWMGSGIWV | (SEQ ID NO: 8) |

R31-1

| | | |
|---|---|---|
| HC-CDR1 | NYAMS | (SEQ ID NO: 9) |
| HC-CDR2 | GISVTGGSTYYTDSVKGR | (SEQ ID NO: 10) |
| HC-CDR3 | VYYSSFFDY | (SEQ ID NO: 11) |
| LC-CDR1 | GFNSGSVSTSYYPS | (SEQ ID NO: 12) |
| LC-CDR2 | NTNTRSS | (SEQ ID NO: 13) |
| LC-CDR3 | VLYMGSGIWV | (SEQ ID NO: 14) |

FIG. 2A

HC sequence of M43 (SEQ ID NO: 15)

EVQLLESGGGLVQPGGSLRLSCAASGFTFRNSAMSWVRQ
APGKGLEWVSGISVTGGSTFYTDSVKGRFTVSRDNSRNT
LYLQMNSLRAEDTAVYYCAKVYYYSFFDYWGQGTLVTVS
SASTKGPSVFPLAPCSRSTSESTAALGCLVKDYFPEPVT
VSWNSGALTSGVHTFPAVLQSSGLYSLSSVVTVPSSNFG
TQTYTCNVDHKPSNTKVDKTVERKCCVECPPCPAPPVAG
PSVFLFPPKPKDTLMISRTPEVTCVVVDVSHEDPEVQFN
WYVDGVEVHNAKTKPREEQFNSTFRVVSVLTVVHQDWLN
GKEYKCKVSNKGLPAPIEKTISKTKGQPREPQVYTLPPS
REEMTKNQVSLTCLVKGFYPSDIAVEWESNGQPENNYKT
TPPMLDSDGSFFLYSKLTVDKSRWQQGNVFSCSVMHEAL
HNHYTQKSLSLSPGK

LC sequence of M43 (SEQ ID NO: 16)

QTVVTQEPSFSVSPGGTVTLTCGFNSGSVSTSYWPSWYQ
QTPGQAPRTLIYNTNTRSSGVPDRFSGSILGNKAALTIT
GAQADDESDYYCVLWMGSGIWVFGGGTKLTVLGQPKANP
TVTLFPPSSEELQANKATLVCLISDFYPGAVTVAWKADG
SPVKAGVETTKPSKQSNNKYAASSYLSLTPEQWKSHRSY
SCQVTHEGSTVEKTVAPTECS

FIG. 2B

Nucleotide sequence of M43

M43 HC (SEQ ID NO: 21)

GAGGTGCAGCTGTTGGAGTCTGGGGGAGGCTTGGTACAGCCTGGGGGGTCCCTGAGACTCTCC
TGTGCAGCCTCTGGATTCACCTTTAGGAACTCTGCCATGAGCTGGGTCCGCCAGGCTCCAGGG
AAGGGGCTGGAGTGGGTCTCAGGTATTAGTGTTACTGGTGGTAGCACATTTTACACAGACTCC
GTGAAGGGCCGGTTCACCGTCTCCAGAGACAATTCCAGGAACACGCTGTATCTGCAAATGAAC
AGCCTGAGAGCCGAGGACACGGCCGTATATTACTGTGCGAAAGTCTACTACTATAGTTTCTTT
GACTACTGGGGCCAGGGAACCTTGGTCACCGTCTCTAGTGCCTCCACCAAGGGCCCATCGGTC
TTCCCCCTGGCGCCCTGCTCCAGGAGCACCTCCGAGAGCACAGCGGCCCTGGGCTGCCTGGTC
AAGGACTACTTCCCCGAACCGGTGACGGTGTCGTGGAACTCAGGCGCTCTGACCAGCGGCGTG
CACACCTTCCCAGCTGTCCTACAGTCCTCAGGACTCTACTCCCTCAGCAGCGTGGTGACCGTG
CCCTCCAGCAACTTCGGCACCCAGACCTACACCTGCAACGTAGATCACAAGCCCAGCAACACC
AAGGTGGACAAGACAGTTGAGCGCAAATGTTGTGTCGAGTGCTCACCGTGCCCAGCACCACCT
GTGGCAGGACCGTCAGTCTTCCTCTTCCCCCCAAAACCCAAGGACACCCTCATGATCTCCCGG
ACCCCTGAGGTCACGTGCGTGGTGGTGGACGTGAGCCACGAAGACCCCGAGGTCCAGTTCAAC
TGGTACGTGGACGGCGTGGAGGTGCATAATGCCAAGACAAAGCCACGGGAGGAGCAGTTCAAC
AGCACGTTCCGTGTGGTCAGCGTCCTCACCGTTGTGCACCAGGACTGGCTGAACGGCAAGGAG
TACAAGTGCAAGGTCTCCAACAAAGGCCTCCCAGCCCCCATCGAGAAAACCATCTCCAAAACC
AAAGGGCAGCCCCGAGAACCACAGGTGTACACCCTGCCCCCATCCCGGGAGGAGATGACCAAG
AACCAGGTCAGCCTGACCTGCCTGGTCAAAGGCTTCTACCCCAGCGACATCGCCGTGGAGTGG
GAGAGCAATGGGCAGCCGGAGAACAACTACAAGACCACACCTCCCATGCTGGACTCCGACGGC
TCCTTCTTCCTCTACAGCAAGCTCACCGTGGACAAGAGCAGGTGGCAGCAGGGGAACGTCTTC
TCATGCTCCGTGATGCATGAGGCTCTGCACAACCACTACACGCAGAAGAGCCTCTCCCTGTCT
CCGGGTAAA

M43 LC (SEQ ID NO: 22)

CAGACTGTGGTGACCCAGGAGCCAAGTTTCTCAGTGTCCCTGGAGGGACAGTCACACTCAC
TTGTGGCTTCAACTCTGGCTCAGTCTCTACTAGTTACTGGCCCAGCTGGTACCAACAGACCC
CAGGCCAGGCTCCACGCACGCTCATCTACAACACAAACACTCGCTCTTCTGGGGTCCCTGAT
CGCTTCTCTGGCTCCATCCTTGGGAACAAAGCTGCCCTCACCATCACGGGGGCCCAGGCAGA
TGATGAATCTGATTATTACTGTGTGCTGTGGATGGGTAGTGGCATTTGGGTGTTCGGCGGAG
GGACCAAGCTGACCGTCCTAGGTCAGCCCAAGGCCAACCCCACTGTCACTCTGTTCCCGCCC
TCCTCTGAGGAGCTCCAAGCCAACAAGGCCACACTAGTGTGTCTGATCAGTGACTTCTACCC
GGGAGCTGTGACAGTGGCCTGGAAGGCAGATGGCAGCCCCGTCAAGGCGGGAGTGGAGACCA
CCAAACCCTCCAAACAGAGCAACAACAAGTACGCGGCCAGCAGCTACCTGAGCCTGACGCCC
GAGCAGTGGAAGTCCCACAGAAGCTACAGCTGCCAGGTCACGCATGAAGGGAGCACCGTGGA
GAAGACAGTGGCCCCTACAGAATGTTCA

FIG. 2C

| Mutant ID | IgG ID | LC AA seq | HC AA seq |
|---|---|---|---|
| M10 | mmH29-LWT | QTVVTQEPSFSVSPGGTVTLTCGFNSGSVSTS YYPSWYQQTPGQAPRTLIYNTNTRSSGVPDRF SGSILGNKAALTITGAQADDESDYYCVLYMGS GIWVFGGGTKLTVLGQPKANPTVTLFPPSSEE LQANKATLVCLISDFYPGAVTVAWKADGSPVK AGVETTKPSKQSNNKYAASSYLSLTPEQWKSH RSYSCQVTHEGSTVEKTVAPTECS (SEQ ID NO: 25) | EVQLLESGGGLVQPGGSLRLSCAASGFTFRNDAMSWVRQAPGKGLEWVSGISVTGGS TFYTDSVKGRFTVSRDNSRNTLYLQMNSLRAEDTAVYYCAKVYYISFDYWGQGTLV TVSSASTKGPSVFPLAPCSRSTSESTAALGCLVKDYFPEPVTVSWNSGALTSGVHTF PAVLQSSGLYSLSSVVTVPSSNFGTQTYTCNVDHKPSNTKVDKTVERKCCVECPCP APPVAGPSVFLFPPKPKDTLMISRTPEVTCVVVDVSHEDPEVQFNWYVDGVEVHNAK TKPREEQFNSTFRVSVLTVVHQDWLNGKEYKCKVSNKGLPAPIEKTISKTKGQPRE PQVYTLPPSREEMTKNQVSLTCLVKGFYPSDIAVEWESNGQPENNYKTTPPMLDSDG SFFLYSKLTVDKSRWQQGNVFSCSVMHEALHNHYTQKSLSLSPGK (SEQ ID NO: 26) |
| M25 | mmH50-L3 | QTVVTQEPSFSVSPGGTVTLTCGFNSGSVSTS YYPSWYQQTPGQAPRTLIYNTNTRSSGVPDRF SGSILGNKAALTITGAQADDESDYYCVLYMGS GIWVFGGGTKLTVLGQPKANPTVTLFPPSSEE LQANKATLVCLISDFYPGAVTVAWKADGSPVK AGVETTKPSKQSNNKYAASSYLSLTPEQWKSH RSYSCQVTHEGSTVEKTVAPTECS (SEQ ID NO: 27) | EVQLLESGGGLVQPGGSLRLSCAASGFTFRNSAMSWVRQAPGKGLEWVSAISVTGGS TFYTDSVKGRFTVSRDNSRNTLYLQMNSLRAEDTAVYYCAKVYYISFDYWGQGTLV TVSSASTKGPSVFPLAPCSRSTSESTAALGCLVKDYFPEPVTVSWNSGALTSGVHTF PAVLQSSGLYSLSSVVTVPSSNFGTQTYTCNVDHKPSNTKVDKTVERKCCVECPCP APPVAGPSVFLFPPKPKDTLMISRTPEVTCVVVDVSHEDPEVQFNWYVDGVEVHNAK TKPREEQFNSTFRVSVLTVVHQDWLNGKEYKCKVSNKGLPAPIEKTISKTKGQPRE PQVYTLPPSREEMTKNQVSLTCLVKGFYPSDIAVEWESNGQPENNYKTTPPMLDSDG SFFLYSKLTVDKSRWQQGNVFSCSVMHEALHNHYTQKSLSLSPGK (SEQ ID NO: 28) |
| M37 | mmH59-L2 | QTVVTQEPSFSVSPGGTVTLTCGFNSGSVSTS YYPSWYQQTPGQAPRTLIYNTNTRSSGVPDRF SGSILGNKAALTITGAQADDESDYYCVLYMGS GIWVFGGGTKLTVLGQPKANPTVTLFPPSSEE LQANKATLVCLISDFYPGAVTVAWKADGSPVK AGVETTKPSKQSNNKYAASSYLSLTPEQWKSH RSYSCQVTHEGSTVEKTVAPTECS (SEQ ID NO: 29) | EVQLLESGGGLVQPGGSLRLSCAASGFTFRNXAMAWVRQAPGKGLEWVSISFDYWGQGTLV TFYTDSVKGRFTVSRDNSRNTLYLQMNSLRAEDTAVYYCAKVYYISFDYWGQGTLV TVSSASTKGPSVFPLAPCSRSTSESTAALGCLVKDYFPEPVTVSWNSGALTSGVHTF PAVLQSSGLYSLSSVVTVPSSNFGTQTYTCNVDHKPSNTKVDKTVERKCCVECPCP APPVAGPSVFLFPPKPKDTLMISRTPEVTCVVVDVSHEDPEVQFNWYVDGVEVHNAK TKPREEQFNSTFRVSVLTVVHQDWLNGKEYKCKVSNKGLPAPIEKTISKTKGQPRE PQVYTLPPSREEMTKNQVSLTCLVKGFYPSDIAVEWESNGQPENNYKTTPPMLDSDG SFFLYSKLTVDKSRWQQGNVFSCSVMHEALHNHYTQKSLSLSPGK (SEQ ID NO: 30) |
| M39 | mmH52-L3 | QTVVTQEPSFSVSPGGTVTLTCGFNSGSVSTS YYPSWYQQTPGQAPRTLIYNTNTRSSGVPDRF SGSILGNKAALTITGAQADDESDYYCVLYMGS GIHVFGGGTKLTVLGQPKANPTVTLFPPSSEE LQANKATLVCLISDFYPGAVTVAWKADGSPVK AGVETTKPSKQSNNKYAASSYLSLTPEQWKSH RSYSCQVTHEGSTVEKTVAPTECS (SEQ ID NO: 31) | EVQLLESGGGLVQPGGSLRLSCAASGFTFRNSAMSWVRQAPGKGLEWVSISFDYWGQGTLV TFYTDSVKGRFTVSRDNSRNTLYLQMNSLRAEDTAVYYCAKVYYISFDYWGQGTLV TVSSASTKGPSVFPLAPCSRSTSESTAALGCLVKDYFPEPVTVSWNSGALTSGVHTF PAVLQSSGLYSLSSVVTVPSSNFGTQTYTCNVDHKPSNTKVDKTVERKCCVECPCP APPVAGPSVFLFPPKPKDTLMISRTPEVTCVVVDVSHEDPEVQFNWYVDGVEVHNAK TKPREEQFNSTFRVSVLTVVHQDWLNGKEYKCKVSNKGLPAPIEKTISKTKGQPRE PQVYTLPPSREEMTKNQVSLTCLVKGFYPSDIAVEWESNGQPENNYKTTPPMLDSDG SFFLYSKLTVDKSRWQQGNVFSCSVMHEALHNHYTQKSLSLSPGK (SEQ ID NO: 32) |

FIG. 2D

| | Amino acid seq | Nucleotide seq |
|---|---|---|
| ActRIIB | MTAPWVALALLWGSLWPGSGRGEAE TRECIYYNANWELERTNQSGLERCE GEQDKRLHCYASWANSSGTIELVKK GCWLDDFNCYDRQECVATEENPQVY FCCCEGNFCNERFTHLPEAGGPEVT YEPPPTAPT<br><br>(SEQ ID NO: 2) | ATGACGGCGCCCTGGGTGGCCCTCGCCCTCCT CTGGGGATCGCTGTGGCCCGGCTCTGGGCGTG GGGAGGCTGAGACACGGGAGTGCATCTACTAC AACGCCAACTGGGAGCTGGAGCGCACCAACCA GAGCGGCCTGGAGCGCTGCGAAGGCGAGCAGG ACAAGCGGCTGCACTGCTACGCCTCCTGGGCC AACAGCTCTGGCACCATCGAGCTCGTGAAGAA GGGCTGCTGGCTAGATGACTTCAACTGCTACG ATAGGCAGGAGTGTGTGGCCACTGAGGAGAAC CCCCAGGTGTACTTCTGCTGCTGTGAAGGCAA CTTCTGCAACGAGCGCTTCACTCATTTGCCAG AGGCTGGGGGCCCGGAAGTCACGTACGAGCCA CCCCCGACAGCCCCCACC<br><br>(SEQ ID NO: 20) |
| ActRIIB-huFc | MTAPWVALALLWGSLWPGSGRGEAE TRECIYYNANWELERTNQSGLERCE GEQDKRLHCYASWANSSGTIELVKK GCWLDDFNCYDRQECVATEENPQVY FCCCEGNFCNERFTHLPEAGGPEVT YEPPPTAPTVDKTHTCPPCPAPELL GGPSVFLFPPKPKDTLMISRTPEVT CVVVDVSHEDPEVKFNWYVDGVEVH NAKTKPREEQYNSTYRVVSVLTVLH QDWLNGKEYKCKVSNKALPAPIEKT ISKAKGQPREPQVYTLPPSRDELTK NQVSLTCLVKGFYPSDIAVEWESNG QPENNYKTTPPVLDSDGSFFLYSKL TVDKSRWQQGNVFSCSVMHEALHNH YTQKSLSLSPGK<br><br>(SEQ ID NO: 1) | ATGACGGCGCCCTGGGTGGCCCTCGCCCTCCT CTGGGGATCGCTGTGGCCCGGCTCTGGGCGTG GGGAGGCTGAGACACGGGAGTGCATCTACTAC AACGCCAACTGGGAGCTGGAGCGCACCAACCA GAGCGGCCTGGAGCGCTGCGAAGGCGAGCAGG ACAAGCGGCTGCACTGCTACGCCTCCTGGGCC AACAGCTCTGGCACCATCGAGCTCGTGAAGAA GGGCTGCTGGCTAGATGACTTCAACTGCTACG ATAGGCAGGAGTGTGTGGCCACTGAGGAGAAC CCCCAGGTGTACTTCTGCTGCTGTGAAGGCAA CTTCTGCAACGAGCGCTTCACTCATTTGCCAG AGGCTGGGGGCCCGGAAGTCACGTACGAGCCA CCCCCGACAGCCCCCACCGTCGACAAAACTCA CACATGCCCACCGTGCCCAGCACCTGAACTCC TGGGGGGACCGTCAGTCTTCCTCTTCCCCCCA AAACCCAAGGACACCCTCATGATCTCCCGGAC CCCTGAGGTCACATGCGTGGTGGTGGACGTGA GCCACGAAGACCCTGAGGTCAAGTTCAACTGG TACGTGGACGGCGTGGAGGTGCATAATGCCAA GACAAAGCCGCGGGAGGAGCAGTACAACAGCA CGTACCGTGTGGTCAGCGTCCTCACCGTCCTG CACCAGGACTGGCTGAATGGCAAGGAGTACAA GTGCAAGGTCTCCAACAAAGCCCTCCCAGCCC CCATCGAGAAAACCATCTCCAAAGCCAAAGGG CAGCCCCGAGAACCACAGGTGTACACCCTGCC CCCATCCCGGGATGAGCTGACCAAGAACCAGG TCAGCCTGACCTGCCTGGTCAAAGGCTTCTAT CCCAGCGACATCGCCGTGGAGTGGGAGAGCAA TGGGCAGCCGGAGAACAACTACAAGACCACGC CTCCCGTGCTGGACTCCGACGGCTCCTTCTTC CTCTACAGCAAGCTCACCGTGGACAAGAGCAG GTGGCAGCAGGGGAACGTCTTCTCATGCTCCG TGATGCATGAGGCTCTGCACAACCACTACACG CAGAAGAGCCTCTCCCTGTCTCCGGGTAAA<br><br>(SEQ ID NO: 24) |

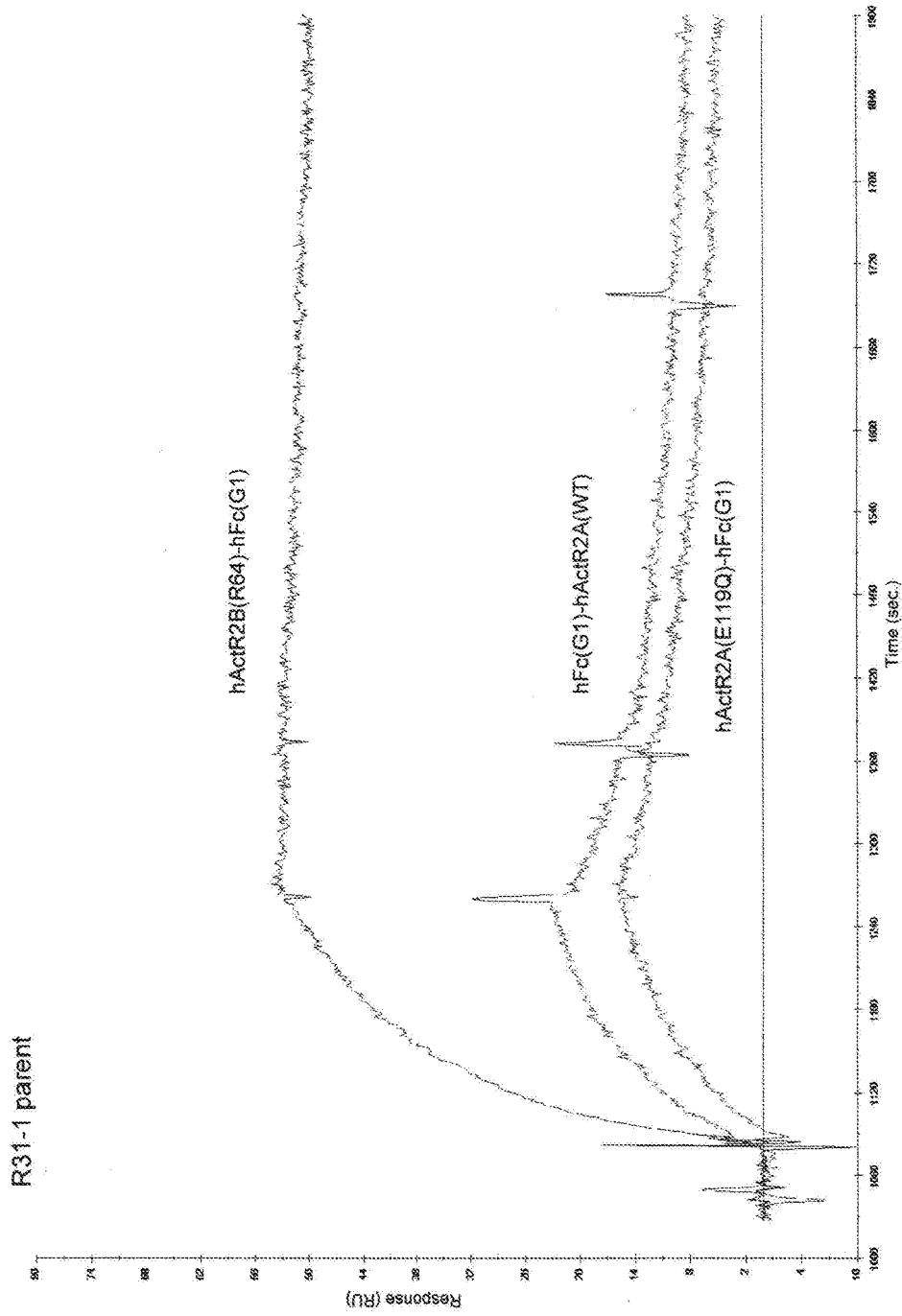

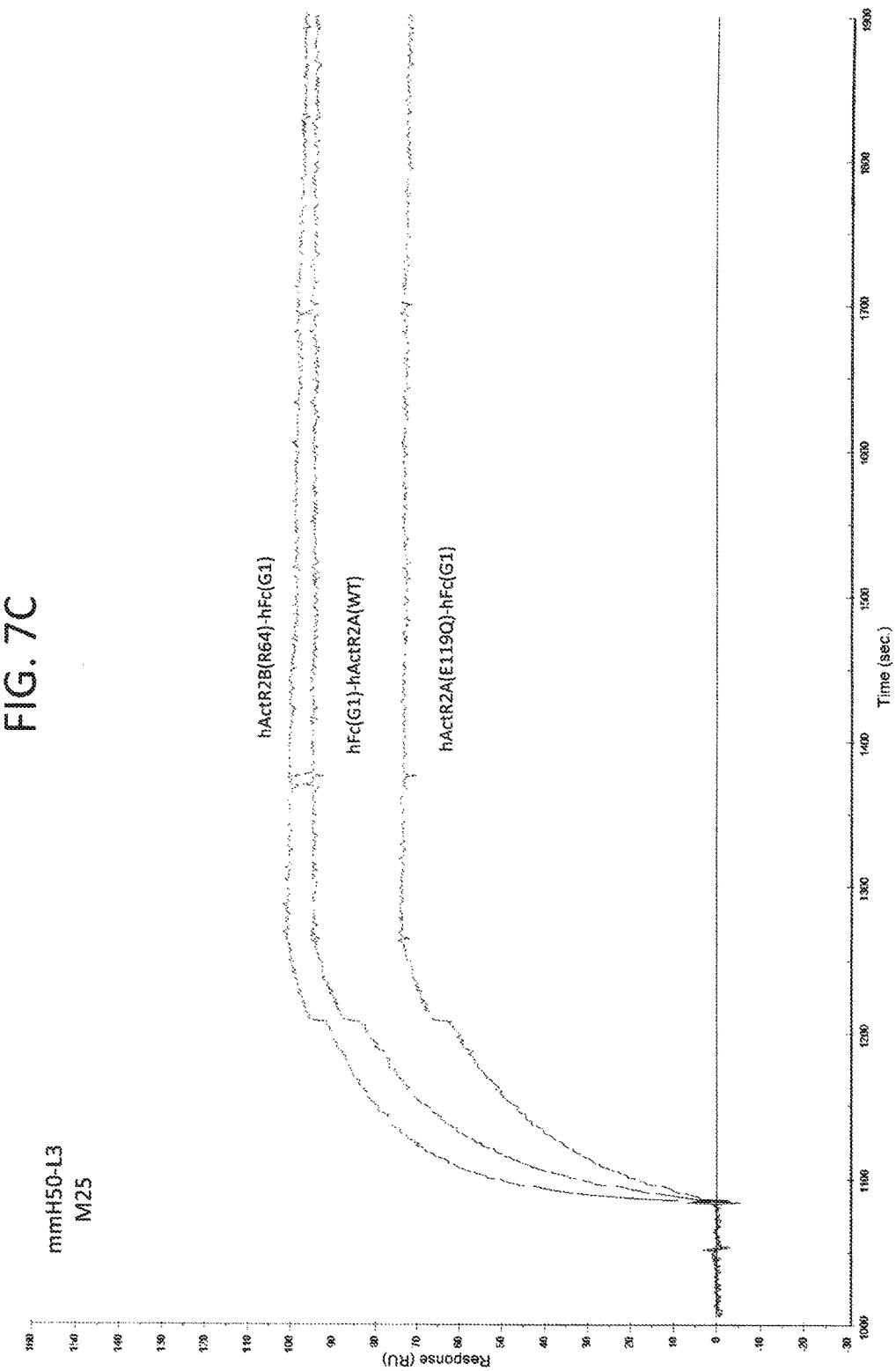

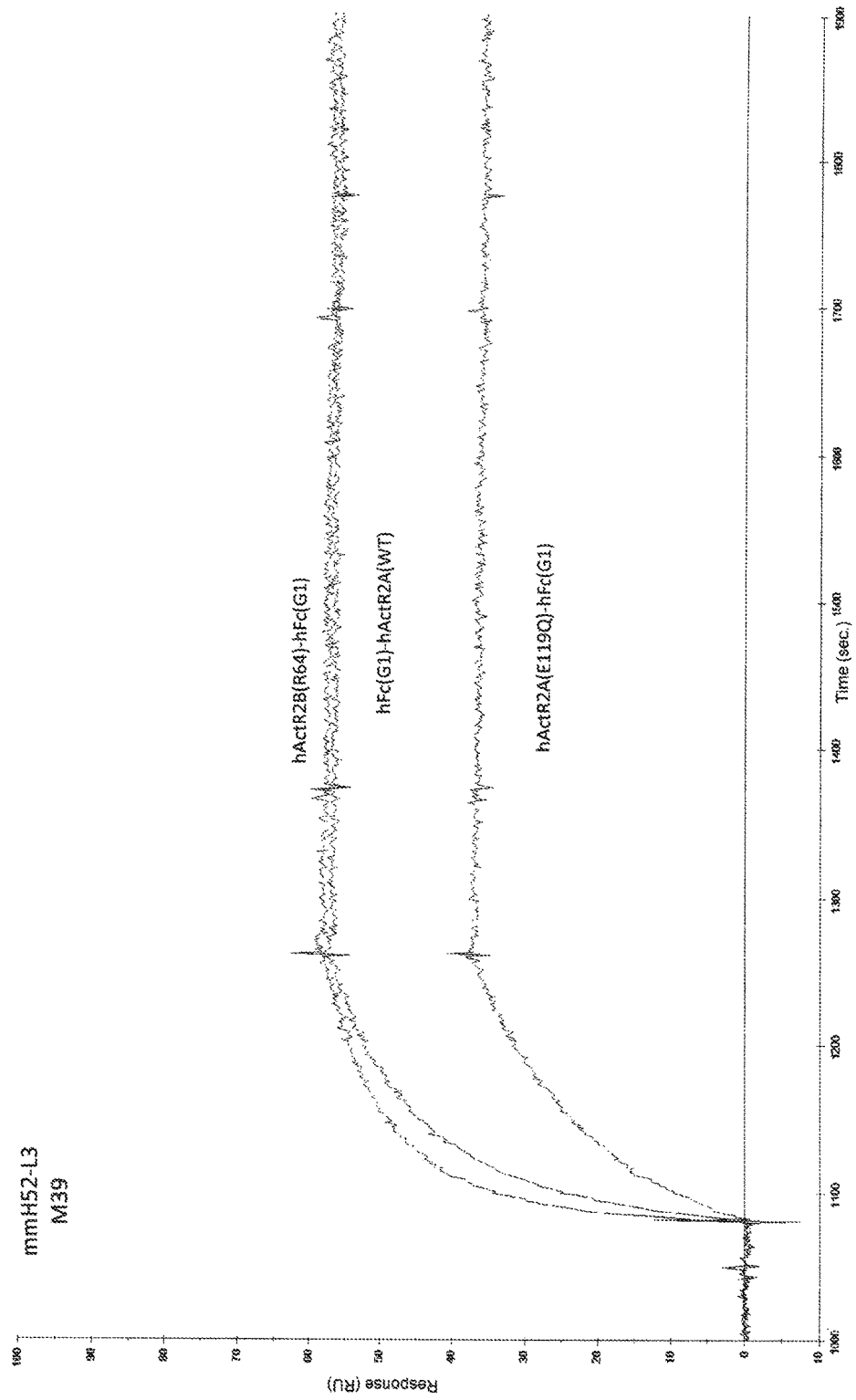

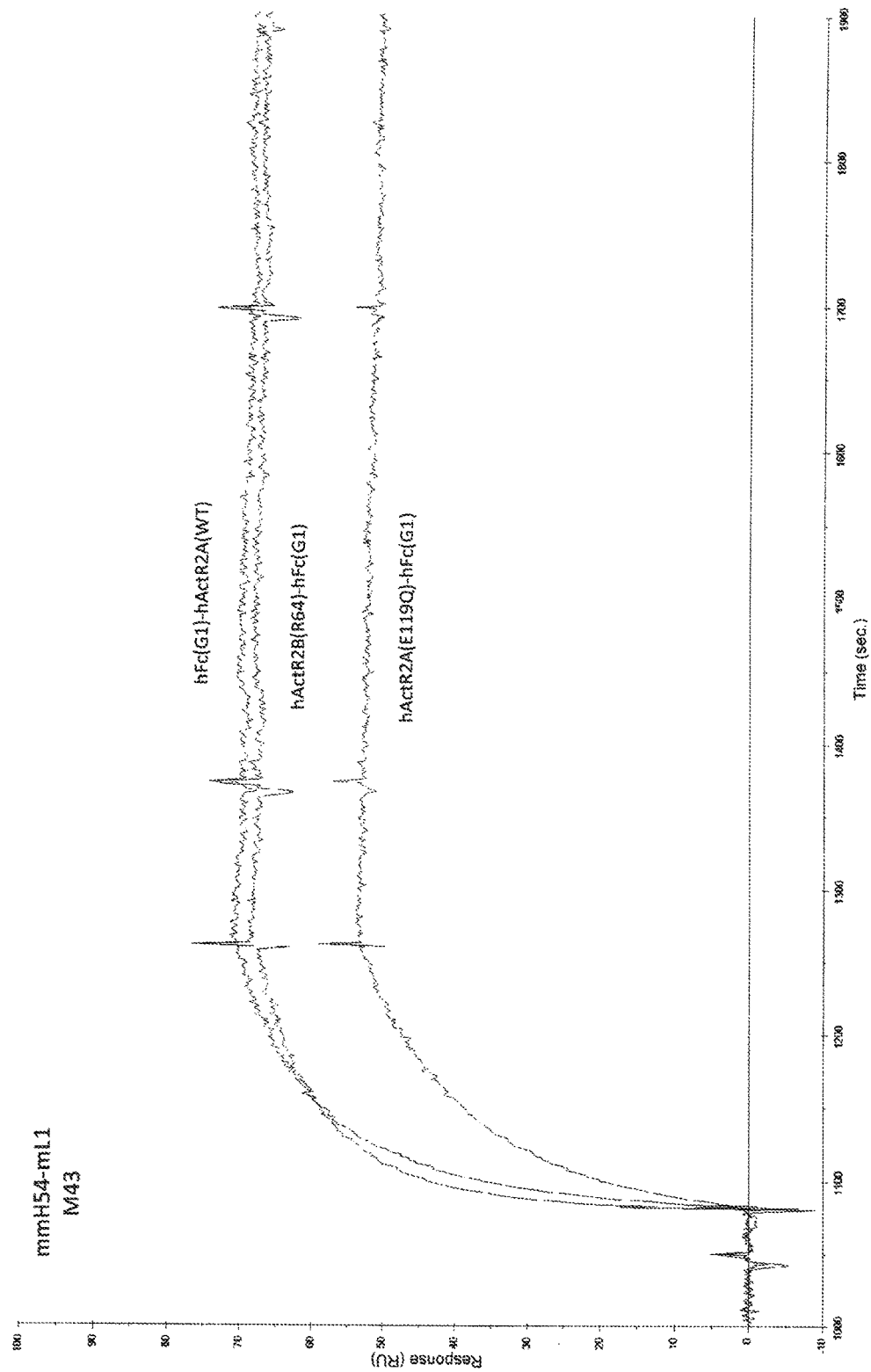

DUAL RECEPTOR ANTAGONISTIC ANTIGEN-BINDING PROTEINS AND USES THEREOF

CROSS REFERENCE TO RELATED APPLICATIONS

This application is a continuation of U.S. application Ser. No. 14/407,421, with a 371(c) filing date of Dec. 11, 2014 (pending), which is a 371 national phase application of International Application No. PCT/US2013/045245, filed Jun. 11, 2013, which claims the benefit of U.S. Provisional Application No. 61/658,237, filed Jun. 11, 2012, the entire disclosures of which are hereby incorporated by reference in their entirety for all purposes.

STATEMENT REGARDING FEDERALLY SPONSORED RESEARCH OR DEVELOPMENT

Not applicable.

REFERENCE TO A SEQUENCE LISTING

The instant application contains a Sequence Listing with 33 sequences which has been submitted via EFS-Web and is hereby incorporated by reference in its entirety. Said ASCII copy, created on Jul. 12, 2016, is named 34107 US_CRF_sequencelisting.txt, and is 57,344 bytes in size.

FIELD OF THE INVENTION

This disclosure relates to antagonistic dual receptor antigen-binding proteins, e.g. antibodies and methods of using the dual receptor antibodies. The dual receptor antibodies may comprise antibodies to ActRII receptors and may be used to stimulate muscle growth.

BACKGROUND OF THE INVENTION

The transforming growth factor .beta. (TGF-.beta.) family of proteins includes the transforming growth factors-.beta. (TGF-.beta.), activins, bone morphogenic proteins (BMP), nerve growth factors (NGFs), brain-derived neurotrophic factor (BDNF), and growth/differentiation factors (GDFs). These family members are involved in the regulation of a wide range of biological processes including cell proliferation, differentiation, and other functions.

Growth/differentiation factor 8 (GDF-8), also referred to as myostatin, is a TGF-.beta. family member expressed for the most part in the cells of developing and adult skeletal muscle tissue. Myostatin appears to play an essential role in negatively controlling skeletal muscle growth (McPherron et al., Nature (London), 387:83-90, (1997); Zimmers et al., Science, 296:1486-1488, (2002)). Antagonizing myostatin has been shown to increase lean muscle mass in animals.

Another member of the TGF-.beta. family of proteins is a related growth/differentiation factor, growth/differentiation factor 11 (GDF-11). GDF-11 has approximately 90 sequence identity to the amino acid sequence of myostatin. GDF-11 has a role in the axial patterning in developing animals (Oh et al., Genes Dev., 11:1812-26, (1997)), and also appears to play a role in skeletal muscle development and growth.

Activins A, B and AB are the homodimers and heterodimer respectively of two polypeptide chains, .beta.A and .beta.B (Vale et al., Nature, 321:776-779, (1986); Ling et al., Nature, 321:779-782, (1986)). Activins were originally discovered as gonadal peptides involved in the regulation of follicle stimulating hormone synthesis, and are now believed to be involved in the regulation of a number of biological activities. Activin A is a predominant form of activin.

Activin, myostatin, GDF-11 and other members of the TGF-.beta. superfamily bind and signal through a combination of activin type IIA (ActRIIA) and activin type IIB (ActRIIB) receptors, both of which are transmembrane serine/threonine kinases (Harrison et al., J. Biol. Chem., 279:28036-28044, (2004)). Cross-linking studies have determined that myostatin is capable of binding the activin type II receptors ActRIIA and ActRIIB in vitro (Lee et al., PNAS USA, 98:9306-11, (2001)). There is also evidence that GDF-11 binds to both ActRIIA and ActRIIB (Oh et al., Genes Dev., 16:2749-54, (2002)).

ActRIIB polypeptides can be prepared as a soluble variant of ActRIIB-Fc. Soluble ActRIIB-Fc potently stimulates muscle growth by sequestering multiple ligands such as myostatin, activin and GDF11 (Lee S J, et al., Proc Natl Acad Sci USA., 102(50):18117-22, (2005 Dec. 13) (Epub. 2005 Dec. 5)). These ligands, including myostatin, bind to two high affinity receptors, ActRIIB and ActRIIA. These two receptors are encoded by two different genes, which encode two distinct transmembrane receptor proteins with about 65% sequence homology at the amino acid level. Ligand binding at the cell membrane to either of these two receptors has been shown to cause the phosphorylation of Smads 2/3 and, as a result, to activate downstream transcriptional changes in the cell, (Lee S J, et al., Proc Natl Acad Sci USA., 102(50):18117-22, (2005 Dec. 13) (Epub. 2005 Dec. 5)). Skeletal muscle cells express both of these receptors. Interfering with the activin receptors, e.g. by using an antagonistic dual receptor antibody can result in physiological effects by blocking the activin signaling pathway.

The present invention provides a biologically active therapeutic that blocks at least activin activity and is thereby capable of stimulating skeletal muscle growth.

SUMMARY OF THE INVENTION

The invention relates to antagonistic dual activin receptor antigen-binding proteins and fragments thereof that bind to ActRII receptors. In various embodiments the antigen-binding proteins are antibodies. The antibodies can bind ActRIIA and ActRIIB. Uses are provided for the antigen-binding proteins described herein, e.g. stimulation of skeletal muscle growth.

In various embodiments an isolated antigen-binding protein that binds two activin receptors is provided. The antigen binding protein can bind two activin receptors at the same time. The isolated antigen-binding protein specifically binds to SEQ ID NO: 2 and SEQ ID NO: 18. Alternatively, the isolated antigen-binding protein specifically binds to SEQ ID NO: 1 and SEQ ID NO: 17. In various aspects, when the antigen binding protein binds to SEQ ID NO: 2 and SEQ ID NO: 18 or to SEQ ID NO: 1 and SEQ ID NO: 17 it stimulates muscle growth. In other aspects, the antigen-binding protein is a monoclonal antibody or fragment thereof. The can be a mouse antibody, a humanized antibody, a human antibody, a chimeric antibody, a multispecific antibody, or fragment of a mouse antibody, a chimeric antibody or a multispecific antibody.

In various embodiments an isolated antigen-binding protein comprising SEQ ID NO: 15 and SEQ ID NO: 16 is provided. In various aspects the isolated antigen-binding protein can have 97% identity to SEQ ID NOs: 15 and 16. The isolated antigen-binding protein can bind to SEQ ID NO: 2 and SEQ ID NO: 18. In various aspects, when the antigen-binding protein binds to SEQ ID NO: 2 and SEQ ID NO: 18 it stimulates muscle growth. In other aspects, the antigen-binding protein is a monoclonal antibody or fragment thereof. The antibody can be a mouse antibody, a humanized antibody, a human antibody, a chimeric antibody, a multispecific antibody, or fragment of a mouse antibody, a chimeric antibody or a multispecific antibody.

In various embodiments an isolated antigen-binding protein comprising SEQ ID NO: 3, SEQ ID NO: 4, SEQ ID NO: 5, SEQ ID NO: 6, SEQ ID NO: 7 and SEQ ID NO: 8 is provided. The isolated antigen-binding protein can specifically bind to SEQ ID NO: 2 and SEQ ID NO: 18. When the antigen-binding protein binds to both SEQ ID NO: 2 and SEQ ID NO: 18 it can stimulate muscle growth. In other aspects, the antigen-binding protein is a monoclonal antibody or fragment thereof. The antibody can be a mouse antibody, a humanized antibody, a human antibody, a chimeric antibody, a multispecific antibody, or fragment of a mouse antibody, a chimeric antibody or a multispecific antibody.

In various embodiments an isolated antigen-binding protein comprising SEQ ID NO: 3, SEQ ID NO: 4, SEQ ID NO: 5. The isolated antigen-binding protein can bind to SEQ ID NO: 2 and SEQ ID NO: 18. In various aspects, when the antigen-binding protein binds to SEQ ID NO: 2 and SEQ ID NO: 18 it stimulates muscle growth. In other aspects, the antigen-binding protein is a monoclonal antibody or fragment thereof. The antibody can be a mouse antibody, a humanized antibody, a human antibody, a chimeric antibody, a multispecific antibody, or fragment of a mouse antibody, a chimeric antibody or a multispecific antibody.

In various embodiments an isolated antigen-binding protein comprising SEQ ID NO: 6, SEQ ID NO: 7 and SEQ ID NO: 8 is provided. The isolated antigen-binding protein can bind to SEQ ID NO: 2 and SEQ ID NO: 18. In various aspects, when the antigen-binding protein binds to both SEQ ID NO: 2 and SEQ ID NO: 18 it stimulates muscle growth. In other aspects, the antigen-binding protein is a monoclonal antibody or fragment thereof. The antibody can be a mouse antibody, a humanized antibody, a human antibody, a chimeric antibody, a multispecific antibody, or fragment of a mouse antibody, a chimeric antibody or a multispecific antibody.

In various embodiments an isolated nucleic acid encoding any of the antigen-binding proteins is provided. An expression vector comprising the nucleic acid and a host cell is also provided. The host cell can be a eukaryotic or prokaryotic cell. The eukaryotic cell can be a mammalian cell.

In various embodiments, an isolated antigen-binding protein, comprising at least SEQ ID NOs: 3-5 or SEQ ID NOs: 4-6 is provided. In various aspects, a method of producing an antigen-binding protein, comprising culturing the host cell under suitable conditions such that the nucleic acid is expressed to produce the antibody. The antibody can be recovered from the culture of the host cell.

In various embodiments a composition comprising an antigen-binding protein of and a pharmaceutically acceptable carrier, diluent or excipient is provided.

In other embodiments, a method of reducing or blocking myostatin, activin A or GDF-11 activity is provided comprising administering a therapeutically effective amount of the antigen-binding protein or a pharmaceutical composition containing the antigen binding protein to a subject in need of such treatment.

In yet other embodiments, a method of increasing lean muscle mass or increasing the ratio of lean muscle mass to fat mass in a subject in need of such treatment is provided comprising administering an effective amount the antigen-binding protein or a pharmaceutical composition containing the antigen binding protein.

In various embodiments, a method of treating or preventing a muscle wasting disease in a subject suffering from such a disorder is provided comprising administering an effective amount of a therapeutic composition containing the antigen-binding protein to the subject. The muscle wasting disease can comprise cancer cachexia, muscular dystrophy, amyotrophic lateral sclerosis, congestive obstructive pulmonary disease, chronic heart failure, chemical cachexia, cachexia from HIV/AIDS, renal failure, uremia, rheumatoid arthritis, age-related sarcopenia, age-related frailty, organ atrophy, carpal tunnel syndrome, androgen deprivation, or muscle-wasting due to inactivity from prolonged bed rest, spinal cord injury, stroke, bone fracture, burns, aging or insulin resistance.

In various embodiments, an isolated antigen-binding protein is provided wherein the isolated antigen-binding protein has a $K_D$ for ActRIIB of 10 pM or less in a BIAcore assay. In other aspects, the antigen-binding protein can have a $K_D$ for ActRIIB of 1 pM or less. In yet other aspects, the isolated antigen-binding protein has a $K_D$ for ActRIIA of 4 nM or less in a BIAcore assay. The antigen-binding protein can also have a $K_D$ for ActRIIA of 1 pM or less.

In other aspects, the antigen-binding protein can have a KD for both ActRIIB and ActRIIA of 1 pM or less in a BIAcore assay.

In various embodiments, an isolated antigen-binding protein is provided wherein the isolated antigen-binding protein has a $IC_{50}$ for ActRIIB of 8 nm or less in a cell-based assay. In other aspects, the antigen-binding protein can have an $C_{50}$ for ActRIIB of 2 nM or less. In yet other aspects, the isolated antigen-binding protein can have an $IC_{50}$ for ActRIIA of 2 nM or less in a cell-based assay. The antigen binding protein can also have an $IC_{50}$ for ActRIIA of 1 nM or less. The antigen-binding protein can have an $IC_{50}$ for ActRIIB of 2 nM or less and an $IC_{50}$ActRIIA of 1 nM or less in a cell-based assay.

In various embodiments, the antigen-binding protein is an antagonistic dual-receptor antibody. The dual-receptor antibody can be a human antibody.

In various embodiments, a method of reducing or blocking myostatin, activin A or GDF-11 activity is provided comprising administering dual receptor antigen-binding proteins or polypeptides, or pharmaceutical compositions containing these, to a subject in need of such treatment. The antigen-binding proteins can be antagonistic dual receptor antibodies. The antibodies can be against ActRIIB and ActRIIA.

In another aspect, a method of increasing lean muscle mass or increasing the ratio of lean muscle mass to fat mass in a subject in need of such treatment is provided comprising administering an effective amount of the composition or pharmaceutical composition containing dual receptor antigen-binding proteins or polypeptides to the subject. The antigen-binding proteins can be antagonistic dual receptor antibodies. The antibodies can be against ActRIIB and ActRIIA.

In another aspect, a method of treating or preventing a muscle wasting disease in a subject suffering from such a disorder is provided comprising administering a therapeutic composition containing dual receptor antigen-binding proteins or polypeptides to the subject. The antigen-binding proteins can be antagonistic dual receptor antibodies. The antibodies can be against ActRIIB and ActRIIA. The muscle wasting disease includes, but is not limited to, the following conditions: cancer cachexia, muscular dystrophy, amyotrophic lateral sclerosis, congestive obstructive pulmonary disease, chronic heart failure, chemical cachexia, cachexia from HIV/AIDS, renal failure, uremia, rheumatoid arthritis, age-related sarcopenia, age-related frailty, organ atrophy, carpal tunnel syndrome, androgen deprivation, and muscle-wasting due to inactivity from prolonged bed rest, spinal cord injury, stroke, bone fracture, burns, aging, insulin resistance, and other disorders. The muscle wasting may also result from weightlessness due to space flight. The antigen-binding proteins can be antagonistic dual receptor antibodies. The antibodies can be against ActRIIB and ActRIIA.

In another aspect, a method of treating conditions in which activin is overexpressed in a subject in need of such treatment is provided comprising, administering an effective amount of a therapeutic composition containing a dual activin receptor antigen-binding protein or polypeptides to the subject. In one embodiment, the disease is cancer. In another aspect, the present invention provides a method of treating a metabolic disorder comprising administering a therapeutic composition containing antigen-binding proteins or polypeptides to a subject in need of such treatment, wherein the metabolic disorder is selected from bone loss, diabetes, obesity, impaired glucose tolerance, hyperglycemia, and metabolic syndrome.

BRIEF DESCRIPTION OF THE DRAWINGS

FIG. 1 shows the CDR amino acid sequences for the HC and LC of antibodies M43 (SEQ ID NOs: 3-8) and R31-1 (SEQ ID NOs: 9-14).

FIG. 2A shows the amino acid sequences of M43 HC (SEQ ID NO: 15) and LC (SEQ ID NO: 16). Bold face letters represent the CDR regions. Underlined letters represent the amino acid differences from the R31-1. FIG. 2B shows the nucleic acid sequences of M43 HC (SEQ ID NO: 21) and M43 LC (SEQ ID NO: 22). FIG. 2C provides sequences for additional antibodies of the application. Bold face letters represent the CDR regions. Underlined letters represent the amino acid differences from the R31-1. FIG. 2D provides the amino acid and nucleic acid sequences for ActRIIB (SEQ ID NOs: 2 and 20) and ActRIIB-huFc (SEQ ID NOs: 1 and 24)

FIG. 7A, FIG. 7B, FIG. 7C, FIG. 7D, FIG. 7E, and FIG. 7F each show the huActRIIB and huActRIIA binding comparison of the one of 6 (parent and 5 mutant) antibodies.

DETAILED DESCRIPTION

Figure 3:
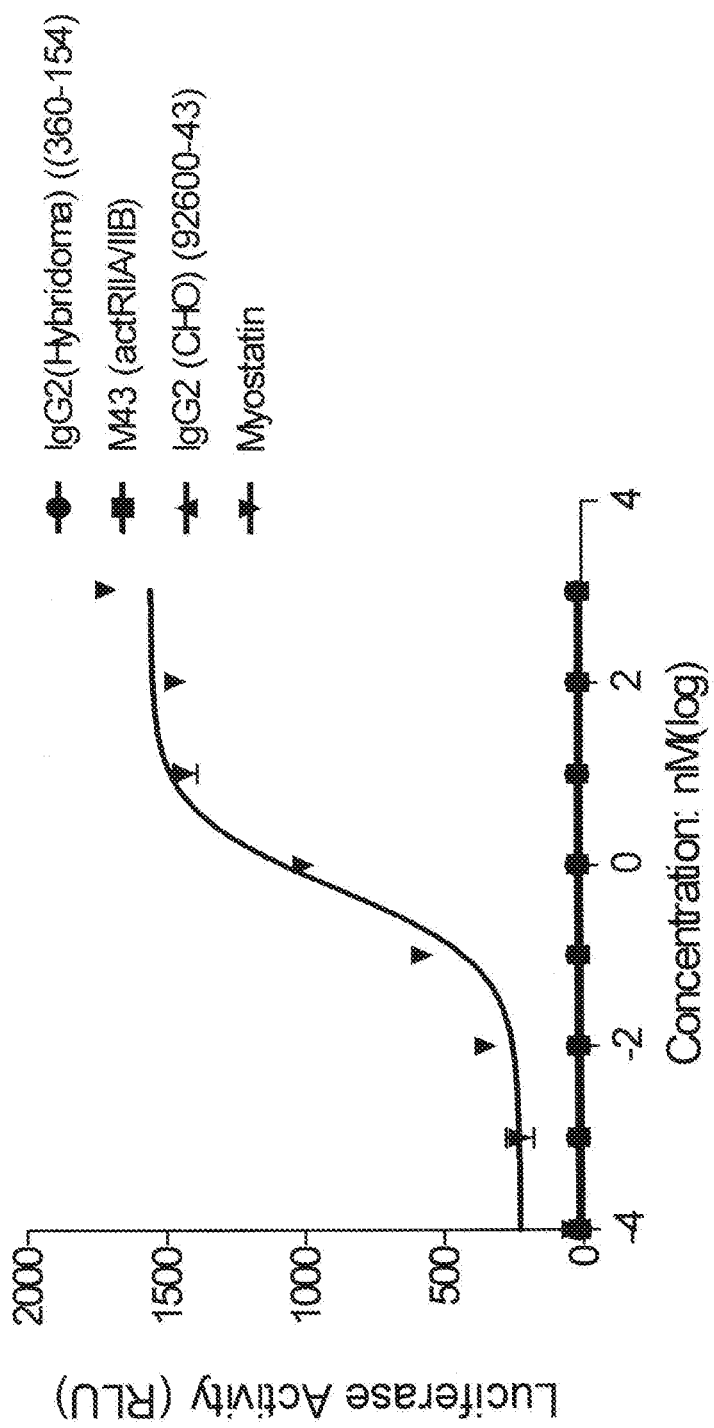
FIG. 3 shows lack of agonistic activity for M43 in a cell-based assay.

Dual receptor antagonistic antigen-binding proteins (such as antibodies and functional binding fragments thereof) that bind to ActRII receptors are disclosed herein. In some embodiments, the ActRII receptors are ActRIIA and ActRIIB receptors. The antigen-binding proteins bind to activin receptors and prevent the activin receptors from functioning in various ways. For example, the dual receptor binding proteins may bind to the activin receptors, prevent activin binding to the receptors and produce a physiological effect, e.g. stimulate skeletal muscle growth.

The foregoing summary is not intended to define every aspect or embodiment of the invention, and additional aspects may be described in other sections. The entire document is intended to be related as a unified disclosure, and it should be understood that all combinations of features described herein may be contemplated, even if the combination of features is not found together in the same sentence, or paragraph, or section of this document.

In addition to the foregoing, as an additional aspect, all embodiments narrower in scope in any way than the variations defined by specific paragraphs herein can be included in this disclosure. For example, certain aspects are described as a genus, and it should be understood that every member of a genus can be, individually, an embodiment. Also, aspects described as a genus or selecting a member of a genus should be understood to embrace combinations of two or more members of the genus. It should also be understood that while various embodiments in the specification are presented using "comprising" language, under various circumstances, a related embodiment may also be described using "consisting of" or "consisting essentially of" language.

It will be understood that the descriptions herein are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

It should also be understood that when describing a range of values, the characteristic being described could be an individual value found within the range. For example, "a pH from about pH 4 to about pH 6," could be, but is not limited to, pH 4, 4.2, 4.6, 5.1, 5.5, etc. and any value in between such values. Additionally, "a pH from about pH 4 to about pH 6," should not be construed to mean that the pH in question varies 2 pH units from pH 4 to pH 6, but rather a value may be picked from within a two pH range for the pH of the solution.

In some embodiments, when the term "about" is used, it means the recited number plus or minus 5%, 10%, 15% or more of that recited number. The actual variation intended is determinable from the context.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. As utilized in accordance with the disclosure, the following terms, unless otherwise indicated, shall be understood to have the following meanings:

As used herein the term "TGF-.beta. family members" or "TGF-.beta. proteins" refers to the structurally related growth factors of the transforming growth factor family including activins, and growth and differential factor (GDF) proteins (Kingsley et al., Genes Dev., 8:133-146, (1994); McPherron et al. Growth factors and cytokines in health and disease, Vol. 1B, D. LeRoith and C. Bondy. ed., JAI Press Inc., Greenwich, Conn., USA, pp 357-393).

GDF-8, also referred to as myostatin, is a negative regulator of skeletal muscle tissue (McPherron et al., PNAS USA, 94:12457-12461, (1997)). Myostatin is synthesized as an inactive protein complex approximately 375 amino acids in length, having GenBank Accession No: AAB86694 for human. The precursor protein is activated by proteolytic cleavage at a tetrabasic processing site to produce an N-terminal inactive prodomain and an approximately 109 amino acid C-terminal protein which dimerizes to form a homodimer of about 25 kDa. This homodimer is the mature, biologically active protein (Zimmers et al., Science, 296: 1486 (2002)).

As used herein GDF-11 refers to the BMP (bone morphogenic protein) having Swissprot accession number 095390 (SEQ ID NO: 50), as well as variants and species homologs of that protein. GDF-11 has approximately 90% identity to myostatin at the amino acid level. GDF-11 is involved in the regulation of anterior/posterior patterning of the axial skeleton (McPherron, et al., Nature Genet., 22(93): 260-264, (1999); Gamer, et al., Dev. Biol., 208(1):222-232, (1999)) but postnatal functions are unknown.

As used herein the term "derivative of the ActRIIA and ActRIIB polypeptides" refers to the attachment of at least one additional chemical moiety, or at least one additional polypeptide to form covalent or aggregate conjugates such as glycosyl groups, lipids, acetyl groups, or C-terminal or N-terminal fusion polypeptides, conjugation to PEG molecules, and other modifications which are described more fully below. Variant ActRIIB receptor polypeptides (vActRIIB) can also include additional modifications and derivatives, including modifications to the C and N termini which arise from processing due to expression in various cell types such as mammalian cells, E. coli, yeasts and other recombinant host cells. Further included are vActRIIB polypeptide fragments and polypeptides comprising inactivated N-glycosylation site(s), inactivated protease processing site(s), or conservative amino acid substitution(s), As used herein, an antibody or antigen-binding fragment can be an agonist or an antagonist.

An "agonist" refers to an agent that binds to a polypeptide (such as a receptor), or a polynucleotide and stimulates, increases, activates, facilitates, enhances activation, sensitizes or up regulates the activity or expression of the polypeptide or polynucleotide.

An "antagonist" refers to an agent that inhibits expression of a polypeptide or polynucleotide or binds to, partially or totally blocking stimulation, decreases, prevents, delays activation, inactivates, desensitizes, or down regulates the activity of the polypeptide or polynucleotide.

An "antigen binding protein" ("ABP") refers to any protein that binds a specified target antigen. In this specification, the specified target antigen can be an activin receptor or fragment or region thereof, e.g. ActRIIA, ActRIIB, ActRIIA-huFc or ActRIIB-huFc. "Antigen-binding protein" includes but is not limited to antibodies and binding parts thereof, such as immunologically functional fragments. Peptibodies are another example of antigen-binding proteins.

A "dual receptor antigen-binding protein" refers to a protein that can bind two receptors. The binding can be at the same time or simultaneously or alternatively can be either of the receptors but not at the same time. The "dual receptor antigen-binding protein" can be a "dual receptor antagonistic antibody" that binds the two receptors. The receptors can be myostatin/activin receptors or the receptors can be ActRIIA and ActRIIB or ActRIIA-huFc and ActRIIB-huFc. The dual receptor antibody can block the signaling in parallel of both ActRIIB and ActRIIA. Blocking the signaling can have a physiological response, e.g. stimulating skeletal muscle or bone growth.

The term "polynucleotide" or "nucleic acid" includes both single-stranded and double-stranded nucleotide polymers. Nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The term "oligonucleotide" means a polynucleotide comprising 200 or fewer nucleotides. In some embodiments, oligonucleotides are about 10 to about 60 bases in length. In other embodiments, oligonucleotides are about 12, about 13, about 14, about 15, about 16, about 17, about 18, about 19, or about 20 to about 40 nucleotides in length. Oligonucleotides can be single stranded or double stranded, e.g., for use in the construction of a mutant gene. Oligonucleotides can be sense or antisense oligonucleotides. An oligonucleotide can include a label, including a radiolabel, a fluorescent label, a hapten or an antigenic label, for detection assays. Oligonucleotides can be used, for example, as PCR primers, cloning primers or hybridization probes.

An "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences can include, in addition to the specified sequences, coding sequences for up to ten or even up to twenty other proteins or portions thereof, or can include operably linked regulatory sequences that control expression of the coding region of the recited nucleic acid sequences, and/or can include vector sequences.

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

An isolated nucleic acid can encode antigen-binding proteins disclosed in various embodiments herein, e.g. a dual receptor antigen-binding protein or anti-activin dual receptor antibody. The nucleic acid is said to be "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "amino acid" refers to natural and/or non-naturally occurring amino acids, and includes its normal meaning in the art.

The terms "polypeptide" or "protein" means a macromolecule having the amino acid sequence of a native protein, i.e., a protein produced by a naturally-occurring and non-recombinant cell; or the protein can be produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally-occurring amino acid and polymers. The terms "polypeptide" and "protein" specifically encompass inter alia, activin dual receptor antigen-binding proteins, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. In various embodiments, fragments can be about five to about 500 amino acids long. For example, fragments can be at least about 5, about 6, about 8, about 10, about 14, about 20, about 50, about 70, about 100, about 150, about 200, about 250, about 300, about 350, about 400, or about 450 amino acids long. Useful polypeptide fragments include immunologically functional fragments of antibodies, including binding domains. In the case of an dual activin receptor-binding antibody, useful fragments include but are not limited to a CDR region, a variable domain of a heavy and/or light chain, a portion of an antibody chain or just its variable region including one, two, three, four, five or six CDRs, and the like.

The term "isolated protein" means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or non-covalent interaction) with a polypeptide with which it is not associated in nature, or (6) does not occur in nature. Typically, an "isolated protein" constitutes at least about 5%, at least about 10%, at least about 25%, or at least about 50%, at least about 75%, at least about 90% or more of a given sample. Genomic DNA, cDNA, mRNA or other RNA, of synthetic origin, or any combination thereof can encode such an isolated protein. In various embodiments, the isolated protein is substantially free from proteins or polypeptides or other contaminants that are found in its natural environment that would interfere with its therapeutic, diagnostic, prophylactic, research or other use.

A "variant" of a polypeptide (e.g., an antigen-binding protein, or an antibody) comprises an amino acid sequence wherein one or more amino acid residues are inserted into, deleted from and/or substituted into the amino acid sequence relative to another polypeptide sequence. Variants include fusion proteins.

As used herein, the twenty conventional (e.g., naturally occurring) amino acids and their abbreviations follow conventional usage. See Immunology—A Synthesis (2nd Ed., E. S. Golub & D. R. Gren, Eds., Sinauer Assoc., Sunderland, Mass. (1991)), which is incorporated herein by reference for any purpose. Stereoisomers (e.g., D-amino acids) of the twenty conventional amino acids, unnatural amino acids such as .alpha.-, .alpha.-disubstituted amino acids, N-alkyl amino acids, lactic acid, and other unconventional amino acids can also be suitable components for polypeptides of various embodiments described herein. Examples of unconventional amino acids include: 4-hydroxyproline, .gamma.-carboxyglutamate, .epsilon.-N,N,N-trimethyllysine, .epsilon.-N-acetyllysine, O-phosphoserine, N-acetylserine, N-formylmethionine, 3-methylhistidine, 5-hydroxylysine, .sigma.-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Conservative amino acid substitutions can encompass non-naturally occurring amino acid residues, which are typically incorporated by chemical peptide synthesis rather than by synthesis in biological systems. These include peptidomimetics and other reversed or inverted forms of amino acid moieties.

Naturally occurring residues can be divided into classes based on common side chain properties:
Hydrophobic: Norleucine, Met, Ala, Val, Leu, Ile;
Neutral hydrophilic: Cys, Ser, Thr, Asn, Gln;
Acidic: Asp, Glu;
Basic: His, Lys, Arg;
Residues that influence chain orientation: Gly, Pro; and
Aromatic: Trp, Tyr, Phe.

For example, non-conservative substitutions can involve the exchange of a member of one of these classes for a member from another class. Such substituted residues can be introduced, for example, into regions of a human antibody that are homologous with non-human antibodies, or into the non-homologous regions of the molecule.

In making changes to an antigen-binding protein (such as an antibody), according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−.4); threonine (−.7); serine (−.8); tryptophan (−.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte, et al., J. Mol. Biol., 157:105-131, (1982). It is known that certain amino acids can be substituted for other amino acids having a similar hydropathic index or score and still retain a similar biological activity. In making changes based upon the hydropathic index, in certain embodiments, the substitution of amino acids whose hydropathic indices are within .+−.2 is included. In certain embodiments, those which are within .+−.1 are included, and in certain embodiments, those within .+−.5 are included.

It is also understood in the art that the substitution of like amino acids can be made effectively on the basis of hydrophilicity, particularly where the biologically functional protein or peptide thereby created is intended for use in immunological embodiments. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−.4); proline (−.5.+−0.1); alanine (−.5); histidine (−.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within .+−.2 is included, in certain embodiments, those which are within .+−.1 are included, and in certain embodiments, those within .+−.5 are included. One can also identify epitopes from primary amino acid sequences on the basis of hydrophilicity. These regions are also referred to as "epitopic core regions."

Exemplary amino acid substitutions are set forth in Table 1.

TABLE 1 amino acid substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen-binding protein can have a greater circulating half-life than an antigen-binding protein that is not chemically modified. In certain embodiments, a chemically modified antigen-binding protein can have improved targeting capacity for desired cells, tissues, and/or organs. In some embodiments, a derivative antigen-binding protein is covalently modified to include one or more water soluble polymer attachments, including, but not limited to, polyethylene glycol, polyoxyethylene glycol, or polypropylene glycol. See e.g., U.S. Pat. Nos. 4,640,835; 4,496,689; 4,301,144; 4,670,417; 4,791,192 and 4,179,337. In certain embodiments, a derivative antigen-binding protein comprises one or more polymer, including, but not limited to, monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers.

In certain embodiments, a derivative is covalently modified with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity for an antigen-binding protein. In certain embodiments, PEG is used to improve the therapeutic capacity for a humanized antibody. Certain such methods are discussed, for example, in U.S. Pat. No. 6,133,426, which is hereby incorporated by reference for any purpose.

Peptide analogs are commonly used in the pharmaceutical industry as non-peptide drugs with properties analogous to those of the template peptide. These types of non-peptide compound are termed "peptide mimetics" or "peptidomimetics." Fauchere, J., Adv. Drug Res., 15:29, (1986); Veber & Freidinger, TINS, p. 392, (1985); and Evans et al., J. Med. Chem., 30:1229, (1987), which are incorporated herein by reference for any purpose. Such compounds are often developed with the aid of computerized molecular modeling. Peptide mimetics that are structurally similar to therapeutically useful peptides can be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by at least one linkage selected from: —CH.sub.2NH—, —CH.sub.2S—, —CH.sub.2-CH.sub.2-, —CH.dbd.CH-(cis & trans), —COCH.sub.2-CH(OH)CH.sub.2-, and —CH.sub.2SO—, by methods well known in the art. Systematic substitution of one or more amino acids of a consensus sequence with a D-amino acid of the same type (e.g., D-lysine in place of L-lysine) can be used in certain embodiments to generate more stable peptides. In addition, constrained peptides comprising a consensus sequence or a substantially identical consensus sequence variation can be generated by methods known in the art (Rizo & Gierasch, Ann. Rev. Biochem., 61:387, (1992), incorporated herein by reference for any purpose); for example, by adding internal cysteine residues capable of forming intramolecular disulfide bridges which cyclize the peptide.

The term "naturally occurring" as used throughout the specification in connection with biological materials such as polypeptides, nucleic acids, host cells, and the like, refers to materials which are found in nature or a form of the materials that is found in nature.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, about 65%, about 70%, about 75%, about 80%, about 85%, about 90%, about 91%, about 92%, about 93%, about 94%, about 95%, about 96%, about 97%, about 98%, about 99%, or higher identity over a specified region, when compared and aligned for maximum correspondence over a comparison window or designated region) as measured using a BLAST or BLAST 2.0 sequence comparison algorithms with default parameters described below, or through manual alignment and also visual inspection (see e.g., the NCBI website www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described herein, the algorithms can account for gaps, and the like. In various embodiments, identity exists over a region that is at least about 25 amino acids, about 50 amino acids or nucleotides in length, or over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window" includes reference to a segment of any one of the number of contiguous positions as desired. In some embodiments the "comparison window" can be selected from the group consisting of from about 50 to about 200, or about 100 to about 150, or greater than 150, if so desired in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math., 2:482, (1981), by the homology alignment algorithm of Needleman & Wunsch, J. Mol. Biol., 48:443, (1970), by the search for similarity method of Pearson & Lipman, Proc. Nat'l. Acad. Sci. USA, 85:2444, (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see e.g., Current Protocols in Molecular Biology (Ausubel et al., eds. 1995 supplement)).

An example of an algorithm that is suitable for determining percent sequence identity and sequence similarity are the BLAST and BLAST 2.0 algorithms, which are described in Altschul et al., Nuc. Acids Res., 25:3389-3402, (1977) and Altschul et al., J. Mol. Biol., 215:403-410, (1990), respectively, BLAST and BLAST 2.0 are used, with the parameters described herein, to determine percent sequence identity for the nucleic acids and proteins of various embodiments. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA, 89:10915, (1989)) alignments (B) of 50, expectation (E) of 10, M=5, N=−4, and a comparison of both strands.

The term "control sequence" refers to a polynucleotide sequence that can affect the expression and processing of coding sequences to which it is ligated. The nature of such control sequences can depend upon the host organism. In particular embodiments, control sequences for prokaryotes can include a promoter, a ribosomal binding site, and a transcription termination sequence. For example, control sequences for eukaryotes can include promoters comprising one or a plurality of recognition sites for transcription factors, transcription enhancer sequences, and transcription termination sequence. "Control sequences" can include leader sequences and/or fusion partner sequences.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct can include, but is not limited to, sequences that affect or control transcription, translation, and, if introns are present, affect RNA splicing of a coding region operably linked thereto. The expression vectors useful in various embodiments described herein can contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic makeup to the original parent cell, so long as the gene of interest is present.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See e.g., Graham et al., 1973, Virology 52:456; Sambrook et al., 2001, Molecular Cloning: A Laboratory Manual, supra; Davis et al., 1986, Basic Methods in Molecular Biology, Elsevier; Chu et al., 1981, Gene 13:197. Such techniques can be used to introduce one or more exogenous DNA moieties into suitable host cells. A transfection may be transient.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA can recombine with that of the cell by physically integrating into a chromosome of the cell, or can be maintained transiently as an episomal element without being replicated, or can replicate independently as a plasmid. A cell is considered to have been "stably transformed" when the transforming DNA is replicated with the division of the cell.

The term "immunologically functional fragment" (or simply "fragment") of an antibody or immunoglobulin chain (heavy or light chain) antigen-binding protein, as used herein, is a species of antigen-binding protein comprising a portion (regardless of how that portion is obtained or synthesized) of an antibody that lacks at least some of the amino acids present in a full-length chain but which is still capable of specifically binding to an antigen.

"Specific binding" should be understood to mean that the predominant antigens bound by the antigen-binding protein are the activin receptors against which the antigen-binding protein, e.g. ActRIIA (SEQ ID NO: 1) and ActRIIB (SEQ ID NO: 2). This does not necessarily preclude, however, binding of an antigen-binding protein to proteins other than the activin receptors. In various embodiments, the binding to other proteins represents less than about 5%, less than about 10%, less than about 15%, less than about 20% or less than about 25% of the total protein bound.

Fragments of antigen-binding proteins are biologically active in that they bind to the target antigen and can compete with other antigen-binding proteins, including intact antibodies, for binding to a given epitope or antigen. In some embodiments, the fragments are neutralizing fragments. In some embodiments, the fragments can block or reduce the likelihood of the interaction between activin and its receptor(s). In one aspect, such a fragment will retain at least one CDR present in the full-length light or heavy chain, and in some embodiments will comprise a single heavy chain and/or light chain or portion thereof. These biologically active fragments can be produced by recombinant DNA techniques, or can be produced by enzymatic or chemical cleavage of antigen-binding proteins, including intact antibodies. Immunologically functional immunoglobulin fragments include, but are not limited to, Fab, a diabody (heavy chain variable domain on the same polypeptide as a light chain variable domain, connected via a short peptide linker that is too short to permit pairing between the two domains on the same chain), Fab', F(ab').sub.2, Fv, domain antibodies and single-chain antibodies, and can be derived from any mammalian source, including but not limited to human, mouse, rat, camelid or rabbit. It is further contemplated that a functional portion of the antigen-binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life. As will be appreciated by one of skill in the art, an antigen-binding protein can include nonprotein components.

Certain antigen-binding proteins described herein are antibodies or are derived from antibodies. In certain embodiments, the polypeptide structure of the antigen-binding proteins is based on antibodies, including, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the antigen-binding protein comprises or consists of avimers (tightly binding peptide).

An "Fc" region comprises two heavy chain fragments comprising the C.sub.H1 and C.sub.H2 domains of an antibody. The two heavy chain fragments are held together by two or more disulfide bonds and by hydrophobic interactions of the C.sub.H3 domains.

A "Fab fragment" comprises one light chain and the C.sub.H1 and variable regions of one heavy chain. The heavy chain of a Fab molecule cannot form a disulfide bond with another heavy chain molecule.

A "Fab' fragment" comprises one light chain and a portion of one heavy chain that contains the V.sub.H domain and the C.sub.H1 domain and also the region between the C.sub.H1 and C.sub.H2 domains, such that an interchain disulfide bond can be formed between the two heavy chains of two Fab' fragments to form an F(ab').sub.2 molecule.

A "F(ab').sub.2 fragment" contains two light chains and two heavy chains containing a portion of the constant region between the C.sub.H1 and C.sub.H2 domains, such that an interchain disulfide bond is formed between the two heavy chains. A F(ab').sub.2 fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203, the disclosures of which are incorporated by reference.

A "domain antibody" is an immunologically functional immunoglobulin fragment containing only the variable region of a heavy chain or the variable region of a light chain. In some instances, two or more V.sub.H regions are covalently joined with a peptide linker to create a bivalent domain antibody. The two V.sub.H regions of a bivalent domain antibody can target the same or different antigens.

A "bivalent antigen-binding protein" or "bivalent antibody" comprises two antigen-binding sites. In some instances, the two binding sites have the same antigen specificities. Bivalent antigen-binding proteins and bivalent antibodies can be bispecific as defined herein. A bivalent antibody other than a "multispecific" or "multifunctional" antibody, in certain embodiments, typically is understood to have each of its binding sites identical.

A "multispecific antigen-binding protein" or "multispecific antibody" is one that targets more than one antigen or epitope.

A "bispecific," "dual-specific," or "bifunctional" antigen-binding protein or antibody is a hybrid antigen-binding protein or antibody, respectively, having two different antigen-binding sites. Bispecific antigen-binding proteins and antibodies are a species of multispecific antigen-binding protein antibody and can be produced by a variety of methods including, but not limited to, fusion of hybridomas or linking of Fab' fragments. See e.g., Songsivilai and Lachmann, 1990, Clin. Exp. Immunol., 79:315-321; Kostelny et al., 1992, J Immunol., 148:1547-1553. The two binding sites of a bispecific antigen-binding protein or antibody will bind to two different epitopes, which can reside on the same or different protein targets.

Each individual immunoglobulin chain is typically composed of several "immunoglobulin domains." These domains are the basic units of which antibody polypeptides are composed. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that can be responsible for effector function. The number of heavy chain constant region domains will depend on the isotype. IgG heavy chains, for example, contain three C region domains known as C.sub.H1, C.sub.H2 and C.sub.H3. The antibodies that are provided can have any of these isotypes and subtypes "Antigen-binding region" means a protein, or a portion of a protein, that specifically binds a specified antigen (e.g., a paratope). For example, that portion of an antigen-binding protein that contains the amino acid residues that interact with an antigen and confer on the antigen-binding protein its specificity and affinity for the antigen is referred to as "antigen-binding region." An antigen-binding region typically includes one or more Complementary Binding Regions (CDRs). Certain antigen-binding regions also include one or more "framework" regions. A "CDR" is an amino acid sequence that contributes to antigen-binding specificity and affinity. "Framework" regions can aid in maintaining the proper conformation of the CDRs to promote binding between the antigen-binding region and an antigen. Structurally, framework regions can be located in antibodies between CDRs.

In certain aspects, recombinant antigen-binding proteins that bind dual activin receptors, are provided. In this context, a "recombinant antigen-binding protein" is a protein made using recombinant techniques, i.e., through the expression of a recombinant nucleic acid as described herein. Methods and techniques for the production of recombinant proteins are well known in the art.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen-binding protein. An intact antibody will generally comprise at least two full-length heavy chains and two full-length light chains, but in some instances can include fewer chains such as antibodies naturally occurring in camelids which can comprise only heavy chains Antibodies can be derived solely from a single source, or can be "chimeric," that is, different portions of the antibody can be derived from two different antibodies as described further below. The antigen-binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

Naturally occurring antibody structural units typically comprise a tetramer. Each such tetramer typically is composed of two identical pairs of polypeptide chains, each pair having one full-length "light" and one full-length "heavy" chain. The amino-terminal portion of each chain typically includes a variable region that typically is responsible for antigen recognition. The carboxy-terminal portion of each chain typically defines a constant region that can be responsible for effector function. The variable regions of each light/heavy chain pair typically form the antigen-binding site.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md., (1987 and 1991), or Chothia & Lesk, J. Mol. Biol., 196:901-917, (1987); Chothia et al., Nature, 342:878-883, (1989)).

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the "AbM" definition and the contact definition.

The Kabat definition is a standard for numbering the residues in an antibody and is typically used to identify CDR regions. See e.g., Johnson & Wu, Nucleic Acids Res., 28:214-8, (2000). The Chothia definition is similar to the Kabat definition, but the Chothia definition takes into account positions of certain structural loop regions. See e.g., Chothia et al., J. Mol. Biol., 196:901-17, (1986); Chothia et al., Nature, 342:877-83, (1989). The "AbM" definition uses an integrated suite of computer programs produced by Oxford Molecular Group that model antibody structure. See e.g., Martin et al., Proc. Natl. Acad. Sci. (USA), 86:9268-9272, (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics, Suppl. 3:194-198, (1999). The contact definition is based on an analysis of the available complex crystal structures. See e.g., MacCallum et al., J. Mol. Biol., 5:732-45, (1996).

By convention, the CDR regions in the heavy chain are typically referred to as H1, H2, and H3 and are numbered sequentially in the direction from the amino terminus to the carboxy terminus. The CDR regions in the light chain are typically referred to as L1, L2, and L3 and are numbered sequentially in the direction from the amino terminus to the carboxy terminus.

The term "binds specifically" means that the antigen-binding protein preferentially binds to a specified target(s) or specified sequence. "Binds specifically" should not be construed to exclude binding to other than the target(s) or specific sequence recited, however the predominant binding activity should be for the specified target(s) or amino acid sequence. "Simultaneously binds" means that the antigen-binding protein can bind two different targets, e.g. two different activin receptors at the same time. The two different activin receptors can be ActRIIA and ActRIIB. The antigen-binding protein can be an antagonistic dual-receptor antibody. A dual receptor antibody can bind two receptors simultaneously or alternatively can specifically bind the two different receptors individually. The antibody can bind to an ActRIIA homodimer, an ActRIIB homobdimer or an ActRIIA/ActRIIB heterodimer. By binding to the receptors, the antibody inhibits or prevents biological activity mediated through that/those receptor(s).

The term "light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains.

Specificity of antibodies in various embodiments or fragments thereof, for activin receptors can be determined based on affinity and/or avidity. Affinity, represented by the equilibrium constant for the dissociation of an antigen with an antibody (Kd), measures the binding strength between an antigenic determinant and an antibody-binding site. Avidity is the measure of the strength of binding between an antibody with its antigen. Avidity is related to both the affinity between an epitope with its antigen-binding site on the antibody, and the valence of the antibody, which refers to the number of antigen-binding sites specific for a particular epitope. The lesser the value of the Kd, the stronger the binding strength between an antigenic determinant and the antibody binding site.

The term "heavy chain" includes a full-length heavy chain and fragments thereof having sufficient variable region sequence to confer binding specificity. A full-length heavy chain includes a variable region domain, $V_H$, and three constant region domains, $C_H1$, $C_H2$, and $C_H3$. The $V_H$ domain is at the amino-terminus of the polypeptide, and the $C_H$ domains are at the carboxyl-terminus, with the $C_H3$ being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

A bispecific or bifunctional antibody typically is an artificial hybrid antibody having two different heavy/light chain pairs and two different binding sites. Bispecific antibodies can be produced by a variety of methods including, but not limited to, fusion of hybridomas or linking of Fab' fragments. See, e.g., Songsivilai et al., Clin. Exp. Immunol., 79:315-321, (1990); Kostelny et al., J. Immunol., 148:1547-1553, (1992).

Some species of mammals can also produce antibodies having only a single heavy chain.

Each individual immunoglobulin chain is typically composed of several "immunoglobulin domains." These domains are the basic units of which antibody polypeptides are composed. The heavy chain C region typically comprises one or more domains that can be responsible for effector function. The number of heavy chain constant region domains will depend on the isotype. The antibodies that are provided can have any of isotypes and subtypes.

The term "variable region" or "variable domain" refers to a portion of the light and/or heavy chains of an antibody. In certain embodiments, variable regions of different antibodies differ extensively in amino acid sequence even among antibodies of the same species. The variable region of an antibody typically determines specificity of a particular antibody for its target The term "neutralizing antigen-binding protein" or "neutralizing antibody" refers to an antigen-binding protein or antibody, respectively, that binds to a ligand and prevents or reduces the binding of the ligand to a binding partner. This can be done, for example, by directly blocking a binding site on the ligand or by binding to the ligand and altering the ligand's ability to bind through indirect means (such as structural or energetic alterations in the ligand). In some embodiments, the term can also denote an antigen-binding protein that prevents the protein to which it is bound from performing a biological function. In assessing the binding and/or specificity of an antigen-binding protein, e.g., an antibody or immunologically functional fragment thereof, an antibody or fragment can substantially inhibit binding of a ligand to its binding partner when an excess of antibody reduces the quantity of binding partner bound to the ligand by at least about 1-20, about 20-30%, about 30-40%, about 40-50%, about 50-60%, about 60-70%, about 70-80%, about 80-85%, about 85-90%, about 90-95%, about 95-97%, about 97-98%, about 98-99% or more (as measured in an in vitro competitive binding assay). In some embodiments, in the case of dual activin receptor antigen-binding proteins, such a neutralizing molecule can diminish the ability of activin to bind the receptor. In some embodiments, the neutralizing ability is characterized and/or described via a competition assay. In some embodiments, the neutralizing ability is described in terms of an IC.sub.50 or EC.sub.50 value. In some embodiments, the antigen-binding proteins may be non-neutralizing antigen-binding proteins.

The term "target" refers to a molecule or a portion of a molecule capable of being bound by an antigen-binding protein. In certain embodiments, a target can have one or more epitopes. In certain embodiments, a target is an antigen. The use of "antigen" in the phrase "antigen-binding protein" simply denotes that the protein sequence that comprises the antigen can be bound by an antibody. In this context, it does not require that the protein be foreign or that it be capable of inducing an immune response.

The term "compete" when used in the context of antigen-binding proteins (e.g., neutralizing antigen-binding proteins or neutralizing antibodies) that compete for the same epitope means competition between antigen-binding proteins as determined by an assay in which the antigen-binding protein (e.g., antibody or immunologically functional fragment thereof) being tested prevents or inhibits (e.g., reduces) specific binding of a reference antigen-binding protein (e.g., a ligand, or a reference antibody) to a common antigen (e.g., activin or a fragment thereof). Numerous types of competitive binding assays can be used to determine if one antigen-binding protein competes with another, for example: solid phase direct or indirect radioimmunoassay (RIA), solid phase direct or indirect enzyme immunoassay (EIA), sandwich competition assay (see e.g., Stahli, et al., 1983, Methods in Enzymology, 9:242-253); solid phase direct biotin-avidin EIA (see e.g., Kirkland, et al., 1986, J. Immunol., 137:3614-3619) solid phase direct labeled assay, solid phase direct labeled sandwich assay (see e.g., Harlow and Lane, 1988, Antibodies, A Laboratory Manual, Cold Spring Harbor Press); solid phase direct label RIA using 1-125 label (see e.g., Morel, et al., 1988, Molec. Immunol., 25:7-15); solid phase direct biotin-avidin EIA (see e.g., Cheung, et al., 1990, Virology, 176:546-552); and direct labeled RIA (Moldenhauer et al., 1990, Scand. J. Immunol., 32:77-82). Typically, such an assay involves the use of purified antigen bound to a solid surface or cells bearing either of these, an unlabelled test antigen-binding protein and a labeled reference antigen-binding protein. Competitive inhibition is measured by determining the amount of label bound to the solid surface or cells in the presence of the test antigen-binding protein. Usually the test antigen-binding protein is present in excess. Antigen-binding proteins identified by competition assay (competing antigen-binding proteins) include antigen-binding proteins binding to the same epitope as the reference antigen-binding proteins and antigen-binding proteins binding to an adjacent epitope sufficiently proximal to the epitope bound by the reference antigen-binding protein for steric hindrance to occur. Additional details regarding methods for determining competitive binding are provided in the examples herein. Usually, when a competing antigen-binding protein is present in excess, it will inhibit (e.g., reduce) specific binding of a reference antigen-binding protein to a common antigen by at least about 40-45%, about 45-50%, about 50-55%, about 55-60%, about 60-65%, about 65-70%, about 70-75% or about 75% or more. In some instances, binding is inhibited by at least about 80-85%, about 85-90%, about 90-95%, about 95-97%, or about 97% or more.

The term "antigen" refers to a molecule or a portion of a molecule capable of being bound by a selective binding agent, such as an antigen-binding protein (including, e.g., an antibody or immunological functional fragment thereof). In some embodiments, the antigen is capable of being used in an animal to produce antibodies capable of binding to that antigen. An antigen can possess one or more epitopes that are capable of interacting with different antigen-binding proteins, e.g., antibodies.

The term "epitope" includes any determinant capable of being bound by an antigen-binding protein, such as an antibody or to a T-cell receptor. An epitope is a region of an antigen that is bound by an antigen-binding protein that targets that antigen, and when the antigen is a protein, includes specific amino acids that directly contact the antigen-binding protein. Most often, epitopes reside on proteins, but in some instances can reside on other kinds of molecules, such as nucleic acids. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of proteins and/or macromolecules.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least about 50% (on a molar basis) of all macromolecular species present. In other embodiments, a substantially pure composition will comprise at least about 80%, about 85%, about 90%, about 95%, or about 99% of all macromolecular species present in the composition. In other embodiments, the object species is purified to essential homogeneity wherein contaminating species cannot be detected in the composition by conventional detection methods and thus the composition consists of a single detectable macromolecular species.

The term "biological sample," as used herein, includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

The term "pharmaceutical agent composition" (or agent or drug) as used herein refers to a chemical compound, composition, agent or drug capable of inducing a desired therapeutic effect when properly administered to a patient. It does not necessarily require more than one type of ingredient.

The terms "therapeutically effective amount" and "therapeutically effective dose" refer to the amount of a dual activin receptor antigen-binding protein determined to produce a therapeutic response in a mammal. Such therapeutically effective amounts can be ascertained by one of ordinary skill in the art. The exact dose and formulation will depend on the purpose of the treatment, and will be ascertainable by one skilled in the art using known techniques (see e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)).

The term "pharmaceutically acceptable salts" or "pharmaceutically acceptable carrier" is meant to include salts of the active compounds which are prepared with relatively nontoxic acids or bases, depending on the particular substituents found on the compounds described herein.

The term "modulator," as used herein, is a compound that changes or alters the activity or function of a molecule. For example, a modulator can cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Certain exemplary activities and functions of a molecule include, but are not limited to, binding affinity, enzymatic activity, and signal transduction. Certain exemplary inhibitors include, but are not limited to, proteins, peptides, antigen-binding fragments, antibodies, peptibodies, carbohydrates or small organic molecules. An antibody can be made against dual activin receptors. Peptibodies are described in, e.g., U.S. Pat. No. 6,660,843 (corresponding to PCT Application No. WO 01/83525).

The terms "patient" and "subject" are used interchangeably and include human and non-human animal subjects as well as those with formally diagnosed disorders, those without formally recognized disorders, those receiving medical attention, those at risk of developing the disorders, etc.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors.

The term "prevent" does not require the 100% elimination of the possibility of an event. Rather, it denotes that the likelihood of the occurrence of the event has been reduced in the presence of the compound or method.

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the specification. See e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

Antigen-binding proteins (ABPs) that bind dual activin receptors, are provided herein. In some embodiments, the antigen-binding proteins provided are polypeptides which comprise one or more complementary determining regions (CDRs), as described herein. In some antigen-binding proteins, the CDRs are embedded into a "framework" region, which orients the CDR(s) such that the proper antigen-binding properties of the CDR(s) is achieved. In some embodiments, antigen-binding proteins provided herein can interfere with, block, reduce or modulate the interaction between activin and activin receptors. Such antigen-binding proteins are denoted as "neutralizing." In some embodiments, the neutralizing antigen-binding protein binds to dual activin receptors in a location and/or manner that prevents activin from binding to the activin receptors.

In some embodiments, the antigen-binding proteins provided herein are capable of inhibiting activin-mediated activity (including binding). In some embodiments, antigen-binding proteins binding to an activin receptor epitope can inhibit, inter alia, interactions between activin and activin receptors and other physiological effects mediated by the activin/activin receptor interaction. In some embodiments, the antigen-binding proteins are chimeras, such as a human/mouse chimera.

The antigen-binding proteins can be used in a variety of therapeutic applications, as explained herein. For example, in some embodiments the activin receptor antigen-binding proteins are useful for treating diseases and conditions associated with activin and/or activin receptors such as diseases related to muscle wasting. The muscle wasting diseases can include, but are not limited to, the following conditions: cancer cachexia, muscular dystrophy, amyotrophic lateral sclerosis, congestive obstructive pulmonary disease, chronic heart failure, chemical cachexia, cachexia from HIV/AIDS, renal failure, uremia, rheumatoid arthritis, age-related sarcopenia, age-related frailty, organ atrophy, carpal tunnel syndrome, androgen deprivation, and muscle-wasting due to inactivity from prolonged bed rest, spinal cord injury, stroke, bone fracture, burns, aging, insulin resistance, and other disorders. The muscle wasting may also result from weightlessness due to space flight. The antigen-binding proteins can be antagonistic dual receptor antibodies. The antibodies can be against ActRIIB and ActRIIA.

Additional uses can include, but are not limited to a method of reducing or blocking myostatin, activin A or GDF-11 activity is provided comprising administering dual receptor antigen-binding proteins and polypeptides, or pharmaceutical compositions containing these, to a subject in need of such treatment. The antigen-binding proteins can be antagonistic dual receptor antibodies. The antibodies can be against ActRIIB and ActRIIA.

In another aspect, a method of increasing lean muscle mass or increasing the ratio of lean muscle mass to fat mass in a subject in need of such treatment is provided comprising administering an effective amount of the composition or pharmaceutical composition containing dual receptor antigen-binding proteins or polypeptides to the subject. The antigen-binding proteins can be antagonistic dual receptor antibodies. The antibodies can be against ActRIIB and ActRIIA.

In another aspect, a method of treating or preventing a muscle wasting disease in a subject suffering from such a disorder is provided comprising administering a therapeutic composition containing an antigen-binding polypeptide or protein to the subject.

In another aspect, a method of treating conditions in which activin is overexpressed in a subject in need of such treatment is provided comprising, administering an effective amount of a therapeutic composition containing antigen-binding proteins or polypeptides to the subject. In one embodiment, the disease is cancer. In another aspect, the present invention provides a method of treating a metabolic disorder comprising administering a therapeutic composition containing antigen-binding proteins or polypeptides to a subject in need of such treatment, wherein the metabolic disorder is selected from bone loss, diabetes, obesity, impaired glucose tolerance, hyperglycemia, and metabolic syndrome. The antigen-binding proteins can be antagonistic dual receptor antibodies. The antibodies can be against ActRIIB and ActRIIA.

In some embodiments, the antigen-binding proteins that are provided comprise one or more CDRs (e.g., 1, 2, 3, 4, 5 or 6 CDRs). In some embodiments, the antigen-binding protein comprises (a) a polypeptide structure and (b) one or more CDRs that are inserted into and/or joined to the polypeptide structure. The polypeptide structure can take a variety of different forms. For example, it can be, or comprise, the framework of a naturally occurring antibody, or fragment or variant thereof, or can be completely synthetic in nature.

In certain embodiments, the polypeptide structure of the antigen-binding proteins is an antibody or is derived from an antibody, including, but not limited to, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and portions or fragments of each, respectively. In some instances, the antigen-binding protein is an immunological fragment of an antibody (e.g., a Fab fragment, a Fab' fragment, a F(ab').sub.2 fragment, an Fv fragment, a diabody, or a single chain antibody molecule, such as an scFv)

In embodiments where the antigen-binding protein is used for therapeutic applications, an antigen-binding protein can inhibit, interfere with or modulate one or more biological activities of activin. In one embodiment, an antigen-binding protein binds specifically to activin receptors and/or substantially inhibits binding of human activin to activin receptors by at least about 20%-40%, about 40-60%, about 60-80%, about 80-85%, or more (for example, by measuring binding in an in vitro competitive binding assay).

Some of the antigen-binding proteins that are provided herein are antibodies. In some embodiments, the antigen-binding protein has a K.sub.d of less (binding more tightly) than about 10.sup.-7, about 10.sup.-8, about 10.sup.-9, about 10.sup.-10, about 10.sup.-11, about 10.sup.-12, about 10.sup.-13M. In some embodiments, the antigen-binding protein has an IC.sub.50 for blocking the binding of activin to activin receptors of less than about 1 .mu.M, about 1000 nM to about 100 nM, about 100 nM to about 10 nM, about 10 nM to about 1 nM, about 1000 pM to about 500 pM, about 500 pM to about 200 pM, less than about 200 pM, about 200 pM to about 150 pM, about 200 pM to about 100 pM, about 100 pM to about 10 pM, about 10 pM to about 1 pM.

In some embodiments, the antigen-binding proteins bind to a specific conformational state of activin receptors to prevent activin from interacting with the receptors. When activin is prevented from interacting with activin receptors, this can prevent or block activin or activin receptor mediated activity and the resultant pathology resulting from the interaction.

As described herein, an antigen-binding protein to activin receptors can comprise a humanized antibody and/or part thereof. A practical application of such a strategy is the "humanization" of the mouse humoral immune system.

In certain embodiments, a humanized antibody is substantially non-immunogenic in humans. In certain embodiments, a humanized antibody has substantially the same affinity for a target as an antibody from another species from which the humanized antibody is derived. See e.g., U.S. Pat. No. 5,530,101; U.S. Pat. No. 5,693,761; U.S. Pat. No. 5,693,762; and U.S. Pat. No. 5,585,089.

In certain embodiments, amino acids of an antibody variable domain that can be modified without diminishing the native affinity of the antigen-binding domain while reducing its immunogenicity are identified. See e.g., U.S. Pat. Nos. 5,766,886 and 5,869,619.

In certain embodiments, modification of an antibody by methods known in the art is typically designed to achieve increased binding affinity for a target and/or to reduce immunogenicity of the antibody in the recipient. In certain embodiments, humanized antibodies can be modified to eliminate glycosylation sites in order to increase affinity of the antibody for its cognate antigen. See e.g., Co et al., Mol. Immunol., 30:1361-1367, (1993). In certain embodiments, techniques such as "reshaping," "hyperchimerization," or "veneering/resurfacing" are used to produce humanized antibodies. See e.g., Vaswami et al., Annals of Allergy, Asthma, & Immunol., 81:105, (1998); Roguska et al., Prot. Engin., 9:895-904, (1996); and U.S. Pat. No. 6,072,035. In certain such embodiments, such techniques typically reduce antibody immunogenicity by reducing the number of foreign residues, but do not prevent anti-idiotypic and anti-allotypic responses following repeated administration of the antibodies. Certain other methods for reducing immunogenicity are described, e.g., in Gilliland et al., J. Immunol., 62(6):3663-71, (1999).

In certain instances, humanizing antibodies can result in a loss of antigen-binding capacity. The humanized antibodies can then be "back mutated." In such embodiments, the humanized antibody can be mutated to include one or more of the amino acid residues found in the donor antibody. See e.g., Saldanha et al., Mol. Immunol., 36:709-19, (1999).

In certain embodiments the complementarity determining regions (CDRs) of the light and heavy chain variable regions of an antibody to activin receptors can be grafted to framework regions (FRs) from the same, or another, species. In certain embodiments, the CDRs of the light and heavy chain variable regions of an antibody to activin receptors can be grafted to consensus human FRs. To create consensus human FRs, in certain embodiments, FRs from several human heavy chain or light chain amino acid sequences are aligned to identify a consensus amino acid sequence. In certain embodiments, the FRs of an antibody to activin receptor heavy chain or light chain are replaced with the FRs from a different heavy chain or light chain. In certain embodiments, rare amino acids in the FRs of the heavy and light chains of an antibody to activin receptors are not replaced, while the rest of the FR amino acids are replaced. Rare amino acids are specific amino acids that are in positions in which they are not usually found in FRs. In certain embodiments, the grafted variable regions from an antibody to activin receptors can be used with a constant region that is different from the constant region of an antibody to the activin receptors. In certain embodiments, the grafted variable regions are part of a single chain Fv antibody. CDR grafting is described, e.g., in U.S. Pat. Nos. 6,180,370; 6,054,297; 5,693,762; 5,859,205; 5,693,761; 5,565,332; 5,585,089; and 5,530,101, and in Jones, et al., Nature, 321:522-525, (1986); Riechmann et al., Nature, 332:323-327, (1988); Verhoeyen, et al., Science, 239:1534-1536, (1988), Winter, FEBS Letts., 430:92-94, (1998), which are hereby incorporated by reference for any purpose.

In certain embodiments, antigen-binding proteins (such as antibodies) are produced by immunization with an antigen (e.g., activin receptors or a fragment thereof). The antibodies can be produced by immunization with full-length receptors, a soluble form of the receptors, the catalytic domains alone, the mature form of activin receptors, a splice variant form of the receptors, or a fragment thereof. In certain embodiments, the antibodies of can be polyclonal or monoclonal, and/or can be recombinant antibodies In certain embodiments, strategies can be employed to manipulate inherent properties of an antibody, such as the affinity of an antibody for its target. Such strategies include, but are not limited to, the use of site-specific or random mutagenesis of the polynucleotide molecule encoding an antibody to generate an antibody variant. In certain embodiments, such generation is followed by screening for antibody variants that exhibit the desired change, e.g. increased or decreased affinity.

In certain embodiments, the amino acid residues targeted in mutagenic strategies are those in the CDRs. In other embodiments, amino acids in the framework regions of the variable domains can be targeted. Such framework regions have been shown to contribute to the target binding properties of certain antibodies. See e.g., Hudson, Curr. Opin. Biotech., 9:395-402, (1999) and references therein.

In certain embodiments, smaller and more effectively screened libraries of antibody variants can be produced by restricting random or site-directed mutagenesis to hyper-mutation sites in the CDRs, which are sites that correspond to areas prone to mutation during the somatic affinity maturation process. See e.g., Chowdhury & Pastan, Nature Biotech., 17: 568-572, (1999) and references therein. In certain embodiments, certain types of DNA elements can be used to identify hyper-mutation sites including, but not limited to, certain direct and inverted repeats, certain consensus sequences, certain secondary structures, and certain palindromes. For example, such DNA elements that can be used to identify hyper-mutation sites include, but are not limited to, a tetrabase sequence comprising a purine (A or G), followed by guanine (G), followed by a pyrimidine (C or T), followed by either adenosine or thymidine (A or T) (i.e., A/G-G-C/T-A/T). Another example of a DNA element that can be used to identify hyper-mutation sites is the serine codon, A-G-C/T.

For preparation of suitable antibodies for various embodiments e.g., recombinant, monoclonal, or polyclonal antibodies, many techniques known in the art can be used (see e.g., Kohler & Milstein, Nature, 256:495-497, (1975); Kozbor et al., Immunology Today, 4:72, (1983); Cole et al., pp. 77-96 in Monoclonal Antibodies and Cancer Therapy, Alan R. Liss, Inc., (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see e.g., Kuby, Immunol., (3.sup.rd ed. 1997)). Techniques for the production of single chain antibodies or recombinant antibodies (U.S. Pat. No. 4,946,778; U.S. Pat. No. 4,816,567) can be adapted to produce antibodies to polypeptides for various embodiments. Also, transgenic mice, or other organisms such as other mammals, may be used to express humanized or human antibodies (see e.g., U.S. Pat. Nos. 5,545,807; 5,545,806; 5,569,825; 5,625,126; 5,633,425; 5,661,016; Marks et al., Bio/Technology, 10:779-783, (1992); Lonberg et al., Nature, 368:856-859, (1994); Morrison, Nature, 368:812-13, (1994); Fishwild et al., Nature Biotechnology, 14:845-51, (1996); Neuberger, Nature Biotechnology, 14:826, (1996); and Lonberg & Huszar, Intern. Rev. Immunol., 13:65-93, (1995)). Alternatively, phage display technology can be used to identify antibodies and heteromeric Fab fragments that specifically bind to selected antigens (see e.g., McCafferty et al., Nature, 348:552-554, (1990); Marks, et al., Biotechnology, 10:779-783, (1992)). Antibodies can also be made bispecific, i.e., able to recognize two different antigens (see e.g., WO 93/08829, Traunecker, et al., EMBO J., 10:3655-3659, (1991); and Suresh, et al., Methods in Enzymology, 121:210, (1986)). Antibodies can also be heteroconjugates, e.g., two covalently joined antibodies, or immunotoxins (see e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see e.g., Jones, et al., Nature, 321:522-525, (1986); Riechmann et al., Nature, 332:323-327, (1988); Verhoeyen, et al., Science, 239:1534-1536, (1988) and Presta, Curr. Op. Struct. Biol. 2:593-596, (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more V.sub.H genes, one or more D.sub.H genes, one or more J.sub.H genes, a mu constant region, and usually a second constant region (e.g. a gamma constant region) are formed into a construct for insertion into an animal. This approach is described in U.S. Pat. No. 5,545,807 to Surani, et al. and U.S. Pat. Nos. 5,545,806; 5,625,825; 5,625,126; 5,633,425; 5,661,016; 5,770,429; 5,789,650; 5,814,318; 5,877,397; 5,874,299; and 6,255,458 each to Lonberg & Kay, U.S. Pat. Nos. 5,591,669 and 6,023,010 to Krimpenfort & Berns, U.S. Pat. Nos. 5,612,205, 5,721,367, and 5,789,215 to Berns et al., and U.S. Pat. No. 5,643,763 to Choi & Dunn, and GenPharm International U.S. patent application Ser. Nos. 07/574,748; 07/575,962; 07/810,279; 07/853,408; 07/904,068; 07/990,860; 08/053,131; 08/096,762; 08/155,301; 08/161,739; 08/165,699; 08/209,741, the disclosures of which are hereby incorporated by reference. See also, European Patent No. 0 546 073 B1, International Patent Application Nos.: WO 92/03918; WO 92/22645; WO 92/22647; WO 92/22670; WO 93/12227; WO 94/00569; WO 94/25585; WO 96/14436; WO 97/13852; and WO 98/24884, and U.S. Pat. No. 5,981,175, the disclosures of which are hereby incorporated by reference in their entirety. See further, Taylor, et al., 1992, Chen, et al., 1993; Tuaillon, et al., 1993; Choi, et al., 1993, Lonberg, et al., (1994); Taylor, et al., (1994), and Tuaillon, et al., (1995), Fishwild, et al., (1996), the disclosures of which are hereby incorporated by reference.

In one embodiment, the antibody is conjugated to an "effector" moiety. The effector moiety can be any number of molecules, including labeling moieties such as radioactive labels or fluorescent labels, or can be a therapeutic moiety.

The antibodies can be fused to additional amino acid residues. Such amino acid residues can be a peptide tag, perhaps to facilitate isolation. Other amino acid residues for homing of the antibodies to specific organs or tissues are also contemplated.

In certain embodiments the antibody or the antigen-binding region of any of the monoclonal antibodies described herein can be used to treat cancer or retinopathy.

"Cancer" should be understood to be a general term that can be used to indicate any of various types of malignant neoplasms, which may invade surrounding tissues, may metastasize to several sites and may likely recur after attempted removal. The term may also refer to any carcinoma or sarcoma.

"Retinopathy" should be understood to mean a non-inflammatory disease of the retina, as distinguished from retinitis. "Diabetic retinopathy" should be understood to mean retinal changes occurring in diabetes, that can be marked by punctuate hemorrhages, microaneurysms and sharply defined waxy exudates.

In treating cancer, the antigen-binding region can be joined to at least a functionally active portion of a second protein having therapeutic activity. The second protein can include, but is not limited to, an enzyme, lymphokine, oncostatin or toxin. Suitable toxins include doxorubicin, daunorubicin, taxol, ethiduim bromide, mitomycin, etoposide, tenoposide, vincristine, vinblastine, colchicine, dihydroxy anthracin dione, actinomycin D, diphtheria toxin, *Pseudomonas* exotoxin (PE) A, PE40, ricin, abrin, glucocorticoid and radioisotopes.

As will be appreciated, antibodies can be expressed in cell lines other than hybridoma cell lines. Sequences encoding particular antibodies can be used to transform a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216; 4,912,040; 4,740,461; and 4,959,455, (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Cell lines of particular preference are selected through determining which cell lines have high expression levels of the antibody of interest.

In certain embodiments, antigen-binding proteins can comprise an immunoglobulin molecule of at least one of the IgG1, IgG2, IgG3, IgG4, Ig E, IgA, IgD, and IgM isotype.

In certain embodiments, antigen-binding proteins comprise a human kappa light chain and/or a human heavy chain. In certain embodiments, the heavy chain is of the IgG1, IgG2, IgG3, IgG4, IgE, IgA, IgD, or IgM isotype. In certain embodiments, antigen-binding proteins have been cloned for expression in mammalian cells. In certain embodiments, antigen-binding proteins comprise a constant region other than any of the constant regions of the IgG1, IgG2, IgG3, IgG4, IgE, IgA, IgD, and IgM isotype.

In certain embodiments, substantial modifications in the functional and/or chemical characteristics of antibodies to activin receptors can be accomplished by selecting substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" can involve a substitution of a native amino acid residue with a nonnative residue such that there is little or no effect on the polarity or charge of the amino acid residue at that position. Furthermore, any native residue in the polypeptide can also be substituted with alanine, as has been previously described for "alanine scanning mutagenesis."

Desired amino acid substitutions (whether conservative or non-conservative) can be determined by those skilled in the art at the time such substitutions are desired. In certain embodiments, amino acid substitutions can be used to identify important residues of antibodies to activin receptors, or to increase or decrease the affinity of the antibodies to activin receptors as described herein.

In certain embodiments, antibodies or antigen-binding proteins can be expressed in cell lines other than hybridoma cell lines. Sequences encoding particular antibodies can be used for transformation of a suitable mammalian host cell. According to certain embodiments, transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216; 4,912,040; 4,740,461; and 4,959,455, (which patents are hereby incorporated herein by reference for any purpose). In certain embodiments, the transformation procedure used can depend upon the host to be transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include, but are not limited to, many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines can be selected through determining which cell lines have high expression levels and produce antibodies with constitutive HGF binding properties. Appropriate expression vectors for mammalian host cells are well known.

In certain embodiments, antigen-binding proteins comprise one or more polypeptides. Any of a variety of expression vector/host systems can be utilized to express polynucleotide molecules encoding polypeptides comprising one or more antigen-binding protein components or the antigen-binding protein itself. Such systems include, but are not limited to, microorganisms, such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV, tobacco mosaic virus, TMV) or transformed with bacterial expression vectors (e.g., Ti or pBR322 plasmid); or animal cell systems.

In certain embodiments, a polypeptide comprising one or more antigen-binding protein components or the antigen-binding protein itself is recombinantly expressed in yeast. Certain such embodiments use commercially available expression systems, e.g., the *Pichia* Expression System (Invitrogen, San Diego, Calif.), following the manufacturer's instructions. In certain embodiments, such a system relies on the pre-pro-alpha sequence to direct secretion. In certain embodiments, transcription of the insert is driven by the alcohol oxidase (AOX1) promoter upon induction by methanol.

In certain embodiments, a secreted polypeptide comprising one or more antigen-binding protein components or the antigen-binding protein itself is purified from yeast growth medium. In certain embodiments, the methods used to purify a polypeptide from yeast growth medium is the same as those used to purify the polypeptide from bacterial and mammalian cell supernatants.

In certain embodiments, a nucleic acid encoding a polypeptide comprising one or more antigen-binding protein components or the antigen-binding protein itself is cloned into a baculovirus expression vector, such as pVL1393 (PharMingen, San Diego, Calif.). In certain embodiments, such a vector can be used according to the manufacturer's directions (PharMingen) to infect *Spodoptera frugiperda* cells in sF9 protein-free media and to produce recombinant polypeptide. In certain embodiments, a polypeptide is purified and concentrated from such media using a heparin-Sepharose column (Pharmacia).

In certain embodiments, a polypeptide comprising one or more antigen-binding protein components or the antigen-binding protein itself is expressed in an insect system. Certain insect systems for polypeptide expression are well known to those of skill in the art. In one such system, *Autographa californica* nuclear polyhedrosis virus (AcNPV) is used as a vector to express foreign genes in *Spodoptera frugiperda* cells or in *Trichoplusia* larvae. In certain embodiments, a nucleic acid molecule encoding a polypeptide can be inserted into a nonessential gene of the virus, for example, within the polyhedrin gene, and placed under control of the promoter for that gene. In certain embodiments, successful insertion of a nucleic acid molecule will render the nonessential gene inactive. In certain embodiments, that inactivation results in a detectable characteristic. For example, inactivation of the polyhedrin gene results in the production of virus lacking coat protein.

In certain embodiments, recombinant viruses can be used to infect *S frugiperda* cells or *Trichoplusia* larvae. See e.g., Smith, et al., J. Virol., 46: 584, (1983); Engelhard et al., Proc. Nat. Acad. Sci. (USA), 91: 3224-7, (1994).

In certain embodiments, polypeptides comprising one or more antigen-binding protein components or the antigen-binding protein itself made in bacterial cells are produced as insoluble inclusion bodies in the bacteria. Host cells comprising such inclusion bodies are collected by centrifugation; washed in 0.15 M NaCl, 10 mM Tris, pH 8, 1 mM EDTA; and treated with 0.1 mg/ml lysozyme (Sigma, St. Louis, Mo.) for 15 minutes at room temperature. In certain embodiments, the lysate is cleared by sonication, and cell debris is pelleted by centrifugation for 10 minutes at 12,000.times.g. In certain embodiments, the polypeptide-containing pellet is resuspended in 50 mM Tris, pH 8, and 10 mM EDTA; layered over 50% glycerol; and centrifuged for 30 minutes at 6000.times.g. In certain embodiments, that pellet can be resuspended in standard phosphate buffered saline solution (PBS) free of Mg.sup.++ and Ca.sup.++. In certain embodiments, the polypeptide is further purified by fractionating the resuspended pellet in a denaturing SDS polyacrylamide gel (see e.g., Sambrook et al., supra). In certain embodiments, such a gel can be soaked in 0.4 M KCl to visualize the protein, which can be excised and electroeluted in gel-running buffer lacking SDS. According to certain embodiments, a Glutathione-S-Transferase (GST) fusion protein is produced in bacteria as a soluble protein. In certain embodiments, such GST fusion protein is purified using a GST Purification Module (Pharmacia).

In certain embodiments, it is desirable to "refold" certain polypeptides, e.g., polypeptides comprising one or more antigen-binding protein components or the antigen-binding protein itself. In certain embodiments, such polypeptides are produced using certain recombinant systems discussed herein. In certain embodiments, polypeptides are "refolded" and/or oxidized to form desired tertiary structure and/or to generate disulfide linkages. In certain embodiments, such structure and/or linkages are related to certain biological activity of a polypeptide. In certain embodiments, refolding is accomplished using any of a number of procedures known in the art. Exemplary methods include, but are not limited to, exposing the solubilized polypeptide agent to a pH typically above 7 in the presence of a chaotropic agent. An exemplary chaotropic agent is guanidine. In certain embodiments, the refolding/oxidation solution also contains a reducing agent and the oxidized form of that reducing agent. In certain embodiments, the reducing agent and its oxidized form are present in a ratio that will generate a particular redox potential that allows disulfide shuffling to occur. In certain embodiments, such shuffling allows the formation of cysteine bridges. Exemplary redox couples include, but are not limited to, cysteine/cystamine, glutathione/dithiobisGSH, cupric chloride, dithiothreitol DTT/dithiane DTT, and 2-mercaptoethanol (bME)/dithio-bME. In certain embodiments, a co-solvent is used to increase the efficiency of refolding. Exemplary cosolvents include, but are not limited to, glycerol, polyethylene glycol of various molecular weights, and arginine.

In certain embodiments, one substantially purifies a polypeptide comprising one or more antigen-binding protein components or the antigen-binding protein itself. Certain protein purification techniques are known to those of skill in the art. In certain embodiments, protein purification involves crude fractionation of polypeptide fractionations from non-polypeptide fractions. In certain embodiments, polypeptides are purified using chromatographic and/or electrophoretic techniques. Exemplary purification methods include, but are not limited to, precipitation with ammonium sulphate; precipitation with PEG; immunoprecipitation; heat denaturation followed by centrifugation; chromatography, including, but not limited to, affinity chromatography (e.g., Protein-A-Sepharose), ion exchange chromatography, exclusion chromatography, and reverse phase chromatography; gel filtration; hydroxyapatite chromatography; isoelectric focusing; polyacrylamide gel electrophoresis; and combinations of such and other techniques. In certain embodiments, a polypeptide is purified by fast protein liquid chromatography or by high pressure liquid chromatography (HPLC). In certain embodiments, purification steps can be changed or certain steps can be omitted, and still result in a suitable method for the preparation of a substantially purified polypeptide.

In certain embodiments, one quantitates the degree of purification of a polypeptide preparation. Certain methods for quantifying the degree of purification are known to those of skill in the art. Certain exemplary methods include, but are not limited to, determining the specific binding activity of the preparation and assessing the amount of a polypeptide within a preparation by SDS/PAGE analysis. Certain exemplary methods for assessing the amount of purification of a polypeptide preparation comprise calculating the binding activity of a preparation and comparing it to the binding activity of an initial extract. In certain embodiments, the results of such a calculation are expressed as "fold purification." The units used to represent the amount of binding activity depend upon the particular assay performed.

In certain embodiments, a polypeptide comprising one or more antigen-binding protein components or the antigen-binding protein itself is partially purified. Partial purification can be accomplished by using fewer purification steps or by utilizing different forms of the same general purification scheme. For example, in certain embodiments, cation-exchange column chromatography performed utilizing an HPLC apparatus will generally result in a greater "fold purification" than the same technique utilizing a low-pressure chromatography system. In certain embodiments, methods resulting in a lower degree of purification can have advantages in total recovery of polypeptide, or in maintaining binding activity of a polypeptide.

In certain instances, the electrophoretic migration of a polypeptide can vary, sometimes significantly, with different conditions of SDS/PAGE. See e.g., Capaldi, et al., Biochem. Biophys. Res. Comm., 76: 425, (1977). It will be appreciated that under different electrophoresis conditions, the apparent molecular weights of purified or partially purified polypeptide can be different.

In various embodiments described herein, antibodies can be used in vivo and in vitro for investigative or diagnostic methods, which are well known in the art. The diagnostic methods include kits, which contain antibodies in various embodiments. In other embodiments the antibodies described herein can be used as a therapeutic.

It is understood that the dual-receptor antibodies, where used in a mammal for the purpose of prophylaxis or treatment, can be administered in the form of a composition that additionally can comprise a pharmaceutically acceptable carrier. Suitable pharmaceutically acceptable carriers include, for example, one or more of water, saline, phosphate buffered saline, dextrose, glycerol, ethanol and the like, as well as combinations thereof.

Pharmaceutically acceptable carriers can further comprise minor amounts of auxiliary substances such as wetting or emulsifying agents, preservatives or buffers, which enhance the shelf life or effectiveness of the antigen-binding proteins. The compositions of the injection can, as is well known in the art, be formulated so as to provide quick, sustained or delayed release of the active ingredient after administration to the mammal.

Pharmaceutical formulations, particularly, of the antibodies for use described herein can be prepared by mixing an antibody having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g., Zn-protein complexes); and/or non-ionic surfactants. The antibody can be formulated at a concentration of between 0.5-200 mg/ml.

In therapeutic applications, compositions are administered to a patient suffering from a disease (e.g., a muscle wasting disease) in a "therapeutically effective dose." Amounts effective for this use will depend upon the severity of the disease and the general state of the patient's health. Single or multiple administrations of the compositions may be administered depending on the dosage and frequency as required and tolerated by the patient. A "patient" or "subject" as referred to herein can include both humans and other animals, particularly mammals. Thus the methods are applicable to both human therapy and veterinary applications. In various embodiments the patient is a mammal. The mammal can be a primate, or even a human.

The route of administration of a pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, intralesional routes, intramedullary, intrathecal, intraventricular, transdermal, subcutaneous, or intraperitoneal; as well as intranasal, enteral, topical, sublingual, urethral, vaginal, or rectal means, by sustained release systems or by implantation devices. Where desired, the compositions may be administered by bolus injection or continuously by infusion, or by implantation device. Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising a desired dual receptor antigen-binding protein to activin, with or without additional therapeutic agents, in a pharmaceutically acceptable vehicle. In certain embodiments, a vehicle for parenteral injection is sterile distilled water in which a dual receptor antigen-binding protein to activin receptors, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

Uses of Dual Receptor Antigen Binding Compositions

The present invention provides methods and pharmaceutical compositions for reducing or neutralizing the amount or activity of myostatin, activin, or GDF-11 in vivo and in vitro. Activin dual receptor antigen binding proteins are capable of reducing and inhibiting the biological activities of at least one of myostatin, activin A and GDF-11.

In one aspect, the present invention provides methods and reagents for treating myostatin-related and/or activin A related disorders in a subject in need of such a treatment by administering an effective dosage of a dual activin receptor antigen binding protein composition to the subject. As used herein the term "subject" refers to any animal, such as mammals including humans.

The compositions of the present invention are useful for increasing lean muscle mass in a subject. The compositions may also be useful to increase lean muscle mass in proportion to fat mass, and thus decrease fat mass as percentage of body weight in a subject. Example 3 demonstrates that dual activin antibodies described herein can increase lean muscle mass in animals.

The disorders that can be treated by a dual activin receptor antigen binding protein composition include but are not limited to various forms of muscle wasting, as well as metabolic disorders such as diabetes and related disorders, and bone degenerative diseases such as osteoporosis.

Muscle wasting disorders also include dystrophies such as Duchenne's muscular dystrophy, progressive muscular dystrophy, Becker's type muscular dystrophy, Dejerine-Landouzy muscular dystrophy, Erb's muscular dystrophy, and infantile neuroaxonal muscular dystrophy. Additional muscle wasting disorders arise from chronic diseases or disorders such as amyotrophic lateral sclerosis, congestive obstructive pulmonary disease, cancer, AIDS, renal failure, organ atrophy, androgen deprivation, and rheumatoid arthritis.

Over-expression of myostatin and/or activin may contribute to cachexia, a severe muscle wasting syndrome. Cachexia results from cancers, and also arises due to rheumatoid arthritis, diabetic nephropathy, renal failure, chemotherapy, injury due to burns, as well as other causes. In another example, serum and intramuscular concentrations of myostatin-immunoreactive protein was found to be increased in men exhibiting AIDS-related muscle wasting and was inversely related to fat-free mass (Gonzalez-Cadavid, et al., PNAS USA, 95:14938-14943, (1998)). Myostatin levels have also been shown to increase in response to burns injuries, resulting in a catabolic muscle effect (Lang, et al, FASEB J., 15, 1807-1809, (2001)). Additional conditions resulting in muscle wasting may arise from inactivity due to disability such as confinement in a wheelchair, prolonged bed rest due to stroke, illness, spinal chord injury, bone fracture or trauma, and muscular atrophy in a microgravity environment (space flight). For example, plasma myostatin immunoreactive protein was found to increase after prolonged bed rest (Zachwieja, et al. J. Gravit. Physiol., 6(2):11, (1999). It was also found that the muscles of rats exposed to a microgravity environment during a space shuttle flight expressed an increased amount of myostatin compared with the muscles of rats which were not exposed (Lalani, et al., J. Endocrin., 167(3):417-28, (2000)).

In addition, age-related increases in fat to muscle ratios, and age-related muscular atrophy appear to be related to myostatin. For example, the average serum myostatin-immunoreactive protein increased with age in groups of young (19-35 yr. old), middle-aged (36-75 yr. old), and elderly (76-92 yr old) men and women, while the average muscle mass and fat-free mass declined with age in these groups (Yarasheski, et al., J. Nutr. Aging, 6(5):343-8, (2002)). In addition, myostatin has now been found to be expressed at low levels in heart muscle and expression is upregulated in cardiomyocytes after infarct (Sharma, et al., J. Cell Physiol., 180(1):1-9, (1999)). Therefore, reducing myostatin levels in the heart muscle may improve recovery of heart muscle after infarct.

Myostatin also appears to influence metabolic disorders including type 2 diabetes, noninsulin-dependent diabetes mellitus, hyperglycemia, and obesity. For example, lack of myostatin has been shown to improve the obese and diabetic phenotypes of two mouse models (Yen, et al., FASEB 1, 8:479, (1994). The antigen-binding proteins of the present disclosure are suitable for treating such metabolic disorders. Therefore, administering the compositions of the present invention may improve diabetes, obesity, and hyperglycemic conditions in suitable subjects. In addition, compositions containing the antigen-binding protein may decrease food intake in obese individuals.

Administering the stabilized antigen-binding proteins described herein may improve bone strength and reduce osteoporosis and other degenerative bone diseases. It has been found, for example, that myostatin-deficient mice showed increased mineral content and density of the mouse humerus and increased mineral content of both trabecular and cortical bone at the regions where the muscles attach, as well as increased muscle mass (Hamrick, et al., Calcif. Tissue Int., 71(1):63-8, (2002)). In addition, the antigen-binding proteins described herein may be used to treat the effects of androgen deprivation in cases such as androgen deprivation therapy used for the treatment of prostate cancer, for example.

Also provided are methods and compositions for increasing muscle mass in food animals by administering an effective dosage of the antigen-binding protein to an animal. Since the mature C-terminal myostatin polypeptide is similar or identical in all species tested, antigen-binding proteins described herein could be expected to be effective for increasing lean muscle mass and reducing fat in any agriculturally important species including cattle, chicken, turkeys, and pigs.

Other aspects of the invention will be appreciated by one skilled in the art, and are described herein. Although various embodiments of the invention have been described herein, including the following examples, those skilled in the art will readily appreciate that the specific examples and studies detailed herein are only illustrative. It should be understood that various modifications can be made without departing from the spirit of the invention.

EXAMPLES

In mice, treatment with variant ActRIIB-Fc's produced muscle growth that was about 3 times more than that achieved by selectively inhibiting myostatin. This profound muscle growth efficacy is of therapeutic significance as it could be used to reverse pre-existing muscle loss in patients with cancer, renal failure, heart failure, burns, severe infections and many other catabolic diseases. In addition to developing soluble ActRIIB-Fc molecules, ActRIIB/ActRIIA receptor blocking antibodies were developed to stimulate muscle growth. Due to redundant functions in cell signaling, in order to achieve muscle growth efficacy similar to ActRIIB-Fc, an antagonist antibody capable of blocking both ActRIIB (SEQ ID NO: 2) (FIG. 2D) and ActRIIA (SEQ ID NO: 18) was developed.

The following sequences are relevant to this application:

TABLE 2

| SEQ ID NO. | Description* |
|---|---|
| 1 | ActRIIB-huFc |
| 2 | ActRIIB |
| 3 | M43 HC-CDR1 |
| 4 | M43 HC-CDR2 |
| 5 | M43 HC-CDR3 |
| 6 | M43 LC-CDR1 |
| 7 | M43 LC-CDR2 |
| 8 | M43 LC-CDR3 |
| 9 | R31-1 HC-CDR1 |
| 10 | R31-1 HC-CDR2 |
| 11 | R31-1 HC-CDR3 |
| 12 | R31-1 LC-CDR1 |
| 13 | R31-1 LC-CDR2 |
| 14 | R31-1 LC-CDR3 |
| 15 | M43 HC |
| 16 | M43 LC |
| 17 | ActRIIA-huFc |
| 18 | ActRIIA |

TABLE 2-continued

| SEQ ID NO. | Description* |
|---|---|
| 19 | ActRIIA (nucleic acid sequence) |
| 20 | ActRIIB (nucleic acid sequence) |
| 21 | M43 HC (nucleic acid sequence) |
| 22 | M43 LC (nucleic acid sequence) |
| 23 | Alk4 (nucleic acid sequence) |
| 24 | ActRIIB-huFC (nucleic acid sequence) |
| 25 | M10 LC |
| 26 | M10HC |
| 27 | M25 LC |
| 28 | M25HC |
| 29 | M37 LC |
| 30 | M37 HC |
| 31 | M39 LC |
| 32 | M39 HC |

*Unless otherwise indicated, the description refers to amino acid sequences

Example 1: Antibody Generation and Maturation

A dual-receptor antibody was generated by initially conducting an antibody campaign using ActRIIB-huFc (SEQ ID NO: 1) (FIG. 2D) as an antigen.

To screen the antibodies, cell reporter assay systems were developed that contained C2C12/PMARE-Luc cells stably transfected with ActRIIB (SEQ ID NO: 20); (plus ALK4, the type 1 transmembrane reporter kinase), or with ActRIIA (plus ALK4) or with both ActRIIB and ActRIIA (SEQ ID NO: 19) (plus ALK 4).

```
ActRIIB
                                                        (SEQ ID NO: 20)
                      atgacg gcgccctggg tggccctcgc cctcctctgg ggatcgctgt gcgccggctc tgggcgtggg gaggctgaga cacgggagtg catctactac aacgccaact gggagctgga gcgcaccaac cagagcggcc tggagcgctg cgaaggcgag caggacaagc ggctgcactg ctacgcctcc tggcgcaaca gctctggcac catcgagctc gtgaagaagg gctgctggct agatgacttc aactgctacg ataggcagga gtgtgtggcc actgaggaga accccaggt gtacttctgc tgctgtgaag caacttctg caacgaacgc ttcactcatt tgccagaggc tgggggcccg gaagtcacgt acgagccacc cccgacagcc cccaccctgc tcacggtgct ggcctactca ctgctgccca tcgggggcct ttccctcatc gtcctgctgg cctttggat gtaccggcat cgcaagcccc cctacggtca tgtggacatc catgaggacc ctgggcctcc accaccatcc cctctggtgg gcctgaagcc actgcagctg ctggagatca aggctcgggg gcgctttggc tgtgtctgga aggcccagct catgaatgac tttgtagctg tcaagatctt cccactccag gacaagcagt cgtggcagag tgaacgggag atcttcagca cacctggcat gaagcacgag aacctgctac agttcattgc tgccgagaag cgaggctcca acctcgaagt agagctgtgg ctcatcacgg ccttccatga caagggctcc ctcacggatt acctcaaggg gaacatcatc acatggaacg aactgtgtca tgtagcagag acgatgtcac gaggcctctc atacctgcat gaggatgtgc cctggtgccg tggcgagggc cacaagccgt ctattgccca cagggacttt aaaagtaaga atgtattgct gaagagcgac ctcacagccg tgctggctga ctttggcttg gctgttcgat ttgagccagg gaaacctcca ggggacaccc acggacaggt aggcacgaga cggtacatgg ctcctgaggt gctcgaggga gccatcaact tccagagaga tgccttcctg cgcattgaca tgtatgccat ggggttggtg ctgtgggagc ttgtgtctcg ctgcaaggct gcagacggac ccgtggatga gtacatgctg
```

-continued

```
ccctttgagg aagagattgg ccagcaccct tcgttggagg agctgcagga ggtggtggtg cacaagaaga tgaggcccac cattaaagat cactggttga acacccggg cctggcccag ctttgtgtga ccatcgagga gtgctgggac catgatgcag aggctcgctt gtccgcgggc tgtgtggaga gcgggtgtc cctgattcgg aggtcggtca acggcactac ctcggactgt ctcgtttccc tggtgacctc tgtcaccaat gtggacctgc cccctaaaga gtcaagcatc taa
```

ActRIIA sequence:
(SEQ ID NO: 19)
```
                                                 aaatgggagc tgctgcaaag ttggcgtttg ccgtctttct tatctcctgt tcttcaggtg ctatacttgg tagatcagaa actcaggagt gtcttttctt taatgctaat tgggaaaaag acagaaccaa tcaaactggt gttgaaccgt gttatggtga caaagataaa cggcggcatt gttttgctac ctggaagaat atttctggtt ccattgaaat agtgaaacaa ggttgttggc tgatgatat caactgctat gacaggactg attgtgtaga aaaaaagac agccctgaag tatattttg ttgctgtgag ggcaatatgt gtaatgaaaa gttttcttat tttccggaga tggaagtcac acagcccact tcaaatccag ttacacctaa gccaccctat acaacatcc tgctctattc cttggtgcca cttatgttaa ttgcggggat tgtcatttgt gcattttggg tgtacaggca tcacaagatg gcctaccctc ctgtacttgt tccaactcaa gacccaggac cacccccacc ttctccatta ctaggtttga accactgca gttattagaa gtgaaagcaa ggggaagatt tggttgtgtc tggaaagccc agttgcttaa cgaatatgtg ctgtcaaaa tatttccaat acaggacaaa cagtcatggc aaaatgaata cgaagtctac agtttgcctg aatgaagca tgagaacata ttacagttca ttggtgcaga aaaacgaggc accagtgttg atgtggatct ttggctgatc acagcatttc atgaaaaggg ttcactatca gactttctta aggctaatgt ggtctcttgg aatgaactgt gtcatattgc agaaaccatg gctagaggat tggcatattt acatgaggat atacctggcc taaaagatgg ccacaaacct gccatatctc acagggacat caaaagtaaa atgtgctgt tgaaaaacaa cctgacagct tgcattgctg actttgggtt ggccttaaaa tttgaggctg gcaagtctgc aggcgatacc catggacagg ttggtacccg gaggtacatg gctccagagg tattagaggg tgctataaac ttccaaaggg atgcattttt gaggatagat atgtatgcca tgggattagt cctatgggaa ctggcttctc gctgtactgc tgcagatgga cctgtagatg aatacatgtt gccatttgag gaggaaattg ccagcatcc atctcttgaa gacatgcagg aagttgttgt gcataaaaaa aagaggcctg ttttaagaga ttattggcag aaacatgctg gaatggcaat gctctgtgaa accattgaag aatgttggga tcacgacgca gaagccaggt tatcagctgg atgtgtaggt gaaagaatta cccagatgca gagactaaca atatattata ccacagagga cattgtaaca gtggtcacaa tggtgacaaa tgttgactttt cctcccaaag aatctagtct atga
```

Alk4 sequence:
(SEQ ID NO: 23)
```
atggcggagt cggccggagc ctcctccttc ttccccttg ttgtcctcct gctcgccggc agcggcgggt ccgggcccg gggggtccag gctctgctgt gtgcgtgcac cagctgcctc caggccaact acacgtgtga cagatgggg gcctgcatgg tttccattt caatctggat gggatggagc accatgtgcg cacctgcatc cccaaagtgg agctggtccc tgccgggaag cccttctact gcctgagctc ggaggacctg cgcaacaccc actgctgcta cactgactac tgcaacagga tcgacttgag ggtgcccagt ggtcacctca aggagcctga gcacccgtcc
```

-continued

```
atgtggggcc cggtggagct ggtaggcatc atcgccggcc cggtgttcct cctgttcctc atcatcatca ttgttttcct tgtcattaac tatcatcagc gtgtctatca caaccgccag agactggaca tggaagatcc ctcatgtgag atgtgtctct ccaaagacaa gacgctccag gatcttgtct acgatctctc cacctcaggg tctggctcag ggttacccct ctttgtccag cgcacagtgg cccgaaccat cgttttacaa gagattattg gcaagggtcg gtttggggaa gtatggcggg gccgctggag gggtggtgat gtggctgtga aaatattctc ttctcgtgaa gaacggtctt ggttcaggga agcagagata taccagacgg tcatgctgcg ccatgaaaac atccttggat ttattgctgc tgacaataaa gataatggca cctggacaca gctgtggctt gtttctgact atcatgagca cgggtccctg tttgattatc tgaaccggta cacagtgaca attgagggga tgattaagct ggccttgtct gctgctagtg ggctggcaca cctgcacatg gagatcgtgg gcacccaagg gaagcctgga attgctcatc gagacttaaa gtcaaagaac attctggtga agaaaaatgg catgtgtgcc atagcagacc tgggcctggc tgtccgtcat gatgcagtca ctgacaccat tgacattgcc ccgaatcaga gggtggggac caaacgatac atggcccctg aagtacttga tgaaaccatt aatatgaaac actttgactc ctttaaatgt gctgatattt atgccctcgg gcttgtatat tgggagattg ctcgaagatg caattctgga ggagtccatg aagaatatca gctgccatat tacgacttag tgccctctga cccttccatt gaggaaatgc gaaaggttgt atgtgatcag aagctgcgtc ccaacatccc caactggtgg cagagttatg aggcactgcg ggtgatgggg aagatgatgc gagagtgttg gtatgccaac ggcgcagccc gcctgacggc cctgcgcatc aagaagaccc tctcccagct cagcgtgcag gaagacgtga agatctaa
```

This led to identification of several anti-ActRIIB antibodies using ActRIIB protein as antigen. However, testing of the antibodies specific for ActRIIB binding in mice showed an in vivo muscle growth efficacy that was much weaker than ActRIIB-Fc (although the antibody did have some effect on muscle growth). This suggested further testing for a dual receptor antibody that could effectively block the signaling of both ActRIIA and ActRIIB receptors.

To that end, careful examination of antibodies from the ActRIIB screen revealed an antibody (R31-1) which bound strongly to ActRIIB, while at the same time exhibiting a weak but definite binding to ActRIIA.

antibody R31-1
(SEQ ID NO: 18)
AILGRSETQECLFFNANWEKDRTNQTGVEPCYGDKDKRRHCFATWKNISG

SIEIVKQGCWLDDINCYDRTDCVEKKDSPEVYFCCCEGNMCNEKFSYFPE

MEVTQPTSNPVTPKPPYYNILLYSLVPLMLIAGIVICAFWVYRHHKMAYP

PVLVPTQDPGPPPPSPLLGLKPLQLLEVKARGRFGCVWKAQLLNEYVAVK

IFPIQDKQSWQNEYEVYSLPGMKHENILQFIGAEKRGTSVDVDLWLITAF

HEKGSLSDFLKANVVSWNELCHIAETMARGLAYLHEDIPGLKDGHKPAIS

HRDIKSKNVLLKNNLTACIADFGLALKFEAGKSAGDTHGQVGTRRYMAPE

VLEGAINFQRDAFLRIDMYAMGLVLWELASRCTAADGPVDEYMLPFEEEI

GQHPSLEDMQEVVVHKKKRPVLRDYWQKHAGMAMLCETIEECWDHDAEAR

LSAGCVGERITQMQRLTNIITTEDIVTVVTMVTNVDFPPKESSL

Affinity maturation was next conducted using R31-1 as a parental molecule to improve the affinity toward ActRIIA without reducing the affinity for ActRIIB. (SEQ ID NO: 2) Affinity Maturation of R31-1 to M43

Anti-ActRIIB human IgG R31-1 obtained from Xenomouse immunization using soluble ActRIIB-huFc as the immunogen was shown to have <10 pM binding affinity toward AcRIIB-huFc and −1 nM binding affinity toward ActRIIAhuFc.

ActRIIA-huFc
(SEQ ID NO: 17)
AILGRSETQECLFFNANWEKDRTNQTGVEPCYGDKDKRRHCFATWKNISG

SIEIVKQGCWLDDINCYDRTDCVEKKDSPEVYFCCCEGNMCNEKFSYFPE

MEVTQPTSNPVTPKPVDKTHTCPPCPAPELLGGPSVFLFPPKPKDTLMIS

RTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSF

FLYSKLTVDKSRWQQGNVFSCSVMHEALHNHYTQKSLSLSPG

In order to completely ablate the Activin Receptor signaling pathway, simultaneous blockage of both ActRIIA and ActRIIB was necessary. To achieve this goal, an affinity maturation and screening strategy was designed to improve the affinity of R31-1 toward ActRIIA without affecting the affinity toward ActRIIB.

Single amino acid residue randomized mutagenesis (NNK codon) (N=A, T, G, or C; K=T or G) was performed on every residue in all three HC-CDRs in FIG. 1 (SEQ ID NOs: 9-11) and all three LC-CDRs in FIG. 1 (SEQ ID NOs: 12-14) of R31-1 IgG2 molecule.

Mutagenesis primers were designed by flanking NNK with 24 wild type nucleotides 5-prime and 24 wild type nucleotides 3-prime to the targeted position. 31 positions in HC-CDRs and 31 positions in LC-CDRs were mutated.

Plasmid DNA containing R31-1 IgG2.gamma. chain and plasmid DNA containing R31-1.kappa. light chain in pTT5 vector were used as the template for 62 mutagenesis reactions. A total of 1178 individual mutants were identified by sequencing and isolated. Single residue mutants of one chain were paired with the other chain of parent molecule (mutant HC: parent LC or parent HC: mutant LC) in 96-well transient transfection into 293 6E cells. Conditioned media (CM) were harvested on 7th day after transfection and used in ELISA for binding assessment.

NeutrAvidin plates coated with biotin-ActRIIB-huFc at BO % saturation concentration (0.5.mu.g/ml) and biotin-ActRIIA-huFc at 95% saturation concentration (3.33.mu.g/ml) were used for ELISA. CM of mutants was blocked in 2% BSA/2% MPBS before being incubated on antigen coated plates. After 1 hr RT (room temperature) incubation, plates were washed 5.times. with PBST. Bound mutant was detected with anti-huIgG HRP at 1:3000 dilution, after 1 hr incubation. Plates were washed 5.times. with PBST. Lumi-GLO Chemiluminescent substrate (KPL, #54-61-01) was added and plates were read on Envision. Mutants with impaired ActRIIA and ActRIIB binding activity, compared to R31-1, were eliminated.

For secondary screening to identify beneficial single residue mutants, ELISA was done at higher stringency using NeutrAvidin plates coated with biotin-ActRIIB-huFc at 0.1.mu.g/ml and biotin-ActRIIA-huFc at 0.5.mu.g/ml. Fourteen beneficial single-residue mutants (11 HC mutations in 5 positions and 3 LC mutations in 3 positions) with similar or improved ActRIIB binding activity and improved ActRIIA binding activity, compared to R31-1, were identified. One mutant is in LC-CDR1 (LC1-Y12W), two in LC-CDR3 (LC3-Y3W, LC3-W9H), three in HC-CDR1 (HC1-Y2S, HC1-Y2D, HC1S5A), five in HC-CDR2 (HC2-G1D, HC2-G1V, HC2-G1S, HC2-G1A, HC2-Y10F), and three in HC-CDR3 (HC3-S4W, HC3-S4Y, HC3-S4T).

Single-residue HC mutants were paired with single-residue LC mutants in a matrix for transient transfection into 293 6E in 96-well plates to generate 33 double-mutant IgGs that contain one mutation each in LC and He. The IgG2 concentration of crude CM samples was measured by Forte-Bio using protein A Biosensor and normalized. To select double mutants with significantly improved ActRIIA binding and unchanged AcRIIB binding, titration ELISA was done on NeutrAvidin plates coated with Biotin-VMS hFc IgG1-ACTR-2B (E2BW) and biotin-hACTR-2A (E119Q, E121Q)-hFc at various concentrations from 10.mu.g/ml to 0.001.mu.g/ml and crude CM adjusted to 1.mu.g/ml IgG2. Binding kinetic study of the selected double mutants were done on ForteBio. K-off ranking confirmation was done on BiaCore by capturing the IgG in crude CM on chip and flowing soluble receptors through. 31-1-16 with mutations at HC2-G1S and LC1-Y12W was identified to be the top clone. 31-1-27 and 31-1-43 were also good clones.

In order to further improve the affinity toward ActRIIA, single-residue beneficial mutations in different CDRs of LC or HC were combined by overlapping PCR to generate HC mutants and LC mutants with single mutation in 2 or 3 CDRs of the chain. 69 HC multiple-site mutants (mmHC) with single mutation in 2 or 3 CDRs and 2 LC multiple-site mutants (mmLC) with single mutation in CDR1 and CDR3 were constructed. Each mmHC was paired with parental LC, single-residue LC mutants and mmLC and both mmLC were paired with the parental HC in 96-well transient transfection. Crude CM samples were used in ForteBio kinetic study. 23 mutants were equal to or better than the bench mark molecule 311-16. After confirmation by BiaCore, finalS top mutants [M10 (SEQ ID NOs: 25-26), M25 (SEQ ID NOs: 27-28), M37 (SEQ ID NOs: 29-30), M39 (SEQ ID NOs: 31-32) and M43 (SEQ ID NOs: 15-16)] were selected (LC and HC amino acid sequences shown in FIGS. 2A and 2C).

Example 2: Antibody Characteristics

A Cell based assay was used to determine the binding and blocking activities against ActRIIB and ActRIIA. A myostatin/activin-responsive reporter cell line was generated by transfection of C2C12 myoblast cells (ATCC No: CRL-1772) with a pMARE-luc construct. The pMARE-luc construct is made by cloning twelve repeats of the CAGA sequence, representing the myostatin/activin response elements (Dennler, et al., EMBO, 17: 3091-3100, (1998)) into a pLuc-MCS reporter vector (Stratagene cat #219087) upstream of the TATA box. This stable cell line (C2C12/PMARE-Luc) was further transfected with activin type IIA receptor (ActRIIA) plus activin type 1 transmembrane reporter kinase (ALK4) or activin type IIB receptor (ActRIIB) plus ALK4 or ActRIIA and ActRIIB combination plus ALK4 to generate each individual stable cell lines. When myostatin or activinA binds the cell receptors, the Smad pathway is activated, and phosphorylated Smad binds to the response element (Macias-Silva et al. Cell 87:1215 (1996)), resulting in the expression of the luciferase gene. Luciferase activity was then measured using a commercial luciferase reporter assay kit (cat # E4550, Promega, Madison, Wis.) according to manufacturer's protocol. These stable lines of C2C12/pMARE-luc cells that have been transfected with ActRIIA+ALK4 or ActRIIB+AlK4 or ActRIIA/IIB+ALK4 were used to measure activity according to the following procedure. Reporter cells were plated into 96 well cultures. Screening using dilutions of the dual receptor antibody as described above was performed with the concentration fixed at 4 nM myostatin or activin. Myostatin or activin was pre-incubated with the dual receptor antibody at several concentrations. Myostatin or activin activity was measured by determining the luciferase activity in the treated cultures. The IC50 values were determined for each antibody.

Affinity of M43, M37 and M25 toward huActRIIA-huFc measured in KinExa was <1 pM, which is at least 1000-fold improvement of the parental molecule R31-1. The affinity of M43 toward huActRIIB-huFc was <1 pM, which is about 10fold improvement. (See Table 3.) The sequence of the HC and LC for M43 is provided in FIG. 2A.

TABLE 3

|  | Before Maturation (R31-1) | After Maturation (M43) |
|---|---|---|
| BIAcore $K_D$ | | |
| Binding to ActRIIB | 10 pM | 1 pM |
| Binding to ActRIIA | 4 nM | 1 pM |
| Cell-Based $IC_{50}$ | | |
| ActRIIB Signaling | 8 nM | 2 nM |
| ActRIIA Signaling | 2 nM | nM |

This yielded a dual receptor blocking antibody M43, and several other related antibody molecules, which showed strong affinity for ActRIIA as well as for ActRIIB.

Cell assays using the reporter cell systems demonstrated that the dual receptor antibodies were able to strongly block myostatin and activin ligand signaling mediated by both ActRIIB and ActRIIA receptors. When M43 was added to the cell reporter assays alone, no signaling was elicited even at very high concentration.

Additional binding assays compared binding activity of the parental antibody to the mutant antibodies (M10, M25, M37, M39, M43) (FIGS. 7B-7F). In the figures huActRIIB and huActRIIA binding comparison of parental 31-1 (FIG. 7A) and 5 mutants were compared. 100 nM Ab samples were injected over immobilized mouse anti-human IgG2, 3, 4 Ab surface to certain density. hFc(G1)-hActR2A(WT), hActR2B(R64)-hFc(G1, hActR2A(E119Q)-hFc(G1), were flowed over the surface, respectively, for 3 min, followed by Buffer for more than 10 min. The Y-axis shows the receptor binding response (RU) and the time (seconds) is shown on the X-axis.

Importantly, cell based assays ruled out any intrinsic agonist activity of ActRIIB receptors as shown in FIG. 3. Thus, M43 is free from activity for antibody-mediated receptor activation.

Example 3: Effect of M43 on Body Weight and Skeletal Mass

Figure 4:
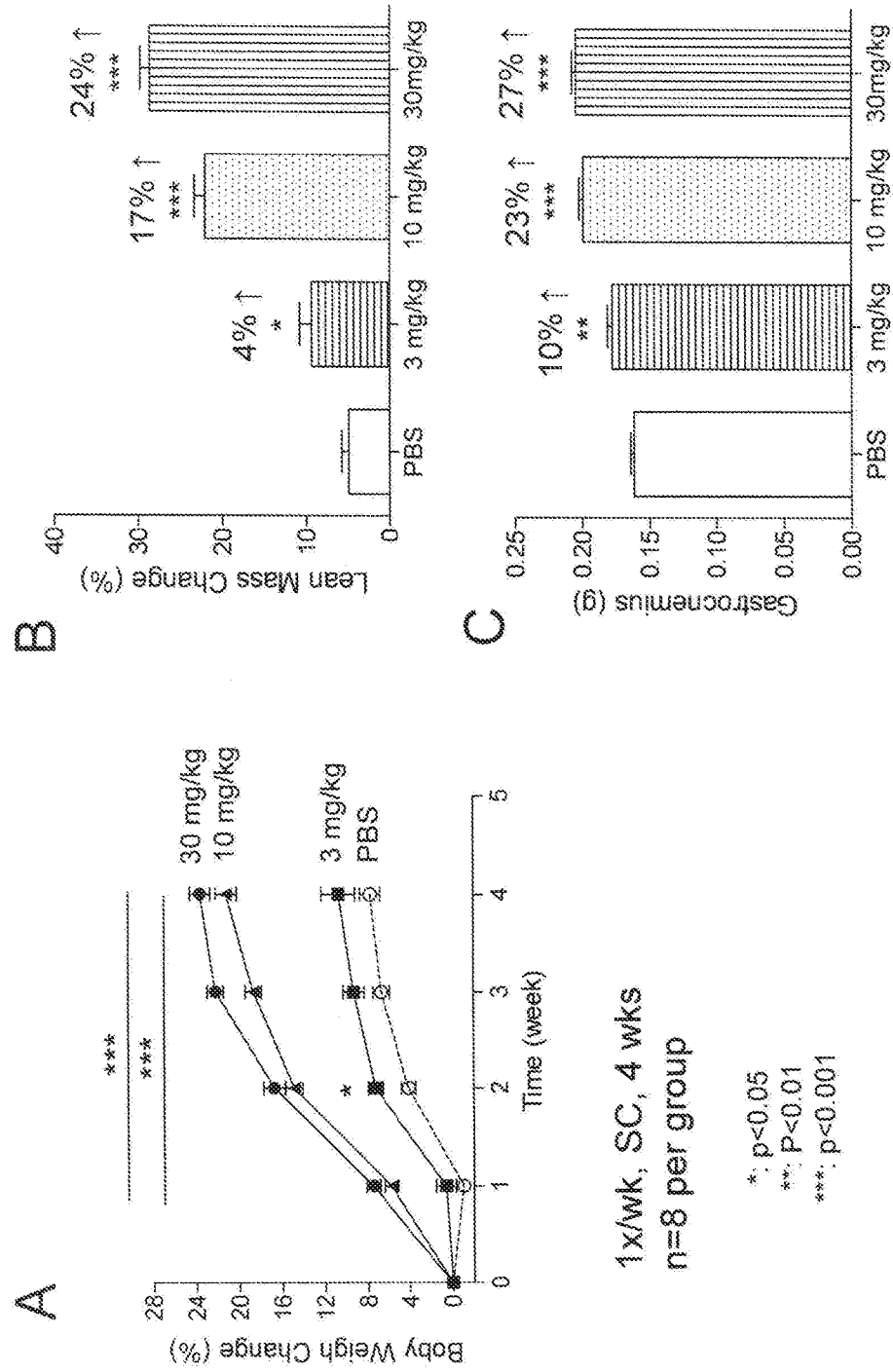
FIG. 4 shows the dose-dependent effect of M43 on body weight (panel A), lean mass (panel B) and skeletal muscle mass (panel C).

In vivo M43 demonstrated a dose-dependent effect of M43 on body weight and skeletal muscle mass in nude mice (FIG. 4, panels A-C). The effects on body weight, lean mass change and the gastrocnemius at 3 mg, 10 mg and 30 mg/kg are shown in the figures. Differences were significant at all doses.

Figure 5:
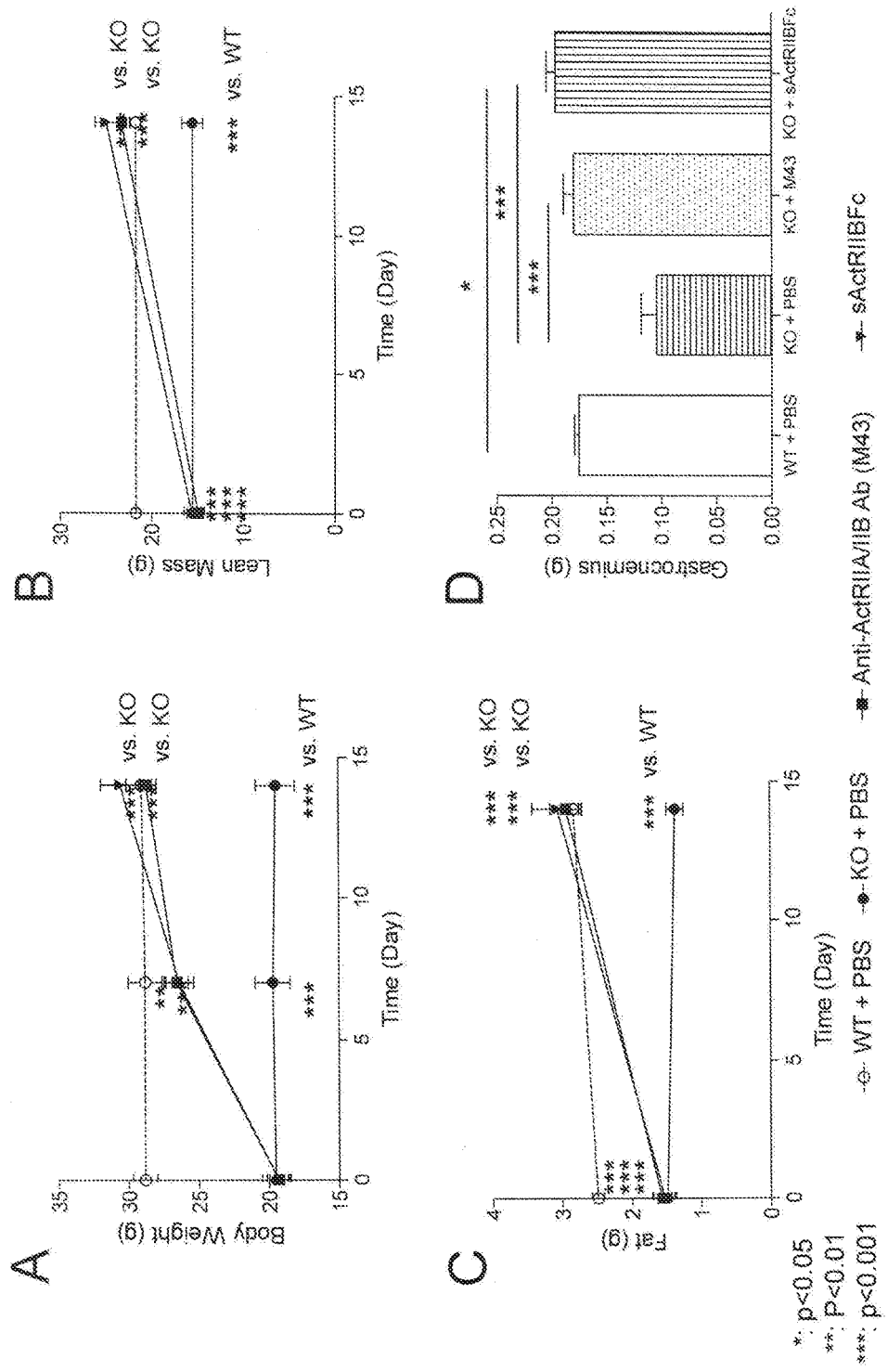
FIG. 5 shows the effect of M43 on body weight, body composition and muscle mass. 8-week-old male inhibin-alpha KO mice (n=7/group) were treated with a single injection (30 mg/kg, SC) of either M43 or sActRIIB for 2 weeks.

Head to head in vivo comparison studies in inhibin-.alpha. knock-out mice also showed that M43 had strong muscle growth efficacy similar to ActRIIB-Fc. (FIG. 5, panels A-D). Effects were seen on body weight, body composition and muscle mass.

Figure 6:
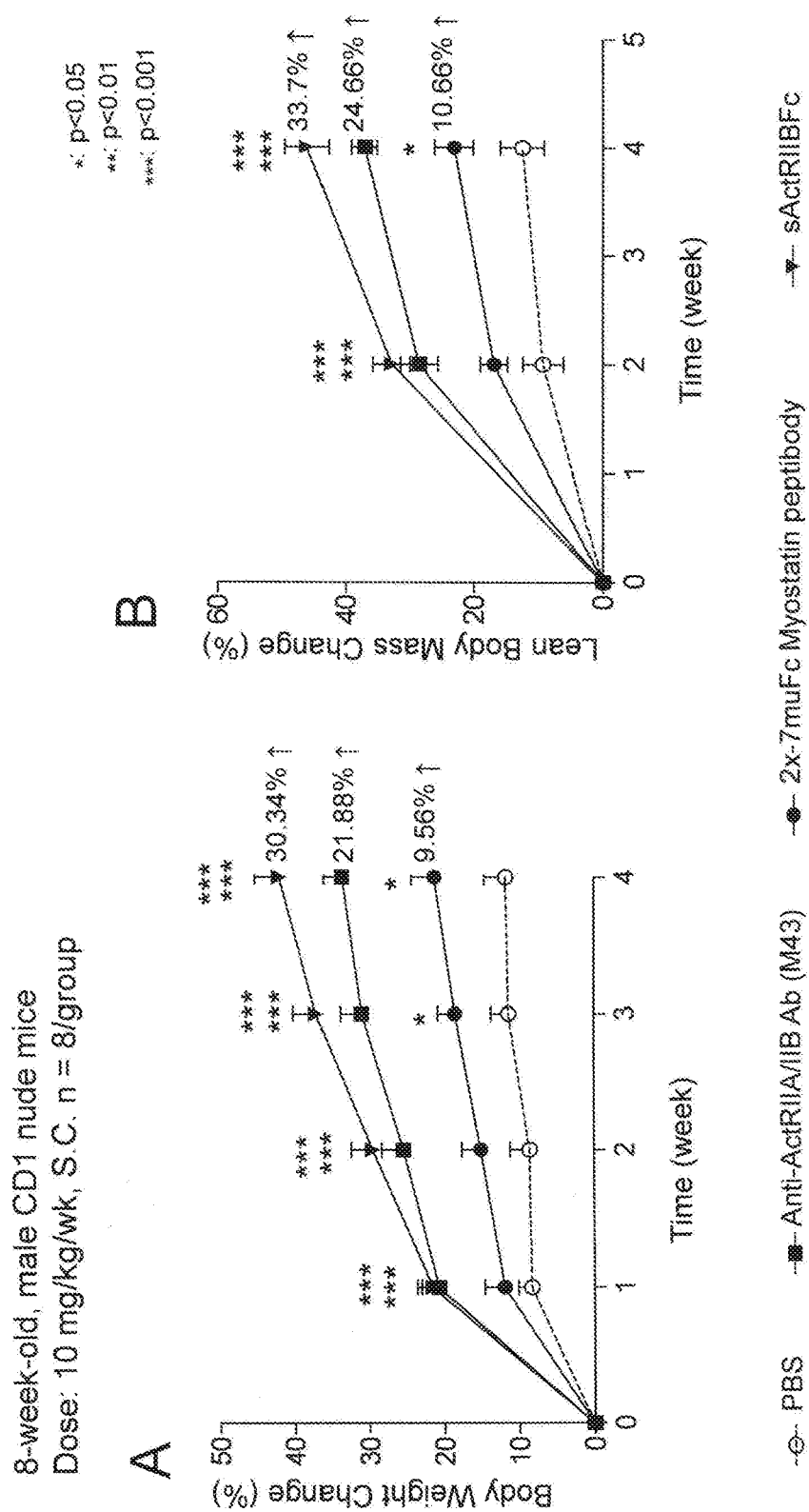
FIG. 6, panels A and B, shows the effect of M43 on body weight and lean body mass. 8-week-old, male CD1 nude mice; Dose: 10 mg/kg/week, S.C. n=8/group.
Figure 7B:
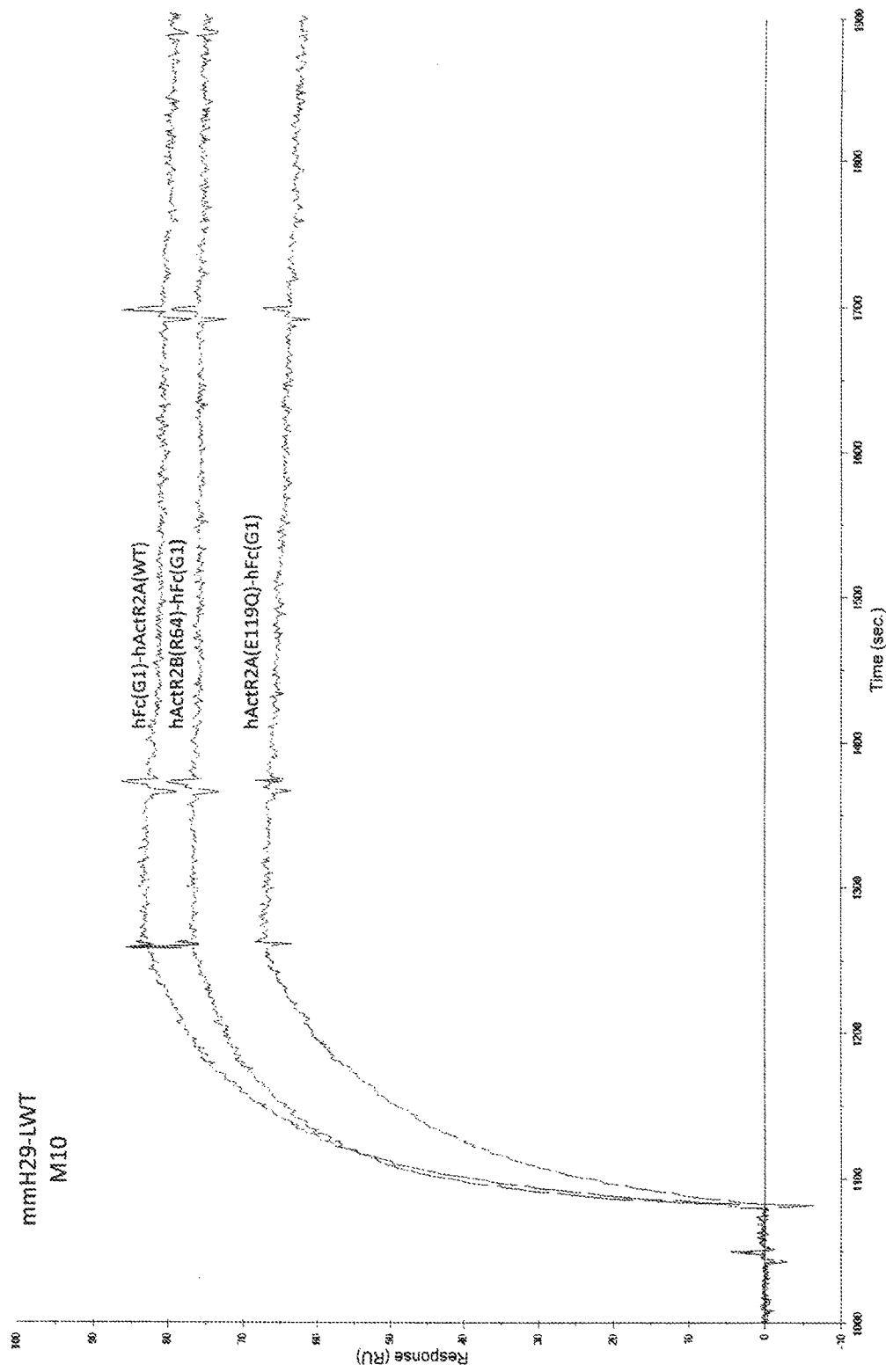
Figure 7D:
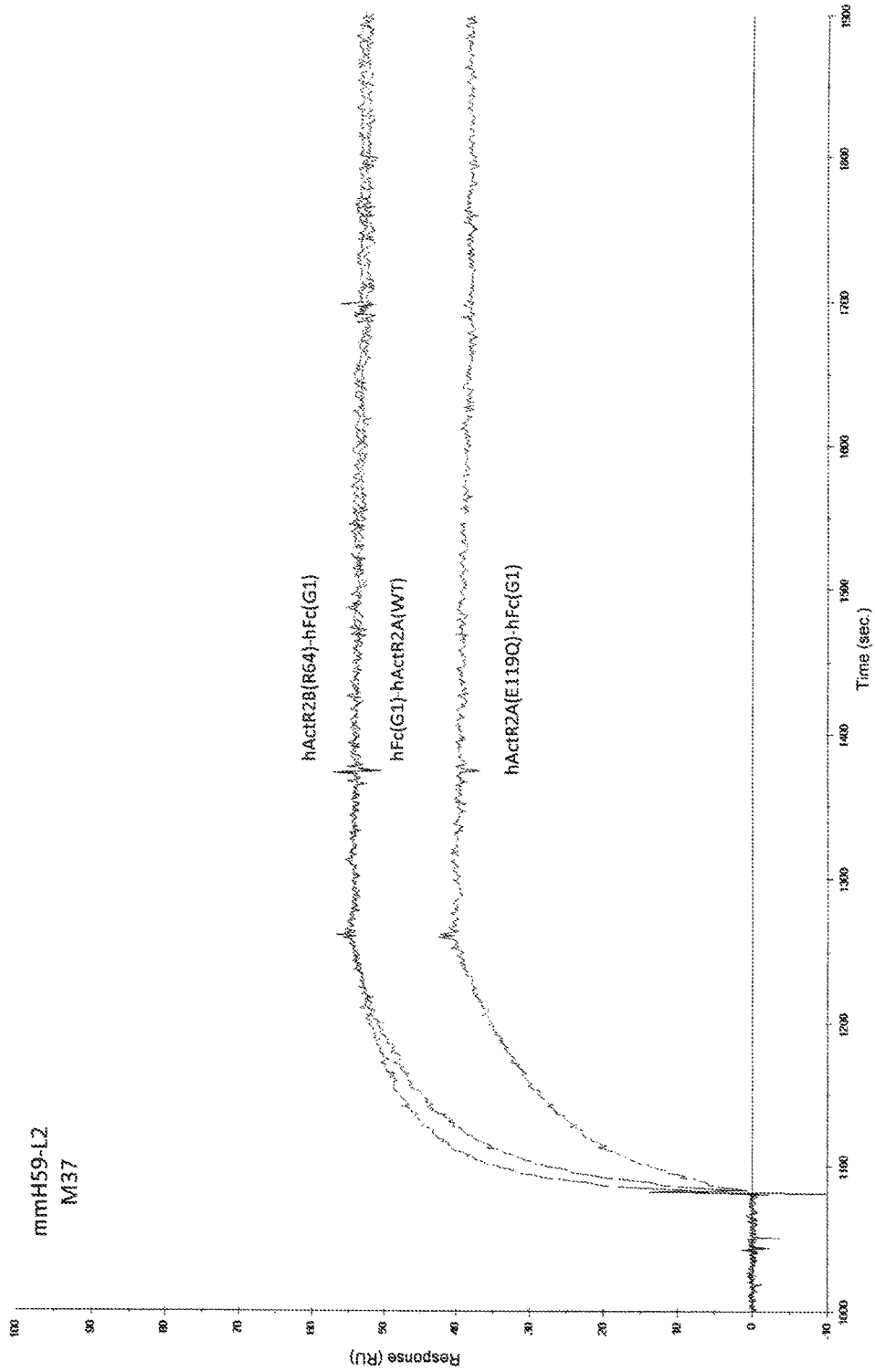

Additional studies were done comparing M43 activity to a myostatin peptibody and an activin receptor polypeptide in nude mice. Results on body weight change are shown in FIG. 6, panels A and B. It can also be seen in FIG. 6, panels A and B, that M43 compares favorably with a myostatin peptibody and a soluble activin receptor relative to a control in terms of body weight and lean body mass changes The identification of M43 (and related antibodies) and the in vitro and in vivo data clearly showed that blocking both ActRIIB and ActRIIA receptors achieved muscle growth efficacy. Given the poor homology between ActRIIB and ActRIIA proteins (their ECDs), the discovery of M43 as an antagonist dual receptor monoclonal antibody was unexpected. M43 is a fully human antibody and has clear potential clinical utilities. As the pathway blocker, M43 not only attenuates myostatin signaling, but can inhibit the signaling of activin and other ligands, e.g. GDF-11, whose increases have been implicated in pathogenesis of diseases.

For example, increased activin A expression has been associated with many cancers. Furthermore, it was recently discovered using animal tumor models that activin A is a potent stimulator for in vivo growth of certain tumors, as elevated activin A critically mediates the overproduction of angiogenesis factors in tumor microenvironment and its blockade (by sActRIIB or anti-activin antibody) dramatically slows tumor progression. In addition, over production of activin A causes heart failure in mice and its blockade reversed cardiac dysfunction. Therefore, M43 should also have potential clinical utilities beyond the treatment of muscle loss.

Throughout this specification various publications, patents and patent applications have been referenced. The disclosures of these documents in their entireties are hereby incorporated by reference into this application. The reference to such documents, however, should not be construed as an acknowledgment that such documents are prior art to the application. Further, merely because a document may be incorporated by reference, this does not necessarily indicate that the applicants are in complete agreement with the document's contents.

The invention claimed is:

1. An isolated antigen-binding protein comprising SEQ ID NO: 25 and a second polypeptide comprising SEQ ID NO: 26 wherein the antigen binding protein specifically binds to SEQ ID NO: 2 and SEQ ID NO: 18.

2. An isolated nucleic acid encoding the antigen-binding protein of claim 1.

3. An expression vector comprising the nucleic acid of claim 2.

4. A host cell comprising the vector of claim 3.

5. The host cell of claim 4 wherein the cell is a eukaryotic or prokaryotic cell.

6. The host cell of claim 5 wherein the eukaryotic cell is a mammalian cell.

7. A method of producing an antigen-binding protein, comprising culturing the host cell of claim 4 under suitable conditions such that the nucleic acid is expressed to produce the antibody.

8. The method of claim 7, further comprising recovering the antibody from a culture of the host cell.

9. A composition comprising the antigen-binding protein of claim 1 and a pharmaceutically acceptable carrier, diluent or excipient.

10. A method of increasing lean muscle mass or increasing the ratio of lean muscle mass to fat mass in a subject in need of such treatment comprising administering an effective amount the antigen-binding protein or a pharmaceutical composition containing the antigen binding protein of claim 1 to a subject in need of such treatment.

11. A method of treating or preventing a muscle wasting disease in a subject suffering from such a disorder comprising administering an effective amount of a therapeutic composition containing the antigen-binding polypeptide of claim 1 to the subject.

* * * * *

SEQUENCE LISTING

```
<160> NUMBER OF SEQ ID NOS: 33

<210> SEQ ID NO 1
<211> LENGTH: 362
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Thr Ala Pro Trp Val Ala Leu Ala Leu Leu Trp Gly Ser Leu Trp
1               5                   10                  15

Pro Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Ala
    50                  55                  60

Asn Ser Ser Gly Thr Ile Glu Leu Val Lys Lys Gly Cys Trp Leu Asp
65                  70                  75                  80
```

```
Asp Phe Asn Cys Tyr Asp Arg Gln Glu Cys Val Ala Thr Glu Glu Asn
                85                  90                  95
Pro Gln Val Tyr Phe Cys Cys Glu Gly Asn Phe Cys Asn Glu Arg
            100                 105                 110
Phe Thr His Leu Pro Glu Ala Gly Pro Glu Val Thr Tyr Glu Pro
        115                 120                 125
Pro Pro Thr Ala Pro Thr Val Asp Lys Thr His Thr Cys Pro Pro Cys
130                 135                 140
Pro Ala Pro Glu Leu Leu Gly Gly Pro Ser Val Phe Leu Phe Pro Pro
145                 150                 155                 160
Lys Pro Lys Asp Thr Leu Met Ile Ser Arg Thr Pro Glu Val Thr Cys
                165                 170                 175
Val Val Val Asp Val Ser His Glu Asp Pro Glu Val Lys Phe Asn Trp
            180                 185                 190
Tyr Val Asp Gly Val Glu Val His Asn Ala Lys Thr Lys Pro Arg Glu
        195                 200                 205
Glu Gln Tyr Asn Ser Thr Tyr Arg Val Val Ser Val Leu Thr Val Leu
    210                 215                 220
His Gln Asp Trp Leu Asn Gly Lys Glu Tyr Lys Cys Lys Val Ser Asn
225                 230                 235                 240
Lys Ala Leu Pro Ala Pro Ile Glu Lys Thr Ile Ser Lys Ala Lys Gly
                245                 250                 255
Gln Pro Arg Glu Pro Gln Val Tyr Thr Leu Pro Pro Ser Arg Asp Glu
            260                 265                 270
Leu Thr Lys Asn Gln Val Ser Leu Thr Cys Leu Val Lys Gly Phe Tyr
        275                 280                 285
Pro Ser Asp Ile Ala Val Glu Trp Glu Ser Asn Gly Gln Pro Glu Asn
    290                 295                 300
Asn Tyr Lys Thr Thr Pro Pro Val Leu Asp Ser Asp Gly Ser Phe Phe
305                 310                 315                 320
Leu Tyr Ser Lys Leu Thr Val Asp Lys Ser Arg Trp Gln Gln Gly Asn
                325                 330                 335
Val Phe Ser Cys Ser Val Met His Glu Ala Leu His Asn His Tyr Thr
            340                 345                 350
Gln Lys Ser Leu Ser Leu Ser Pro Gly Lys
        355                 360

<210> SEQ ID NO 2
<211> LENGTH: 134
<212> TYPE: PRT
<213> ORGANISM: Homo sapiens

<400> SEQUENCE: 2

Met Thr Ala Pro Trp Val Ala Leu Ala Leu Leu Trp Gly Ser Leu Trp
1               5                   10                  15
Pro Gly Ser Gly Arg Gly Glu Ala Glu Thr Arg Glu Cys Ile Tyr Tyr
            20                  25                  30
Asn Ala Asn Trp Glu Leu Glu Arg Thr Asn Gln Ser Gly Leu Glu Arg
        35                  40                  45
Cys Glu Gly Glu Gln Asp Lys Arg Leu His Cys Tyr Ala Ser Trp Ala
    50                  55                  60
Asn Ser Ser Gly Thr Ile Glu Leu Val Lys Lys Gly Cys Trp Leu Asp
65                  70                  75                  80
Asp Phe Asn Cys Tyr Asp Arg Gln Glu Cys Val Ala Thr Glu Glu Asn
                85                  90                  95
```

-continued

```
Pro Gln Val Tyr Phe Cys Cys Cys Glu Gly Asn Phe Cys Asn Glu Arg
                100                 105                 110

Phe Thr His Leu Pro Glu Ala Gly Gly Pro Glu Val Thr Tyr Glu Pro
        115                 120                 125

Pro Pro Thr Ala Pro Thr
    130

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Ser Ala Met Ser
1               5

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ile Ser Val Thr Gly Gly Ser Thr Phe Tyr Thr Asp Ser Val Lys
1               5                   10                  15

Gly Arg

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Val Tyr Tyr Tyr Ser Phe Phe Asp Tyr
1               5

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Phe Asn Ser Gly Ser Val Ser Thr Ser Tyr Trp Pro Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7
```

```
Asn Thr Asn Thr Arg Ser Ser
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Leu Trp Met Gly Ser Gly Ile Trp Val
1               5                   10

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Tyr Ala Met Ser
1               5

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Ile Ser Val Thr Gly Gly Ser Thr Tyr Tyr Thr Asp Ser Val Lys
1               5                   10                  15

Gly Arg

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Tyr Tyr Ser Ser Phe Phe Asp Tyr
1               5

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Phe Asn Ser Gly Ser Val Ser Thr Ser Tyr Tyr Pro Ser
1               5                   10

<210> SEQ ID NO 13
<211> LENGTH: 7
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 13

Asn Thr Asn Thr Arg Ser Ser
1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Val Leu Tyr Met Gly Ser Gly Ile Trp Val
1               5                   10

<210> SEQ ID NO 15
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Ser
            20                  25                  30

Ala Met Ser Trp Val Arg Gln Ala Pro Gly Lys Gly Leu Glu Trp Val
        35                  40                  45

Ser Gly Ile Ser Val Thr Gly Gly Ser Thr Tyr Thr Asp Ser Val
    50                  55                  60

Lys Gly Arg Phe Thr Val Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Tyr Tyr Ser Phe Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Phe Arg Val Val Ser Val Leu Thr
290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
            325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 16
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Thr Val Val Thr Gln Glu Pro Ser Phe Ser Val Ser Pro Gly Gly
1               5                   10                  15

Thr Val Thr Leu Thr Cys Gly Phe Asn Ser Gly Ser Val Ser Thr Ser
            20                  25                  30

Tyr Trp Pro Ser Trp Tyr Gln Gln Thr Pro Gly Gln Ala Pro Arg Thr
            35                  40                  45

Leu Ile Tyr Asn Thr Asn Thr Arg Ser Ser Gly Val Pro Asp Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Trp Met Gly Ser
                85                  90                  95

Gly Ile Trp Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys

```
145                 150                 155                 160
Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 17
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Ile Leu Gly Arg Ser Glu Thr Gln Glu Cys Leu Phe Phe Asn Ala
1               5                   10                  15

Asn Trp Glu Lys Asp Arg Thr Asn Gln Thr Gly Val Glu Pro Cys Tyr
            20                  25                  30

Gly Asp Lys Asp Lys Arg Arg His Cys Phe Ala Thr Trp Lys Asn Ile
        35                  40                  45

Ser Gly Ser Ile Glu Ile Val Lys Gln Gly Cys Trp Leu Asp Asp Ile
    50                  55                  60

Asn Cys Tyr Asp Arg Thr Asp Cys Val Glu Lys Lys Asp Ser Pro Glu
65                  70                  75                  80

Val Tyr Phe Cys Cys Cys Glu Gly Asn Met Cys Asn Glu Lys Phe Ser
                85                  90                  95

Tyr Phe Pro Glu Met Glu Val Thr Gln Pro Thr Ser Asn Pro Val Thr
            100                 105                 110

Pro Lys Pro Val Asp Lys Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Asp Glu Leu Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285
```

```
Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly
            340

<210> SEQ ID NO 18
<211> LENGTH: 494
<212> TYPE: PRT
<213> ORGANISM: Homo sapiens

<400> SEQUENCE: 18

Ala Ile Leu Gly Arg Ser Glu Thr Gln Glu Cys Leu Phe Phe Asn Ala
1               5                   10                  15

Asn Trp Glu Lys Asp Arg Thr Asn Gln Thr Gly Val Glu Pro Cys Tyr
            20                  25                  30

Gly Asp Lys Asp Lys Arg Arg His Cys Phe Ala Thr Trp Lys Asn Ile
        35                  40                  45

Ser Gly Ser Ile Glu Ile Val Lys Gln Gly Cys Trp Leu Asp Asp Ile
    50                  55                  60

Asn Cys Tyr Asp Arg Thr Asp Cys Val Glu Lys Lys Asp Ser Pro Glu
65                  70                  75                  80

Val Tyr Phe Cys Cys Cys Glu Gly Asn Met Cys Asn Glu Lys Phe Ser
                85                  90                  95

Tyr Phe Pro Glu Met Glu Val Thr Gln Pro Thr Ser Asn Pro Val Thr
            100                 105                 110

Pro Lys Pro Pro Tyr Tyr Asn Ile Leu Leu Tyr Ser Leu Val Pro Leu
        115                 120                 125

Met Leu Ile Ala Gly Ile Val Ile Cys Ala Phe Trp Val Tyr Arg His
    130                 135                 140

His Lys Met Ala Tyr Pro Pro Val Leu Val Pro Thr Gln Asp Pro Gly
145                 150                 155                 160

Pro Pro Pro Pro Ser Pro Leu Leu Gly Leu Lys Pro Leu Gln Leu Leu
                165                 170                 175

Glu Val Lys Ala Arg Gly Arg Phe Gly Cys Val Trp Lys Ala Gln Leu
            180                 185                 190

Leu Asn Glu Tyr Val Ala Val Lys Ile Phe Pro Ile Gln Asp Lys Gln
        195                 200                 205

Ser Trp Gln Asn Glu Tyr Glu Val Tyr Ser Leu Pro Gly Met Lys His
    210                 215                 220

Glu Asn Ile Leu Gln Phe Ile Gly Ala Glu Lys Arg Gly Thr Ser Val
225                 230                 235                 240

Asp Val Asp Leu Trp Leu Ile Thr Ala Phe His Glu Lys Gly Ser Leu
                245                 250                 255

Ser Asp Phe Leu Lys Ala Asn Val Val Ser Trp Asn Glu Leu Cys His
            260                 265                 270

Ile Ala Glu Thr Met Ala Arg Gly Leu Ala Tyr Leu His Glu Asp Ile
        275                 280                 285

Pro Gly Leu Lys Asp Gly His Lys Pro Ala Ile Ser His Arg Asp Ile
    290                 295                 300

Lys Ser Lys Asn Val Leu Leu Lys Asn Asn Leu Thr Ala Cys Ile Ala
305                 310                 315                 320
```

```
Asp Phe Gly Leu Ala Leu Lys Phe Glu Ala Gly Lys Ser Ala Gly Asp
                325                 330                 335

Thr His Gly Gln Val Gly Thr Arg Arg Tyr Met Ala Pro Glu Val Leu
            340                 345                 350

Glu Gly Ala Ile Asn Phe Gln Arg Asp Ala Phe Leu Arg Ile Asp Met
        355                 360                 365

Tyr Ala Met Gly Leu Val Leu Trp Glu Leu Ala Ser Arg Cys Thr Ala
    370                 375                 380

Ala Asp Gly Pro Val Asp Glu Tyr Met Leu Pro Phe Glu Glu Glu Ile
385                 390                 395                 400

Gly Gln His Pro Ser Leu Glu Asp Met Gln Glu Val Val Val His Lys
                405                 410                 415

Lys Lys Arg Pro Val Leu Arg Asp Tyr Trp Gln Lys His Ala Gly Met
            420                 425                 430

Ala Met Leu Cys Glu Thr Ile Glu Glu Cys Trp Asp His Asp Ala Glu
        435                 440                 445

Ala Arg Leu Ser Ala Gly Cys Val Gly Glu Arg Ile Thr Gln Met Gln
    450                 455                 460

Arg Leu Thr Asn Ile Ile Thr Thr Glu Asp Ile Val Thr Val Val Thr
465                 470                 475                 480

Met Val Thr Asn Val Asp Phe Pro Pro Lys Glu Ser Ser Leu
                485                 490

<210> SEQ ID NO 19
<211> LENGTH: 1544
<212> TYPE: DNA
<213> ORGANISM: Homo sapiens

<400> SEQUENCE: 19
aaatgggagc tgctgcaaag ttggcgtttg ccgtctttct tatctcctgt tcttcaggtg      60
ctatacttgg tagatcagaa actcaggagt gtcttttctt taatgctaat tgggaaaaag     120
acagaaccaa tcaaactggt gttgaaccgt gttatggtga caagataaa cggcggcatt     180 gttttgctac ctggaagaat atttctggtt ccattgaaat agtgaaacaa ggttgttggc     240
tggatgatat caactgctat gacaggactg attgtgtaga aaaaaagac agccctgaag     300 tatattttg ttgctgtgag ggcaatatgt gtaatgaaaa gttttcttat tttccggaga     360
tggaagtcac acagcccact tcaaatccag ttacacctaa gccaccctat tacaacatcc     420
tgctctattc cttggtgcca cttatgttaa ttgcggggat tgtcatttgt gcattttggg     480
tgtacaggca tcacaagatg gcctaccctc ctgtacttgt tccaactcaa gacccaggac     540
cacccccacc ttctccatta ctaggtttga aaccactgca gttattagaa gtgaaagcaa     600
ggggaagatt tggttgtgtc tggaaagccc agttgcttaa cgaatatgtg gctgtcaaaa     660
tatttccaat acaggacaaa cagtcatggc aaaatgaata cgaagtctac agtttgcctg     720
gaatgaagca tgagaacata ttacagttca ttggtgcaga aaaacgaggc accagtgttg     780
atgtggatct ttggctgatc acagcatttc atgaaaaggg ttcactatca gactttctta     840
aggctaatgt ggtctcttgg aatgaactgt gtcatattgc agaaaccatg gctagaggat     900
tggcatattt acatgaggat ataccctggcc taaaagatgg ccacaaacct gccatatctc     960
acagggacat caaaagtaaa aatgtgctgt tgaaaacaa cctgacagct tgcattgctg    1020
actttggggt ggccttaaaa tttgaggctg gcaagtctgc aggcgatacc catggacagg    1080
ttggtacccg gaggtacatg gctccagagg tattagaggg tgctataaac ttccaaaggg    1140
```

```
atgcattttt gaggatagat atgtatgcca tgggattagt cctatgggaa ctggcttctc    1200
gctgtactgc tgcagatgga cctgtagatg aatacatgtt gccatttgag gaggaaattg    1260
gccagcatcc atctcttgaa gacatgcagg aagttgttgt gcataaaaaa agaggcctg     1320 tttttaagaga ttattggcag aaacatgctg gaatggcaat gctctgtgaa accattgaag   1380
aatgttggga tcacgacgca gaagccaggt tatcagctgg atgtgtaggt gaaagaatta    1440
cccagatgca gagactaaca aatattatta ccacagagga cattgtaaca gtggtcacaa    1500
tggtgacaaa tgttgactt cctcccaaag aatctagtct atga                      1544
```

<210> SEQ ID NO 20
<211> LENGTH: 402
<212> TYPE: DNA
<213> ORGANISM: Homo sapiens

<400> SEQUENCE: 20

```
atgacggcgc cctgggtggc cctcgccctc ctctggggat cgctgtggcc cggctctggg     60
cgtggggagg ctgagacacg ggagtgcatc tactacaacg ccaactggga gctggagcgc    120
accaaccaga gcggcctgga gcgctgcgaa ggcgagcagg acaagcggct gcactgctac    180
gcctcctggg ccaacagctc tggcaccatc gagctcgtga agaagggctg ctggctagat    240
gacttcaact gctacgatag caggagtgt gtggccactg aggagaaccc ccaggtgtac     300
ttctgctgct gtgaaggcaa cttctgcaac gagcgcttca ctcatttgcc agaggctggg    360
ggcccggaag tcacgtacga gccaccccg acagccccca cc                        402
```

<210> SEQ ID NO 21
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
gaggtgcagc tgttggagtc tgggggaggc ttggtacagc ctgggggtc cctgagactc       60 tcctgtgcag cctctggatt caccttagg aactctgcca tgagctgggt ccgccaggct      120
ccagggaagg ggctggagtg gtctcaggt attagtgtta ctggtggtag cactttac        180 acagactccg tgaagggccg gttcaccgtc tccagagaca attccaggaa cacgctgtat    240
ctgcaaatga acagcctgag agccgaggac acggccgtat attactgtgc gaaagtctac    300
tactatagtt tctttgacta ctggggccag ggaaccttgg tcaccgtctc tagtgcctcc    360
accaagggcc catcggtctt ccccctggcg cctgctcca ggagcacctc cgagagcaca     420
gcggccctgg gctgcctggt caaggactac ttccccgaac cggtgacggt gtcgtggaac    480
tcaggcgctc tgaccagcgg cgtgcacacc ttcccagctg tcctacagtc ctcaggactc    540
tactccctca gcagcgtggt gaccgtgccc tccagcaact tcggcaccca gacctacacc    600
tgcaacgtag atcacaagcc cagcaacacc aaggtggaca gacagttga gcgcaaatgt    660 tgtgtcgagt gctcaccgtg cccagcacca cctgtggcag accgtcagt cttcctcttc    720 cccccaaaac ccaaggacac cctcatgatc tcccggaccc ctgaggtcac gtgcgtggtg    780
gtggacgtga gccacgaaga ccccgaggtc cagttcaact ggtacgtgga cggcgtggag    840
gtgcataatg ccaagacaaa gccacgggag gagcagttca acagcacgtt ccgtgtggtc    900
agcgtcctca ccgttgtgca ccaggactgg ctgaacggca aggagtacaa gtgcaaggtc    960
```

```
tccaacaaag gcctcccagc ccccatcgag aaaaccatct ccaaaaccaa agggcagccc    1020
cgagaaccac aggtgtacac cctgccccca tcccggagg agatgaccaa gaaccaggtc    1080
agcctgacct gcctggtcaa aggcttctac cccagcgaca tcgccgtgga gtgggagagc    1140
aatgggcagc cggagaacaa ctacaagacc acacctccca tgctggactc cgacggctcc    1200
ttcttcctct acagcaagct caccgtggac aagagcaggt ggcagcaggg gaacgtcttc    1260
tcatgctccg tgatgcatga ggctctgcac aaccactaca cgcagaagag cctctccctg    1320
tctccgggta aa                                                       1332
```

<210> SEQ ID NO 22
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
cagactgtgg tgacccagga gccaagtttc tcagtgtccc ctggagggac agtcacactc     60
acttgtggct tcaactctgg ctcagtctct actagttact ggcccagctg gtaccaacag    120
accccaggcc aggctccacg cacgctcatc tacaacacaa acactcgctc ttctggggtc    180
cctgatcgct tctctggctc catccttggg aacaaagctg ccctcaccat cacggggggcc    240 caggcagatg atgaatctga ttattactgt gtgctgtgga tgggtagtgg catttgggtg    300
ttcggcggag ggaccaagct gaccgtccta ggtcagccca aggccaaccc cactgtcact    360
ctgttcccgc cctcctctga ggagctccaa gccaacaagg ccacactagt gtgtctgatc    420
agtgacttct acccgggagc tgtgacagtg gcctggaagg cagatggcag ccccgtcaag    480
gcgggagtgg agaccaccaa accctccaaa cagagcaaca caagtacgc ggccagcagc    540 tacctgagcc tgacgcccga gcagtggaag tcccacagaa gctacagctg ccaggtcacg    600
catgaaggga gcaccgtgga agagacagtg gcccctacag aatgttca               648
```

<210> SEQ ID NO 23
<211> LENGTH: 1518
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
atggcggagt cggccggagc ctcctccttc ttccccccttg ttgtcctcct gctcgccggc     60
agcggcgggt ccgggccccg gggggtccag gctctgctgt gtgcgtgcac cagctgcctc    120
caggccaact acacgtgtga cacagatggg gcctgcatgg tttccatttt caatctggat    180
gggatggagc accatgtgcg cacctgcatc cccaaagtgg agctggtccc tgccgggaag    240
cccttctact gcctgagctc ggaggacctg cgcaacaccc actgctgcta cactgactac    300
tgcaacagga tcgacttgag ggtgcccagt ggtcacctca aggagcctga gcacccgtcc    360
atgtggggcc cggtggagct ggtaggcatc atcgccggcc cggtgttcct cctgttcctc    420
atcatcatca ttgtttttcct tgtcattaac tatcatcagc gtgtctatca aaccgccag    480 agactggaca tggaagatcc ctcatgtgag atgtgtctct ccaaagacaa gacgctccag    540
gatcttgtct acgatctctc cacctcaggg tctggctcag ggttaccccct ctttgtccag    600
```

```
cgcacagtgg cccgaaccat cgttttacaa gagattattg gcaagggtcg gtttggggaa        660
gtatggcggg gccgctggag gggtggtgat gtggctgtga aaatattctc ttctcgtgaa        720
gaacggtctt ggttcaggga agcagagata taccagacgg tcatgctgcg ccatgaaaac       780
atccttggat ttattgctgc tgacaataaa gataatggca cctggacaca gctgtggctt        840
gtttctgact atcatgagca cgggtccctg tttgattatc tgaaccggta cacagtgaca        900
attgagggga tgattaagct ggccttgtct gctgctagtg ggctggcaca cctgcacatg        960
gagatcgtgg gcacccaagg gaagcctgga attgctcatc gagacttaaa gtcaaagaac       1020
attctggtga agaaaaatgg catgtgtgcc atagcagacc tgggcctggc tgtccgtcat       1080
gatgcagtca ctgacaccat tgacattgcc ccgaatcaga gggtggggac caaacgatac       1140
atggcccctg aagtacttga tgaaaccatt aatatgaaac actttgactc ctttaaatgt       1200
gctgatattt atgccctcgg gcttgtatat tgggagattg ctcgaagatg caattctgga       1260
ggagtccatg aagaatatca gctgccatat tacgacttag tgccctctga cccttccatt       1320
gaggaaatgc gaaaggttgt atgtgatcag aagctgcgtc ccaacatccc caactggtgg       1380
cagagttatg aggcactgcg ggtgatgggg aagatgatgc gagagtgttg gtatgccaac       1440
ggcgcagccc gcctgacggc cctgcgcatc aagaagaccc tctcccagct cagcgtgcag       1500
gaagacgtga agatctaa                                                     1518

<210> SEQ ID NO 24
<211> LENGTH: 1086
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
atgacggcgc cctgggtggc cctcgccctc ctctggggat cgctgtggcc cggctctggg        60
cgtggggagg ctgagacacg ggagtgcatc tactacaacg ccaactggga gctggagcgc       120
accaaccaga gcggcctgga gcgctgcgaa ggcgagcagg acaagcggct gcactgctac        180
gcctcctggg ccaacagctc tggcaccatc gagctcgtga agaagggctg ctggctagat       240
gacttcaact gctacgatag caggagtgt gtggccactg aggagaaccc ccaggtgtac        300
ttctgctgct gtgaaggcaa cttctgcaac gagcgcttca ctcatttgcc agaggctggg       360
ggcccggaag tcacgtacga gccacccccg acagccccca ccgtcgacaa aactcacaca       420
tgcccaccgt gcccagcacc tgaactcctg ggggaccgt cagtcttcct cttccccca        480 aaacccaagg acaccctcat gatctcccgg acccctgagg tcacatgcgt ggtggtggac       540
gtgagccacg aagaccctga ggtcaagttc aactggtacg tggacggcgt ggaggtgcat       600
aatgccaaga caaagccgcg ggaggagcag tacaacagca cgtaccgtgt ggtcagcgtc       660
ctcaccgtcc tgcaccagga ctggctgaat ggcaaggagt acaagtgcaa ggtctccaac       720
aaagccctcc cagcccccat cgagaaaacc atctccaaag ccaaagggca gccccgagaa       780
ccacaggtgt acaccctgcc cccatcccgg gatgagctga ccaagaacca ggtcagcctg       840
acctgcctgg tcaaaggctt ctatcccagc gacatcgccg tggagtggga gagcaatggg       900
cagccggaga acaactacaa gaccacgcct cccgtgctgg actccgacgg ctccttcttc       960
ctctacagca agctcaccgt ggacaagagc aggtggcagc aggggaacgt cttctcatgc      1020
tccgtgatgc atgaggctct gcacaaccac tacacgcaga agagcctctc cctgtctccg      1080
``` ggtaaa 1086

<210> SEQ ID NO 25
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Thr Val Val Thr Gln Glu Pro Ser Phe Ser Val Ser Pro Gly Gly
1               5                   10                  15

Thr Val Thr Leu Thr Cys Gly Phe Asn Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile Trp Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 26
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Asp
            20                  25                  30

Ala Met Ser Trp Val Arg Gln Ala Pro Gly Lys Gly Leu Glu Trp Val
        35                  40                  45

Ser Gly Ile Ser Val Thr Gly Gly Ser Thr Phe Tyr Thr Asp Ser Val
    50                  55                  60

Lys Gly Arg Phe Thr Val Ser Arg Asp Asn Ser Arg Asn Thr Leu Tyr

Leu Gln Met Asn Ser Leu Arg Ala Glu Asp Thr Ala Val Tyr Tyr Cys
65                  70                  75                  80

Ala Lys Val Tyr Tyr Thr Ser Phe Phe Asp Tyr Trp Gly Gln Gly Thr
                85                  90                  95

Leu Val Thr Val Ser Ser Ala Ser Thr Lys Gly Pro Ser Val Phe Pro
            100                 105                 110

Leu Ala Pro Cys Ser Arg Ser Thr Ser Glu Ser Thr Ala Ala Leu Gly
        115                 120                 125

Cys Leu Val Lys Asp Tyr Phe Pro Glu Pro Val Thr Val Ser Trp Asn
130                 135                 140

Ser Gly Ala Leu Thr Ser Gly Val His Thr Phe Pro Ala Val Leu Gln
                145                 150                 155                 160

Ser Ser Gly Leu Tyr Ser Leu Ser Ser Val Val Thr Val Pro Ser Ser
                165                 170                 175

Asn Phe Gly Thr Gln Thr Tyr Thr Cys Asn Val Asp His Lys Pro Ser
            180                 185                 190

Asn Thr Lys Val Asp Lys Thr Val Glu Arg Lys Cys Cys Val Glu Cys
        195                 200                 205

Pro Pro Cys Pro Ala Pro Val Ala Gly Pro Ser Val Phe Leu Phe
210                 215                 220

Pro Pro Lys Pro Lys Asp Thr Leu Met Ile Ser Arg Thr Pro Glu Val
225                 230                 235                 240

Thr Cys Val Val Val Asp Val Ser His Glu Asp Pro Glu Val Gln Phe
                245                 250                 255

Asn Trp Tyr Val Asp Gly Val Glu Val His Asn Ala Lys Thr Lys Pro
            260                 265                 270

Arg Glu Glu Gln Phe Asn Ser Thr Phe Arg Val Val Ser Val Leu Thr
        275                 280                 285

Val Val His Gln Asp Trp Leu Asn Gly Lys Glu Tyr Lys Cys Lys Val
290                 295                 300

Ser Asn Lys Gly Leu Pro Ala Pro Ile Glu Lys Thr Ile Ser Lys Thr
305                 310                 315                 320

Lys Gly Gln Pro Arg Glu Pro Gln Val Tyr Thr Leu Pro Pro Ser Arg
                325                 330                 335

Glu Glu Met Thr Lys Asn Gln Val Ser Leu Thr Cys Leu Val Lys Gly
            340                 345                 350

Phe Tyr Pro Ser Asp Ile Ala Val Glu Trp Glu Ser Asn Gly Gln Pro
        355                 360                 365

Glu Asn Asn Tyr Lys Thr Thr Pro Pro Met Leu Asp Ser Asp Gly Ser
370                 375                 380

Phe Phe Leu Tyr Ser Lys Leu Thr Val Asp Lys Ser Arg Trp Gln Gln
                385                 390                 395                 400

Gly Asn Val Phe Ser Cys Ser Val Met His Glu Ala Leu His Asn His
            405                 410                 415

Tyr Thr Gln Lys Ser Leu Ser Leu Ser Pro Gly Lys
        420                 425                 430

<210> SEQ ID NO 27
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Gln Thr Val Val Thr Gln Glu Pro Ser Phe Ser Val Ser Pro Gly Gly
1               5                   10                  15

Thr Val Thr Leu Thr Cys Gly Phe Asn Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile His Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 28
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Ser
            20                  25                  30

Ala Met Ser Trp Val Arg Gln Ala Pro Gly Lys Gly Leu Glu Trp Val
        35                  40                  45

Ser Ala Ile Ser Val Thr Gly Gly Ser Thr Tyr Tyr Thr Asp Ser Val
    50                  55                  60

Lys Gly Arg Phe Thr Val Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Tyr Tyr Tyr Ser Phe Phe Asp Tyr Trp Gly Gln Gly Thr
            100                 105                 110

Leu Val Thr Val Ser Ser Ala Ser Thr Lys Gly Pro Ser Val Phe Pro
        115                 120                 125
```

Leu Ala Pro Cys Ser Arg Ser Thr Ser Glu Ser Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 29
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Thr Val Val Thr Gln Glu Pro Ser Phe Ser Val Ser Pro Gly Gly
1               5                   10                  15

Thr Val Thr Leu Thr Cys Gly Phe Asn Ser Gly Ser Val Ser Thr Ser
            20                  25                  30

Tyr Tyr Pro Ser Trp Tyr Gln Gln Thr Pro Gly Gln Ala Pro Arg Thr

```
            35                  40                  45
Leu Ile Tyr Asn Thr Asn Thr Arg Ser Ser Gly Val Pro Asp Arg Phe
 50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Val Leu Trp Met Gly Ser
                 85                  90                  95

Gly Ile Trp Val Phe Gly Gly Gly Thr Lys Leu Thr Val Leu Gly Gln
                100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 30
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Arg Asn Tyr
             20                  25                  30

Ala Met Ala Trp Val Arg Gln Ala Pro Gly Lys Gly Leu Glu Trp Val
         35                  40                  45

Ser Gly Ile Ser Val Thr Gly Ser Thr Phe Tyr Thr Asp Ser Val
     50                  55                  60

Lys Gly Arg Phe Thr Val Ser Arg Asp Asn Arg Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Tyr Tyr Thr Ser Phe Phe Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

-continued

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 31
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Thr Val Val Thr Gln Glu Pro Ser Phe Ser Val Ser Pro Gly Gly
1               5                   10                  15

Thr Val Thr Leu Thr Cys Gly Phe Asn Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

```
Gly Ile His Val Phe Gly Gly Thr Lys Leu Thr Val Leu Gly Gln
            100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
            210                 215

<210> SEQ ID NO 32
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Ser
            20                  25                  30

Ala Met Ser Trp Val Arg Gln Ala Pro Gly Lys Gly Leu Glu Trp Val
        35                  40                  45

Ser Ser Ile Ser Val Thr Gly Ser Thr Tyr Tyr Thr Asp Ser Val
    50                  55                  60

Lys Gly Arg Phe Thr Val Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Tyr Tyr Ser Phe Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
            195                 200                 205

Asn Thr Lys Val Asp Lys Thr Val Glu Arg Lys Cys Cys Val Glu Cys
            210                 215                 220

Pro Pro Cys Pro Ala Pro Pro Val Ala Gly Pro Ser Val Phe Leu Phe
```

```
            225                 230                 235                 240
    Pro Pro Lys Pro Lys Asp Thr Leu Met Ile Ser Arg Thr Pro Glu Val
                    245                 250                 255

Thr Cys Val Val Val Asp Val Ser His Glu Asp Pro Glu Val Gln Phe
                260                 265                 270

Asn Trp Tyr Val Asp Gly Val Glu Val His Asn Ala Lys Thr Lys Pro
                275                 280                 285

Arg Glu Glu Gln Phe Asn Ser Thr Phe Arg Val Val Ser Val Leu Thr
            290                 295                 300

Val Val His Gln Asp Trp Leu Asn Gly Lys Glu Tyr Lys Cys Lys Val
    305                 310                 315                 320

Ser Asn Lys Gly Leu Pro Ala Pro Ile Glu Lys Thr Ile Ser Lys Thr
                    325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Met Leu Asp Ser Asp Gly Ser
    385                 390                 395                 400

Phe Phe Leu Tyr Ser Lys Leu Thr Val Asp Lys Ser Arg Trp Gln Gln
                    405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
            435                 440

<210> SEQ ID NO 33
<211> LENGTH: 1539
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
atgacggcgc cctgggtggc cctcgccctc ctctggggat cgctgtgcgc cggctctggg      60
cgtggggagg ctgagacacg ggagtgcatc tactacaacg ccaactggga gctggagcgc     120
accaaccaga gcggcctgga gcgctgcgaa ggcgagcagg acaagcggct gcactgctac     180
gcctcctggc gcaacagctc tggcaccatc gagctcgtga agaagggctg ctggctagat     240
gacttcaact gctacgatag caggagtgt gtggccactg aggagaaccc ccaggtgtac     300
ttctgctgct gtgaaggcaa cttctgcaac gaacgcttca ctcatttgcc agaggctggg     360
ggcccggaag tcacgtacga gccacccccg acagccccca ccctgctcac ggtgctggcc     420
tactcactgc tgcccatcgg gggccttttcc ctcatcgtcc tgctggcctt ttggatgtac     480
cggcatcgca agccccccta cggtcatgtg acatccatg aggaccctgg gcctccacca     540
ccatcccctc tggtgggcct gaagccactg cagctgctgg agatcaaggc tcggggcgc     600 tttggctgtg tctggaaggc ccagctcatg aatgactttg tagctgtcaa gatcttccca     660
ctccaggaca gcagtcgtg gcagagtgaa cgggagatct tcagcacacc tggcatgaag     720
cacgagaacc tgctacagtt cattgctgcc gagaagcgag gctccaacct cgaagtagag     780
ctgtggctca tcacggcctt ccatgacaag ggctcccctca cggattacct caaggggaac     840
```

```
atcatcacat ggaacgaact gtgtcatgta gcagagacga tgtcacgagg cctctcatac      900
ctgcatgagg atgtgccctg gtgccgtggc gagggccaca agccgtctat tgcccacagg      960
gactttaaaa gtaagaatgt attgctgaag agcgacctca cagccgtgct ggctgacttt     1020
ggcttggctg ttcgatttga gccagggaaa cctccagggg acacccacgg acaggtaggc     1080
acgagacggt acatggctcc tgaggtgctc gagggagcca tcaacttcca gagagatgcc     1140
ttcctgcgca ttgacatgta tgccatgggg ttggtgctgt gggagcttgt gtctcgctgc     1200
aaggctgcag acggacccgt ggatgagtac atgctgccct ttgaggaaga gattggccag     1260 caccttcgt tggaggagct gcaggaggtg gtggtgcaca agaagatgag gcccaccatt      1320
aaagatcact ggttgaaaca cccgggcctg gcccagcttt gtgtgaccat cgaggagtgc     1380
tgggaccatg atgcagaggc tcgcttgtcc gcgggctgtg tggaggagcg ggtgtccctg     1440
attcggaggt cggtcaacgg cactacctcg gactgtctcg tttccctggt gacctctgtc     1500
accaatgtgg acctgccccc taaagagtca agcatctaa                            1539
```